US012559730B2

(12) United States Patent (10) Patent No.: US 12,559,730 B2
Hayashi et al. (45) Date of Patent: Feb. 24, 2026

(54) MUTANT KLF PROTEIN, AND METHOD FOR PRODUCING INDUCED PLURIPOTENT STEM CELLS

(71) Applicants: RIKEN, Wako (JP); UNIVERSITY OF TSUKUBA, Tsukuba (JP)

(72) Inventors: Yohei Hayashi, Wako (JP); Evgeniia Borisova, Wako (JP); Koji Hisatake, Tsukuba (JP); Ken Nishimura, Tsukuba (JP); Fumiaki Yumoto, Tsukuba (JP)

(73) Assignees: RIKEN, Wako (JP); UNIVERSITY OF TSUKUBA, Tsukuba (JP)

( * ) Notice: Subject to any disclaimer, the term of this patent is extended or adjusted under 35 U.S.C. 154(b) by 884 days.

(21) Appl. No.: 17/758,747

(22) PCT Filed: Dec. 16, 2020

(86) PCT No.: PCT/JP2020/047050
§ 371 (c)(1),
(2) Date: Jul. 13, 2022

(87) PCT Pub. No.: WO2021/145128
PCT Pub. Date: Jul. 22, 2021

(65) Prior Publication Data
US 2023/0040622 A1 Feb. 9, 2023

(30) Foreign Application Priority Data
Jan. 16, 2020 (JP) ................................. 2020-005399

(51) Int. Cl.
| | |
|---|---|
| *C07K 14/47* | (2006.01) |
| *A61K 38/00* | (2006.01) |
| *C12N 5/074* | (2010.01) |
| *C12N 15/85* | (2006.01) |

(52) U.S. Cl.
CPC ........ *C12N 5/0696* (2013.01); *C07K 14/4705* (2013.01); *C12N 15/85* (2013.01); *A61K 38/00* (2013.01); *C12N 2501/602* (2013.01); *C12N 2501/603* (2013.01); *C12N 2501/604* (2013.01); *C12N 2501/606* (2013.01); *C12N 2506/1307* (2013.01)

(58) Field of Classification Search
CPC ........... C12N 2501/604; C12N 5/0696; C12N 2501/603; C12N 2501/606
See application file for complete search history.

(56) References Cited

U.S. PATENT DOCUMENTS

| | | |
|---|---|---|
| 2009/0068742 A1 | 3/2009 | Yamanaka et al. |
| 2010/0062533 A1 | 3/2010 | Yamanaka et al. |

FOREIGN PATENT DOCUMENTS

| | | |
|---|---|---|
| JP | 2004-520054 A | 7/2004 |
| JP | 2008283972 A | 11/2008 |
| WO | 02/066640 A2 | 8/2002 |
| WO | 2007069666 A1 | 6/2007 |

OTHER PUBLICATIONS

Bialkowska AB, Yang VW, Mallipattu SK. Krüppel-like factors in mammalian stem cells and development. Development. Mar. 1, 2017;144(5):737-754. doi: 10.1242/dev.145441. PMID: 28246209; PMCID: PMC5374354. (Year: 2017).*
Ye B, Liu B, Hao L, Zhu X, Yang L, Wang S, Xia P, Du Y, Meng S, Huang G, Qin X, Wang Y, Yan X, Li C, Hao J, Zhu P, He L, Tian Y, Fan Z. Klf4 glutamylation is required for cell reprogramming and early embryonic development in mice. Nat Commun. Mar. 28, 2018;9(1):1261. (Year: 2018).*
Tahmasebi S, Ghorbani M, Savage P, Yan K, Gocevski G, Xiao L, You L, Yang XJ. Sumoylation of Krüppel-like factor 4 inhibits pluripotency induction but promotes adipocyte differentiation. J Biol Chem. May 3, 2013;288(18):12791-804. doi: 10.1074/ jbc. M113.465443. Epub Mar. 20, 2013. (Year: 2013).*
Takahashi et al., "Induction of Pluripotent Stem Cells from Mouse Embryonic and Adult Fibroblast Cultures by Defined Factors", Cell, 2006, vol. 126, No. 4, pp. 663-676.
Takahashi et al., "Induction of Pluripotent Stem Cells from Adult Human Fibroblasts by Defined Factors", Cell, 2007, vol. 131, No. 5, pp. 861-872.
Nakagawa et al., "Generation of induced pluripotent stem cells without Myc from mouse and human fibroblasts", Nature Biotechnology, 2008, vol. 26, No. 1, pp. 101-106.
Takahashi et al., "A decade of transcription factor-mediated reprogramming to pluripotency", Nature Reviews Molecular Cell Biology, 2016, vol. 17, No. 3, pp. 183-193.
Borisova et al., "Structurally-discovered KLF4 variants accelerate and stabilize reprogramming to pluripotency" Electronic copy available at: https://ssrn.com/abstract=3741220, pp. 1-89.
JPO, Office Action issued for the corresponding Japanese patent application No. 2021-570692, issued Oct. 8, 2024, 10 pages.
Database: GenBank, [online], "Ambigolimax valentianus KLF mRNA for kruppel-like factor, complete cds," Accession No. AB185103, Apr. 8, 2014, URL: https://www.ncbi.nlm.nih.gov/nuccore/AB185103. 1.
Database: GenBank, [online], "Penaeus monodon kruppel-like factor (KLF) mRNA, complete cds," Accession No. JF927714, Nov. 8, 2011, URL: https://www.ncbi.nlm.nih.gov/nuccore/JF927714.

* cited by examiner

*Primary Examiner* — Fereydoun G Sajjadi
*Assistant Examiner* — Qinhua Gu
(74) *Attorney, Agent, or Firm* — Lucas & Mercanti, LLP

(57) ABSTRACT

There is provided a mutant KLF protein that can induce reprogramming of a somatic cell at a higher efficiency than a KLF protein having a natural amino acid sequence. There is also provided a method for efficiently producing an iPS cell by using the mutant KLF protein. There is provided a mutant KLF protein having an amino acid substitution, or a peptide fragment thereof containing the amino acid substitution.

19 Claims, 7 Drawing Sheets

Specification includes a Sequence Listing.

A

B

| KLF1 | 304 | TGEKPYACTWEGCGWRFARSDELTRHYRKHTGQRPFRCQLCPRAFSRSDHLAlHMKRHL~ | 362 | (SEQ ID NO:9) |
| KLF2 | 297 | TGEKPYHCNWDGCGWKFARSDELTRHYRKHTGHRPFQCHLCDRAFSRSDHLAlHMKRHM~ | 355 | (SEQ ID NO:10) |
| KLF4 | 455 | TGEKPYHCDWDGCGWKFARSDELTRHYRKHTGHRPFQCQKCDRAFSRSDHLAlHMKRHF~ | 513 | (SEQ ID NO:11) |
| KLF5 | 398 | TGEKPYKCTWEGCDWRFARSDELTRHYRKHTGAKPFQCGVCNRSFSRSDHLAlHMKRHQN | 457 | (SEQ ID NO:12) |

A

B

A

B

C

MUTANT KLF PROTEIN, AND METHOD FOR PRODUCING INDUCED PLURIPOTENT STEM CELLS

CROSS-REFERENCE TO RELATED APPLICATIONS

This application is a 371 of PCT/JP2020/047050, filed Dec. 16, 2020, which claims the benefit of Japanese Patent Application No. 2020-005399, filed Jan. 16, 2020.

REFERENCE TO A SEQUENCE LISTING SUBMITTED ELECTRONICALLY VIA EFS-WEB

The content of the electronically submitted sequence listing, file name: 522-1222_SequenceListing.txt; size: 90,010 bytes; and date of creation: Jul. 6, 2022, filed herewith, is incorporated herein by reference in its entirety.

TECHNICAL FIELD

The present invention relates to a mutant KLF protein, an induced pluripotent stem cell inducer, and a method for producing induced pluripotent stem cells.

BACKGROUND ART

Cell reprogramming techniques including production techniques of induced pluripotent stem cells (iPS cells) have been rapidly advanced as innovative basic techniques in bioscience, drug discovery, and regenerative medicine.

iPS cells are induced by introducing reprogramming factors such as OCT3/4, SOX2, KLF4, and C-MYC into somatic cells (Patent Literatures 1 and 2; Non-Patent Literatures 1 and 2). All these reprogramming factors are considered to serve as transcription factors to control expression of a set of genes involving self-replication or pluripotency and thereby induce reprogramming of somatic cells.

However, a production efficiency of iPS cells is extremely low. According to a conventional art, a proportion of cells where reprogramming is actually induced, among mammalian somatic cells to which reprogramming factors such as OCT3/4, SOX2, KLF4, and C-MYC are introduced, is only less than 1% (Non-Patent Literature 2).

Such a low production efficiency of iPS cells constitutes a large obstacle to clinical application. For example, when producing transplant tissues, iPS cells produced from patient's own somatic cells are preferably used from the viewpoint of immune responsiveness. However, if a production efficiency of iPS cells remains low, it will take time to prepare a sufficient number of iPS cells necessary for production of transplant tissues, and disease progression will be caused during this time. On the contrary, if a production efficiency of iPS cells can be improved, transplant tissues can be rapidly produced. Furthermore, if the number of somatic cells necessary for preparation of iPS cells is small, somatic cells collected from a patient can be decreased and a burden on the patient's body can also be reduced.

Techniques for improving safety are also explored in research for clinical applications of iPS cells. For example, a method for substituting oncogenic C-MYC with another factor is invented as a method for reducing a risk of tumorigenesis by iPS cells. However, this method extremely lowers a production efficiency of iPS cells (Non-Patent Literature 3). Improving a production efficiency of iPS cells is an important issue also in order to cover the shortcomings of such techniques for improving safety.

A common explanation for the cause of a low production efficiency of iPS cells is that the epigenetic state of somatic cells serves as a barrier that interrupts reprogramming. Thus, an approach for changing the epigenetic state of somatic cells is explored as a method for improving a production efficiency of iPS cells. A method additionally using a cytokine or a chemical substance has also been developed (Non-Patent Literature 4).

On the other hand, no attempt has been made to modify reprogramming factors themselves for use in reprogramming induction, such as OCT3/4, SOX2, KLF4, and C-MYC, from natural sequences, in particular, for improving DNA binding function. All these reprogramming factors are transcription factors, and thus it is common to consider that DNA binding functions thereof have been already optimized in the course of evolution of life. Therefore, it is hardly considered that there is a room for increasing activities of the transcription factors by artificial sequence modifications to improve a production efficiency of iPS cells, and no attempt has been made to optimize the reprogramming factors based on their molecule structures.

CITATION LIST

Patent Literature

Patent Literature 1: WO2007/069666
Patent Literature 2: JP2008-283972A

Non-Patent Literature

Non-Patent Literature 1: Takahashi K. and Yamanaka, S., Cell, 2006, Aug. 25; 126 (4): 663-76.
Non-Patent Literature 2: Takahashi K. et al., Cell, 2007, Nov. 30; 131 (5): 861-72.
Non-Patent Literature 3: Nakagawa M., et al., Nat Biotechnol. 2008 January; 26 (1): 101-6.
Non-Patent Literature 4: Takahashi K. and Yamanaka S., Nat Rev Mol Cell Biol. 2016 March; 17 (3): 183-93.

SUMMARY OF INVENTION

Technical Problem

An object of the present invention is to provide a mutant KLF protein that can induce reprogramming of somatic cells at a higher efficiency than a KLF protein having a natural amino acid sequence. An additional object thereof is to provide a method for efficiently producing iPS cells using the mutant KLF protein.

Solution to Problem

As a reprogramming factor for use in reprogramming induction, only a factor having a natural amino acid sequence has been mainly used in the past. It has been considered that if an amino acid sequence in a DNA-binding domain of a reprogramming factor is changed, the function of recognizing a target DNA sequence is likely to be affected, and an activity as a transcription factor will be decreased or lost.

While such common general knowledges are present, the present inventors tried to design a mutant reprogramming factor that can enhance a reprogramming efficiency by artificially modifying the amino acid sequence of KLF4 being one of reprogramming factors based on the molecule structure of the reprogramming factor. The present inventors first identified 19 amino acid residues that are preserved in common in reprogramming factors, KLF1, KLF2, KLF4, and KLF5 proteins (hereinafter, often collectively referred to as "KLF proteins") and that can directly interact with DNA. Subsequently, the inventors produced a group of mutant KLF4 proteins in which one of the 19 amino acid residues is substituted with alanine, and have explored a mutant having an activity of reprogramming somatic cells at a higher efficiency than a wild-type KLF4 protein. As a result, the inventors found particular substitution mutations that increase an efficiency of reprogramming somatic cells, and completed the present invention. The present invention is based on the above findings, and provides the following.

(1) A mutant KLF protein comprising an amino acid substitution, or a peptide fragment thereof comprising the amino acid substitution, wherein the amino acid substitution is substitution of any of the following:

(a) serine at position 349 and/or leucine at position 356 in the amino acid sequence represented by SEQ ID NO: 1, (b) serine at position 342 and/or leucine at position 349 in the amino acid sequence represented by SEQ ID NO: 3, (c) serine at position 500 and/or leucine at position 507 in the amino acid sequence represented by SEQ ID NO: 5, or (d) serine at position 443 and/or leucine at position 450 in the amino acid sequence represented by SEQ ID NO: 7.

(2) The mutant KLF protein or the peptide fragment thereof according to (1), wherein the substitution of (a) is S349A, and/or L356A, L356N, L356D, L356C, L356E, L356G, L356K, L356M, L356S, or L356T, the substitution of (b) is S342A, and/or L349A, L349N, L349D, L349C, L349E, L349G, L349K, L349M, L349S, or L349T, the substitution of (c) is S500A, and/or L507A, L507N, L507D, L507C, L507E, L507G, L507K, L507M, L507S, or L507T, or the substitution of (d) is S443A, and/or L450A, L450N, L450D, L450C, L450E, L450G, L450K, L450M, L450S, or L450T.

(3) A nucleic acid encoding the mutant KLF protein or the peptide fragment thereof according to (1) or (2).

(4) A gene expression vector comprising the nucleic acid according to (3), in an expressible state.

(5) An induced pluripotent stem cell (iPS cell) inducer comprising any of the mutant KLF protein or the peptide fragment thereof according to (1) or (2), the nucleic acid according to (3), or the gene expression vector according to (4).

(6) The iPS cell inducer according to (5), further comprising the following (i) and/or (ii):

(i) any of an OCT3/4 protein, a nucleic acid encoding the protein, or a gene expression vector comprising the nucleic acid in an expressible state (ii) any of a SOX1 protein, a SOX2 protein, a SOX3 protein, a SOX15 protein or a SOX17 protein, a nucleic acid encoding any of the proteins, or a gene expression vector comprising the nucleic acid in an expressible state.

(7) The iPS cell inducer according to (6), further comprising the following (iii):

(iii) any of a C-MYC protein, a T58A mutant of the C-MYC protein, an N-MYC protein or a L-MYC protein, a nucleic acid encoding any of the proteins, or a gene expression vector comprising the nucleic acid in an expressible state.

(8) A direct reprogramming agent comprising any of the mutant KLF protein or the peptide fragment thereof according to (1) or (2), the nucleic acid according to (3), or the gene expression vector according to (4).

(9) Use of the iPS cell inducer according to any one of (5) to (7), for producing an iPS cell from a somatic cell.

(10) A method for producing an iPS cell, comprising an introduction step of introducing an iPS cell inducer comprising the following [1] to [3], into a somatic cell:

[1] any of the mutant KLF4 protein or the peptide fragment thereof according to (1) or (2), the nucleic acid according to (3), or the gene expression vector according to (4),

[2] any of an OCT3/4 protein, a nucleic acid encoding the protein, or a gene expression vector comprising the nucleic acid in an expressible state, and

[3] any of a SOX1 protein, a SOX2 protein, a SOX3 protein, a SOX15 protein or a SOX17 protein, a nucleic acid encoding any of the proteins, or a gene expression vector comprising the nucleic acid in an expressible state; and a cultivation step of cultivating the somatic cell after the introduction step in the presence of any one or more of a basic fibroblast growth factor, a TGF-β1 protein, a BMP protein, a Wnt3 protein, a GSK3β inhibitor, a Wnt inhibitor, retinoic acid, ascorbic acid, and a ROCK inhibitor.

(11) A method for producing an iPS cell, comprising an introduction step of introducing an iPS cell inducer comprising the following [1] to [4], into a somatic cell:

[1] any of the mutant KLF4 protein or the peptide fragment thereof according to (1) or (2), the nucleic acid according to (3), or the gene expression vector according to (4),

[2] any of an OCT3/4 protein, a nucleic acid encoding the protein, or a gene expression vector comprising the nucleic acid in an expressible state,

[3] any of a SOX1 protein, a SOX2 protein, a SOX3 protein, a SOX15 protein or a SOX17 protein, a nucleic acid encoding any of the proteins, or a gene expression vector comprising the nucleic acid in an expressible state, and

[4] any of a C-MYC protein, an N-MYC protein, an L-MYC protein, or a T58A mutant protein of the C-MYC protein, a nucleic acid encoding any of the proteins, or a gene expression vector comprising the nucleic acid in an expressible state; and a cultivation step of cultivating the somatic cell after the introduction step.

(12) The production method according to (10) or (11), further comprising a selection step of selecting an iPS cell induced in the cultivation step.

(13) The production method according to any of (10) to (12), wherein the somatic cell is human-derived.

(14) A cancer therapeutic agent comprising, as an active ingredient, the mutant KLF protein or the peptide fragment thereof according to (1) or (2), the nucleic acid according to (3), or the gene expression vector according to (4).

The present specification encompasses the disclosure of Japanese Patent Application No. 2020-005399 that serves as the basis of the priority of the present application.

Effects of the Invention

The mutant KLF protein of the present invention can induce reprogramming of somatic cells at a higher efficiency than a KLF protein having a natural amino acid sequence.

DESCRIPTION OF EMBODIMENTS

Figure 1:
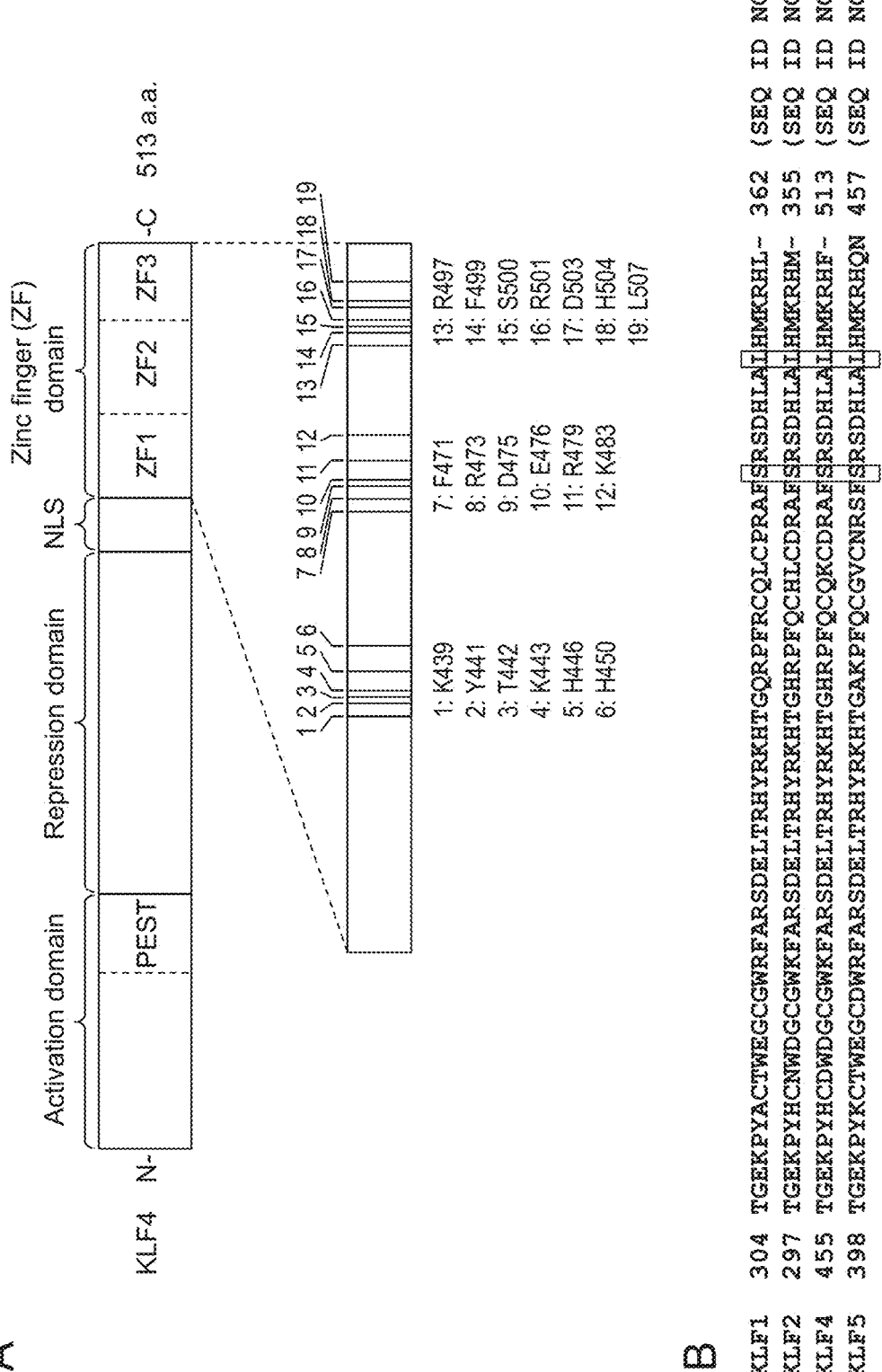
FIG. 1 illustrates the structure of a KLF protein. (A) illustrates the domain structure of a human wild-type KLF4 protein, and the positions of 19 amino acid residues that can directly interact with DNA in zinc finger domains 1 to 3 (ZF1, ZF2, and ZF3). In the drawing, "PEST" means a sequence rich in proline (P), glutamic acid (E), serine (S), and threonine (T), and "NLS" means a nuclear localization signal. (B) illustrates alignments of amino acid sequences in the C-terminal regions of wild-type KLF1 protein, KLF2 protein, KLF4 protein, and KLF5 protein. Black frames indicate the positions of the amino acid residues preserved between the KLF proteins, corresponding to S500 and L507 of the wild-type KLF4 protein (S349 and L356 of KLF1, S342 and L349 of KLF2, S443 and L450 of KLF5). The amino acid substitution positions of the mutant KLF protein of the present invention correspond to amino acid residues in the black frames.

1. Mutant KLF Protein or Peptide Fragment Thereof
1-1. Outline

A first aspect of the present invention relates to a mutant KLF protein or a peptide fragment thereof. The mutant KLF protein or the peptide fragment thereof of the present invention comprises a specified amino acid substitution, and introduction of it together with other reprogramming factors into a somatic cell can induce reprogramming of the somatic cell at a high efficiency.

1-2. Definitions

The terms frequently used herein will be defined as follows.

The term "KLF protein" is a zinc finger type transcription factor belonging to the Krueppel-like factor (KLF) family, and there are 17 types, KLF1 to KLF17 known in humans. The term "KLF protein" herein means any of KLF1, KLF2, KLF4, and KLF5 proteins. KLF1, KLF2, KLF4, or KLF5 protein, when introduced together with other reprogramming factors (for example, OCT3/4, SOX2, and C-MYC proteins) into a somatic cell, has an activity of inducing reprogramming of the somatic cell. In the present invention, the KLF protein is preferably derived from a mammal. For example, the protein is mouse, rat, rabbit, bovine, cynomolgus, marmoset, or human-derived, preferably human-derived. Examples of a human-derived KLF protein include a human wild-type KLF1 protein having an amino acid sequence represented by SEQ ID NO: 1, a human wild-type KLF2 protein having an amino acid sequence represented by SEQ ID NO: 3, a human wild-type KLF4 protein having an amino acid sequence represented by SEQ ID NO: 5, and a human wild-type KLF5 protein having an amino acid sequence represented by SEQ ID NO: 7. The term "KLF", as simply referred to herein, means any of a KLF protein, a gene or nucleic acid encoding the KLF protein, or a gene expression vector comprising the nucleic acid. Similarly, the term "mutant KLF", as simply referred to herein, means any of a mutant KLF protein, a gene or nucleic acid encoding the mutant KLF protein, or a gene expression vector comprising the nucleic acid. The same also applies to "KLF4", "mutant KLF4", and the like.

The term "induced pluripotent stem cell (iPSC; iPS cell)" refers to a cell having totipotency close to that of an embryonic stem cell (ESC; ES cell) obtained from a somatic cell by induction treatment. In general, an iPS cell has, for example, pluripotency such that it can differentiate into any type of a cell other than extraembryonic tissues in the body, and a proliferative ability such that it can proliferate almost infinitely under cultivation. An iPS cell can be obtained from various cells by various methods, and is usually produced by, for example, introducing four reprogramming factors of OCT3/4, SOX2, KLF4, and C-MYC proteins into a somatic cell.

The term "somatic cell" herein refers to any cell other than a germ cell among cells constituting an animal individual. The somatic cell herein is not limited as long as it can achieve pluripotency by reprogramming induction. The somatic cell may be derived from any animal species. Examples of the animal species from which the somatic cell is derived include mammal species. For example, the animal species may be any mammal species such as mouse, rat, rabbit, bovine, cynomolgus, marmoset, and human, and is preferably human. A tissue or an organ from which the somatic cell is derived is not particularly limited, and is preferably a tissue or an organ that can be easily collected in which reprogramming can be efficiently induced. For example, it may be, for example, skin, an organ such as liver, blood, urine, a cancer tissue, or a pulpal cell. The somatic cell may be either a differentiated cell or an undifferentiated cell, or may be an established cell, or a primary cultured cell isolated from a tissue, and is preferably a differentiated cell. Examples of the somatic cell herein include a human fibroblast, a human epithelial cell, a human hepatocyte, a human hematocyte, a mesenchymal cell, a nerve cell, and a muscle cell. A somatic cell for use in reprogramming induction herein is particularly referred to as "a somatic cell to be reprogrammed".

The term "reprogramming" herein refers to an operation or process of changing a somatic cell to another cell type. In general, the term refers to dedifferentiating a differentiated cell to change it to an undifferentiated cell. The term herein refers to an operation or process of changing a somatic cell to an iPS cell, unless particularly noted.

The phrase "reprogramming induction" or "induce reprogramming" herein means that reprogramming is actually achieved by applying an operation capable of triggering reprogramming, to a cell. In contrast, the phrase "perform reprogramming induction" means applying an operation capable of triggering reprogramming, to a cell, regardless of whether or not reprogramming is actually achieved. For example, the phrase "perform reprogramming induction" means performing an operation of introducing reprogramming factors necessary for reprogramming, into a somatic cell, and cultivating the somatic cell after the introduction, under a predetermined condition.

The term "pluripotency" herein has the same meaning as multipotency, and means a nature of a cell capable of differentiating into plural lineages of cells by differentiation. In particular, the term means a nature of being able to differentiate into all of endoderm, mesoderm and ectoderm, regardless of ability to differentiate into extraembryonic tissues such as placenta.

The term "reprogramming factor" herein refers to a factor that can trigger reprogramming of a somatic cell by being introduced alone or together with other factor(s) into the somatic cell. When simply referring to the term "reprogramming factor" without specifying that it is, for example, a protein or a gene, it means a protein to which the reprogramming factor corresponds, a nucleic acid encoding the protein, or a gene expression vector comprising the nucleic acid. Examples of the reprogramming factor include any of four factors, OCT3/4, SOX2, KLF4, and C-MYC (herein, often referred to as "four reprogramming factors"), and an associated factor of any of the four reprogramming factors.

The term "associated factor" of any of the four reprogramming factors herein refers to a factor that can induce reprogramming of a somatic cell by being introduced instead of any factor of the four reprogramming factors, into the somatic cell.

The reprogramming factor herein may be derived from any animal species. Examples of the animal species from which the reprogramming factor is derived include mammal species. For example, the animal species may be any mammal species such as mouse, rat, rabbit, bovine, cynomolgus, marmoset, and human, and is preferably human.

While the reprogramming factors and associated factors thereof will be exemplified below, the reprogramming factors and associated factors thereof herein are not limited to the following examples.

Specific examples of OCT3/4 include a human OCT3/4 protein having the amino acid sequence represented by SEQ ID NO: 13. Examples of the associated factor of OCT3/4 include NR5A2 (LRH1) and TBX3.

Specific examples of KLF4 include a human KLF4 protein having the amino acid sequence represented by SEQ ID NO: 5. Examples of the associated factor of KLF4 include KLF1, KLF2, KLF5, and the mutant KLF of the present invention. Examples include a human KLF1 protein having the amino acid sequence represented by SEQ ID NO: 1, a human KLF2 protein having the amino acid sequence represented by SEQ ID NO: 3, and a human KLF5 protein having the amino acid sequence represented by SEQ ID NO: 7.

Specific examples of SOX2 include a human SOX2 protein having the amino acid sequence represented by SEQ ID NO: 15. Examples of the associated factor of SOX2 include SOX1, SOX3, SOX15, and SOX18. Examples include a human SOX1 protein having the amino acid sequence represented by SEQ ID NO: 14, a human SOX3 protein having the amino acid sequence represented by SEQ ID NO: 16, a human SOX15 protein having the amino acid sequence represented by SEQ ID NO: 17, and a human SOX18 protein having the amino acid sequence represented by SEQ ID NO: 18.

Specific examples of C-MYC include a human C-MYC protein having the amino acid sequence represented by SEQ ID NO: 19. Examples of the associated factor of C-MYC include a T58A mutant of C-MYC, N-MYC, and L-MYC. Examples include a human N-MYC protein having the amino acid sequence represented by SEQ ID NO: 20 and a human L-MYC protein having the amino acid sequence represented by SEQ ID NO: 21.

Other examples of the reprogramming factors and the associated factors thereof include LIN28A, LIN28B, LIN41, GLIS1, FOXH1, and HMGA2.

As a method of reprogramming a somatic cell, a method of substituting some of the above reprogramming factors with a reprogramming alternative factor is also known. The term "reprogramming alternative factor" herein means a factor other than the above reprogramming factors that can trigger reprogramming when used instead of any of the above reprogramming factors. For example, a method is known in which reprogramming of a somatic cell is induced using a reprogramming alternative factor instead of C-MYC among the four reprogramming factors of OCT3/4, SOX2, KLF4, and C-MYC. Specific examples of the reprogramming alternative factor that can induce reprogramming of a somatic cell when used instead of C-MYC include a basic fibroblast growth factor (bFGF), a TGF-β1 protein, a BMP protein, a Wnt3 protein, a GSK3β inhibitor, a Wnt inhibitor, retinoic acid, ascorbic acid, and a ROCK inhibitor. Specific examples of the basic fibroblast growth factor (bFGF) include a human bFGF protein having the amino acid sequence represented by SEQ ID NO: 22, specific examples of the TGF-β1 protein include a human TGF-β1 protein having the amino acid sequence represented by SEQ ID NO: 23, specific examples of the BMP protein include a human BMP protein having the amino acid sequence represented by SEQ ID NO: 24, specific examples of the Wnt3 protein include a human Wnt3 protein having the amino acid sequence represented by SEQ ID NO: 25, specific examples of the GSK3β inhibitor include CHIR99021, examples of the Wnt inhibitor include IWR-1-endo, and examples of the ROCK inhibitor include Y-27632.

The term "more than one" herein refers to, for example, 2 to 50, 2 to 45, 2 to 40, 2 to 35, 2 to 30, 2 to 25, 2 to 20, 2 to 15, 2 to 10, 2 to 7, 2 to 5, 2 to 4, or 2 to 3. The term "amino acid identity" refers to a proportion (%) of the number of identical amino acid residues in the total number of amino acid residues when aligning amino acid sequences of two comparative polypeptides so that the number of identical amino acid residues between them is largest with inserting a gap into one or both of the amino acid sequences as appropriate. Such alignment of the two amino acid sequences for calculation of the amino acid identity can be performed using a known program such as Blast, FASTA, or ClustalW.

The term "(amino acid) substitution" herein refers to a substitution within a group of conservative amino acids having similar properties such as charge, side chain, polarity, and aromaticity, among 20 kinds of amino acids constituting a natural protein, unless particularly noted. Examples include a substitution within a group of non-charged polar amino acids (Gly, Asn, Gln, Ser, Thr, Cys, Tyr) having a low-polar side chain, a group of branched-chain amino acids (Leu, Val, Ile), a group of neutral amino acids (Gly, Ile, Val, Leu, Ala, Met, Pro), a group of neutral amino acids (Asn, Gln, Thr, Ser, Tyr, Cys) having a hydrophilic side chain, a group of acidic amino acids (Asp, Glu), a group of basic amino acids (Arg, Lys, His), a group of aromatic amino acids (Phe, Tyr, Trp). An amino acid substitution within each of the groups is preferable because it is known that such substition hardly changes properties of a polypeptide. However, for the KLF protein of the present invention, the amino acid substitution of serine at position 500 or leucine at position 507 in the amino acid sequence of a human wild-type KLF4 protein (namely, amino acid sequence represented by SEQ ID NO: 5), or the amino acid substitution at the corresponding position in another KLF protein is not limited to a substitution within a group of conservative amino acids having similar properties such as charge, side chain, polarity, and aromaticity.

1-3. Constitution

Constitutions of the mutant KLF protein or the peptide fragment thereof, of the present invention, will be specifically described hereinafter.

The mutant KLF protein of the present invention is a mutant KLF protein having an activity of inducing reprogramming of a somatic cell at a higher efficiency than a wild-type KLF protein.

The mutant KLF protein "having an activity of inducing reprogramming of a somatic cell at a higher efficiency than a wild-type KLF protein" herein means that the mutant KLF protein, when introduced into a somatic cell, leads to a significantly high efficiency of reprogramming induction of a somatic cell as compared with a wild-type KLF protein introduced under the same conditions. For example, it means that the mutant KLF protein, when introduced into a somatic cell with OCT3/4, SOX2, and C-MYC under the same conditions, leads to a significantly high efficiency of reprogramming induction of a somatic cell.

The term "significant" herein refers to being statistically significant. The term "statistically significant" means that there is a significant difference between measurement results of plural measuring objects in a statistical analysis of the results. In the present invention, a significant difference between measurement results from the mutant KLF protein and a wild-type KLF protein in a statistical analysis of the results, corresponds to the term. Examples include a case where a risk rate (significant level) of the resulting value is low, specifically less than 5% ($p<0.05$), less than 1% ($p<0.01$), or less than 0.1% ($p<0.001$). The "p (value)" represented here represents a probability where an assumption is accidently correct in a distribution of statistics assumed in a statistical test. Accordingly, it is meant that, as the "p" is smaller, the assumption is more probably true. As a test method for statistical processing, a known test method capable of determining the presence or absence of significance may be appropriately used, and the test method is not particularly limited. For example, a Student t-test method or covariate variance analysis can be used.

The mutant KLF protein of the present invention has an amino acid substitution at a particular position in the amino acid sequence of a wild-type KLF protein.

As a specific constitution, the mutant KLF protein of the present invention may comprise any amino acid substitution of serine at position 349 and/or leucine at position 356 in the amino acid sequence of the human wild-type KLF1 protein (namely, the amino acid sequence represented by SEQ ID NO: 1). The mutant KLF protein of the present invention may comprise any amino acid substitution of serine at position 342 and/or leucine at position 349 in the amino acid sequence of the human wild-type KLF2 protein (namely, the amino acid sequence represented by SEQ ID NO: 3). The mutant KLF protein of the present invention may comprise any amino acid substitution of serine at position 500 and/or leucine at position 507 in the amino acid sequence of the human wild-type KLF4 protein (namely, the amino acid sequence represented by SEQ ID NO: 5). The mutant KLF protein of the present invention may comprise amino acid substitution of serine at position 443 and/or leucine at position 450 in the amino acid sequence of the human wild-type KLF5 protein (namely, the amino acid sequence represented by SEQ ID NO: 7). The above mutant KLF proteins may be derived from a human wild-type KLF protein and comprise the above amino acid substitution in the sequence, or may be derived from a wild-type KLF protein of an animal species other than human and comprise an amino acid substitution corresponding to the above amino acid substitution, in the sequence. Hereinafter, the above positions of the amino acid substitutions will be collectively referred to as "the amino acid substitution position of the mutant KLF protein of the present invention".

An amino acid residue after substitution in the above amino acid substitution may be any of 20 kinds of amino acids residue, namely, alanine (Ala/A) residue, cysteine (Cis/C) residue, asparagic acid (Asp/D) residue, glutamic acid (Glu/E) residue, phenylalanine (Phe/F) residue, glycine (Gly/G) residue, histidine (His/H) residue, isoleucine (Ile/I)

residue, lysine (Lys/K) residue, leucine (Leu/L) residue, methionine (Met/M) residue, asparagine (Asn/N) residue, proline (Pro/P) residue, glutamine (Gln/Q) residue, arginine (Arg/R) residue, serine residue (Ser/S), threonine residue (Thr/T), valine (Val/V) residue, tryptophan (Trp/W) residue, or tyrosine (Tyr/Y) residue.

In a preferable embodiment, in the mutant KLF protein of the present invention, any amino acid substitution of serine at position 349 and/or leucine at position 356 in the amino acid sequence of the human wild-type KLF1 protein (namely, the amino acid sequence represented by SEQ ID NO: 1) is S349A, and/or L356A, L356N, L356D, L356C, L356E, L356G, L356K, L356M, L356S, or L356T; any amino acid substitution of serine at position 342 and/or leucine at position 349 in the amino acid sequence of the human wild-type KLF2 protein (namely, the amino acid sequence represented by SEQ ID NO: 3) is S342A, and/or L349A, L349N, L349D, L349C, L349E, L349G, L349K, L349M, L349S, or L349T; any amino acid substitution of serine at position 500 and/or leucine at position 507 in the amino acid sequence of the human wild-type KLF4 protein (namely, the amino acid sequence represented by SEQ ID NO: 5) is S500A, and/or L507A, L507N, L507D, L507C, L507E, L507G, L507K, L507M, L507S, or L507T; or any amino acid substitution of serine at position 443 and/or leucine at position 450 in the amino acid sequence of the human wild-type KLF5 protein (namely, the amino acid sequence represented by SEQ ID NO: 7) is S443A, and/or L450A, L450N, L450D, L450C, L450E, L450G, L450K, L450M, L450S, or L450T.

In a more preferable embodiment, in the mutant KLF protein of the present invention, any amino acid substitution of serine at position 349 and/or leucine at position 356 in the amino acid sequence of the human wild-type KLF1 protein (namely, the amino acid sequence represented by SEQ ID NO: 1) is S349A and/or L356A, L356C, L356G, L356K, or L356S; any amino acid substitution of serine at position 342 and/or leucine at position 349 in the amino acid sequence of the human wild-type KLF2 protein (namely, the amino acid sequence represented by SEQ ID NO: 3) is S342A and/or L349A, L349C, L349G, L349K, or L349S; any amino acid substitution of serine at position 500 and/or leucine at position 507 in the amino acid sequence of the human wild-type KLF4 protein (namely, the amino acid sequence represented by SEQ ID NO: 5) is S500A and/or L507A, L507C, L507G, L507K, or L507S; or amino acid substitution of serine at position 443 and/or leucine at position 450 in the amino acid sequence of the human wild-type KLF5 protein (namely, the amino acid sequence represented by SEQ ID NO: 7) is S443A and/or L450A, L450C, L450G, L450K, or L450S. For example, a human mutant KLF4 (S500A) protein having the amino acid sequence represented by SEQ ID NO: 28 or a human mutant KLF4 (L507A) protein having the amino acid sequence represented by SEQ ID NO: 30 is exemplified.

In a further preferable embodiment, in the mutant KLF protein of the present invention, any amino acid substitution of serine at position 349 and/or leucine at position 356 in the amino acid sequence of the human wild-type KLF1 protein (namely, the amino acid sequence represented by SEQ ID NO: 1) is L356A, L356G, or L356S; any amino acid substitution of serine at position 342 and/or leucine at position 349 in the amino acid sequence of the human wild-type KLF2 protein (namely, the amino acid sequence represented by SEQ ID NO: 3) is L349A, L349G, or L349S; any amino acid substitution of serine at position 500 and/or leucine at position 507 in the amino acid sequence of the human wild-type KLF4 protein (namely, the amino acid sequence represented by SEQ ID NO: 5) is L507A, L507G, or L507S; or any amino acid substitution of serine at position 443 and/or leucine at position 450 in the amino acid sequence of the human wild-type KLF5 protein (namely, the amino acid sequence represented by SEQ ID NO: 7) is L450A, L450G, or L450S. For example, a human mutant KLF4 (L507A) protein having the amino acid sequence represented by SEQ ID NO: 30 is exemplified.

The mutant KLF protein of the present invention may comprise addition, deletion, or substitution at a position other than the amino acid substitution position of the mutant KLF protein of the present invention. Such a mutant KLF protein is preferably a polypeptide having an activity of inducing reprogramming of a somatic cell at a higher efficiency than a wild-type KLF protein. For example, the mutant KLF protein of the present invention is a polypeptide which has an amino acid sequence having an amino acid identity of 80% or more, 85% or more, 90% or more, 95% or more, 96% or more, 97% or more, 98% or more, or 99% or more to the amino acid sequence represented by SEQ ID NO: 1, SEQ ID NO: 3, SEQ ID NO: 5, or SEQ ID NO: 7 in the entire sequence excluding the amino acid substitution position of the mutant KLF protein of the present invention, and which has an activity of inducing reprogramming of a somatic cell at a higher efficiency than a wild-type KLF protein. Alternatively, the mutant KLF protein of the present invention may be a polypeptide in which one or more than one amino acids in the amino acid sequence represented by SEQ ID NO: 1, SEQ ID NO: 3, SEQ ID NO: 5, or SEQ ID NO: 7 in the entire sequence excluding the amino acid substitution position of the mutant KLF protein of the present invention are deleted, substituted or added, and which has an activity of inducing reprogramming of a somatic cell at a higher efficiency than a wild-type KLF protein.

The term "peptide fragment" of the mutant KLF protein herein refers to a polypeptide fragment of the above mutant KLF protein, which comprises an amino acid residue substituted at the amino acid substitution position of the mutant KLF protein of the present invention and which retains an activity of inducing reprogramming of a somatic cell at a higher efficiency than a wild-type KLF protein. Examples include a polypeptide fragment comprising a DNA-binding moiety of the mutant KLF protein. The amino acid length of a polypeptide constituting the active fragment is not particularly limited. For example, the length may be a consecutive region of at least 10, 15, 20, 25, 30, 50, 100, 150, 200, 250, 300, 350, 400, or 450 amino acids in the KLF protein.

1-4. Effects

The mutant KLF protein or the peptide fragment thereof of the present invention has an increased transcription factor activity as compared with a wild-type KLF protein. For example, when the mutant KLF protein or the peptide fragment thereof of the present invention is introduced into a somatic cell, expression level of a target gene is increased, as compared with when a wild-type KLF protein is introduced, and thus a production efficiency of iPS cells and a cancer therapeutic efficiency are increased, as compared with a wild-type KLF protein.

The mutant KLF protein or the peptide fragment thereof of the present invention can induce reprogramming of a somatic cell at a higher efficiency than a wild-type KLF protein. For example, when the mutant KLF protein or the peptide fragment thereof of the present invention expressed and/or purified by a known method using *Escherichia coli* or the like is directly introduced together with other reprogramming factors (for example, OCT3/4, SOX2, and C-MYC) into a somatic cell, reprogramming of a somatic cell can be induced at a higher efficiency than a case where a wild-type KLF protein is introduced together with the other reprogramming factors.

According to the mutant KLF protein or the peptide fragment thereof of the present invention, iPS cells having high homogeneity can be produced. Furthermore, according to the mutant KLF protein or the peptide fragment thereof of the present invention, an iPS cell having low differentiation resistance (for example, an iPS cell having low expression level(s) of differentiation resistance marker(s) such as HERV-H and/or lincRNA-RoR) can be produced.

2. Nucleic Acid Encoding Mutant KLF Protein or Peptide Fragment Thereof

2-1. Outline

A second aspect of the present invention relates to a nucleic acid. The nucleic acid of the present invention is a nucleic acid encoding the mutant KLF protein or the peptide fragment thereof of the first aspect, for example, a DNA or an mRNA.

2-2. Constitution

The nucleic acid of the present invention encodes the mutant KLF protein or the peptide fragment thereof of the first aspect. Examples include: a nucleic acid comprising or consisting of a nucleotide sequence identical to the nucleotide sequence of a wild-type KLF gene, except for a codon encoding the amino acid substitution of serine at position 500 or leucine at position 507 in the amino acid sequence of the human wild-type KLF4 protein or the amino acid substitution at the corresponding position in any other KLF protein; and a nucleic acid comprising or consisting of a nucleotide sequence obtained by codon optimization of the above nucleotide sequence in accordance with codon usage frequency in a somatic cell into which the nucleic acid is introduced.

The nucleic acid of the present invention may be a DNA, or an RNA such as an mRNA.

Specific examples of the DNA falling into the nucleic acid of the present invention include: a DNA consisting of the nucleotide sequence represented by SEQ ID NO: 29, encoding a mutant KLF4 protein where serine at position 500 in the amino acid sequence represented by SEQ ID NO: 5 is substituted with alanine; and a DNA consisting of the nucleotide sequence represented by SEQ ID NO: 31, encoding a mutant KLF4 protein where leucine at position 507 in the amino acid sequence represented by SEQ ID NO: 5 is substituted with alanine.

The mRNA falling into the nucleic acid of the present invention is an mRNA comprising an RNA nucleotide sequence corresponding to the above DNA, as a coding region. The phrase "an RNA nucleotide sequence corresponding to the above DNA" mentioned here refers to a nucleotide sequence where thymine (T) is substituted with uracil (U) in the nucleotide sequence of the above DNA. The mRNA falling into the nucleic acid of the present invention may comprise, in addition to the coding region, a cap structure at the 5' end, a poly(A) chain at the 3' end, a 5' untranslated region (5' UTR) upstream of a start codon, and/or a 3' untranslated region (3' UTR) downstream of a stop codon. For example, 5' UTR and/or 3' UTR may comprise a sequence for regulating the amount of translation from the mRNA. For example, 3' UTR may comprise a sequence for increasing the amount of translation from an mRNA, for example, Woodchuck hepatitis virus posttranscriptional regulatory element (WPRE).

2-3. Effects

The DNA falling into the nucleic acid of the present invention can be used as a coding region (a protein translation region) in a gene expression vector of a third aspect.

The mRNA falling into the nucleic acid of the present invention can induce reprogramming of a somatic cell at a high efficiency, for example, by directly introducing it together with mRNAs encoding other reprogramming factors, into the somatic cell. In such a case, the mRNAs are rapidly degraded after transient translation and expression of the reprogramming factors, and thus genetic factors encoding the reprogramming factors are not maintained in a cell after reprogramming. Thus, a reprogramming technique having low risk of tumorigenesis and having high safety can be provided.

3. Gene Expression Vector

3-1. Outline

A third aspect of the present invention relates to a gene expression vector. The gene expression vector of the present invention comprises a nucleic acid encoding the mutant KLF protein or the peptide fragment thereof of the present invention, in an expressible state. According to the gene expression vector of the present invention, the mutant KLF protein or the peptide fragment thereof of the present invention, can be expressed in a somatic cell.

3-2. Constitution

3-2-1. Outline of Constitution

The gene expression vector of the present invention comprises a promoter, and the nucleic acid described in the second aspect, as essential components.

The "gene expression vector" herein refers to a vector comprising a gene or a gene fragment in an expressible state and comprising an expression unit capable of controlling expression of such a gene or the like. The "expressible state" herein means that a gene to be expressed is placed in a downstream region of a promoter under control of the promoter. The gene expression vector of the present invention is a vector comprising the nucleic acid of the second aspect in an expressible state, and can express the mutant KLF protein or the peptide fragment thereof, in a somatic cell.

Hereinafter, the vector that can be used as the gene expression vector of the present invention, and the promoter comprised in the gene expression vector of the present invention, as well as other optional components will be described.

3-2-2. Vector

The vector that can be used as the gene expression vector of the present invention is not particularly limited as long as it can express the mutant KLF protein or the peptide fragment thereof of the present invention, in a somatic cell. Examples include a viral vector, a plasmid vector, and an artificial chromosome vector.

The viral vector that can be used as the gene expression vector of the present invention is not particularly limited as long as it can infect a somatic cell to be reprogrammed and can express the mutant KLF protein or the peptide fragment thereof of the present invention, in the somatic cell. Examples include an adenoviral vector, an adeno-associated viral (AAV) vector, a retroviral vector, a lentiviral vector, and a Sendai viral vector. Size of a loadable DNA, types of infectable cells, cytotoxicity, the presence or absence of incorporation into host genome, an expression period, and the like are varied depending on a type of the viral vector, and can be appropriately selected depending on, for example, a type of a somatic cell to be reprogrammed. For example, a replication-defective and persistent Sendai virus vector (SeVdp vector) is particularly preferable because it has a property of persistently remaining in cytoplasm without causing integration into host genome and thus has high safety (Nishimura K., et al., J Biol Chem. 2011 Feb. 11; 286 (6): 4760-71.; Fusaki N., et al., Proc Jpn Acad Ser B Phys Biol Sci. 2009; 85 (8): 348-62.).

The plasmid vector that can be used the gene expression vector of the present invention is not particularly limited as long as it can express the mutant KLF protein or the peptide fragment thereof of the present invention, in a somatic cell to be reprogrammed when introduced into the somatic cell. The plasmid vector may be a shuttle vector replicable in mammal cells and bacteria such as *Escherichia coli*. A specific plasmid vector is, for example, an *Escherichia coli*-derived plasmid (pBR322, pUC18, pUC19, pUC118, pUC119, pBluescript, or the like), a streptomycete-derived plasmid (pIJ486, or the like), a *Bacillus subtilis*-derived plasmid (pUB110, pSH19, or the like), a yeast-derived plasmid (YEp13, YEp24, Ycp50, or the like), or a commercially available vector. Specific examples of the commercially available vector include CMV6-XL3 (OriGene Technologies), EGFP-C1, pGBT-9 (Clontech Laboratories, Inc.), pcDNA, pcDM8, and pREP4 (Thermo Fisher Scientific Inc.).

Examples of the artificial chromosome vector that can be used as the gene expression vector of the present invention include human artificial chromosome (HAC), yeast artificial chromosome (YAC), and bacterial artificial chromosome (BAC, PAC) vectors.

3-2-3. Promoter

The promoter comprised in the gene expression vector of the present invention is a promoter having an activity of inducing gene expression in a somatic cell to be reprogrammed. Since a somatic cell into which the gene expression vector of the present invention is to be introduced is, in principle, a mammal cell, in particular, a human-derived cell, the promotor may be any promoter that can express a downstream gene in such cell. Examples include a CMV promoter (CMV-IE promoter), an SV40 initial promoter, an RSV promoter, an HSV-TK promoter, an EF1α promoter, a Ub promoter, a metallothionein promoter, an SRα promoter, or a CAG promoter. Other examples also include inducible promotors such as a heatshock promoter controllable by temperature and a tetracycline-responsive promoter controllable by the presence or absence of tetracycline.

3-2-4. Other Optional Component(s)

The gene expression vector of the present invention may comprise, as optional component(s), for example, a control sequence other than the above promoter, a selection marker gene, and/or a reporter gene.

Examples of the control sequence other than the promotor, which can be comprised in the gene expression vector of the present invention, include an expression control sequence, an intron sequence, a nuclease recognition sequence, and a replication origin sequence. Examples of the expression control sequence include expression control sequences such as an enhancer, a ribosome binding sequence, a terminator, and a poly(A) addition signal. Examples of the nuclease recognition sequence include a restriction enzyme recognition sequence, a loxP sequence recognized by a Cre recombination enzyme, a sequence targeted by artificial nuclease such as ZFN or TALEN, or a sequence targeted by a CRISPR/Cas9 system. Examples of the replication origin sequence include an SV40 replication origin sequence.

For example, the nuclease recognition sequence can be introduced upstream and downstream of the coding region of the reprogramming factor in the gene expression vector of the present invention. In this case, after completion of reprogramming of a somatic cell, the nuclease can be introduced to remove the coding region of the reprogramming factor.

The selection marker gene that can be comprised in the gene expression vector of the present invention is a selection marker gene that can select a somatic cell into which the gene expression vector of the present invention is introduced. Specific examples of the selection marker gene include a drug-resistant gene such as an ampicillin-resistant gene, a kanamycin-resistant gene, a tetracycline-resistant gene, a chloramphenicol-resistant gene, a neomycin-resistant gene, a puromycin-resistant gene, or a hygromycin-resistant gene.

The reporter gene that can be comprised in the gene expression vector of the present invention is a gene encoding a reporter that can distinguish a somatic cell into which the gene expression vector of the present invention is introduced. Examples of the reporter gene include a gene encoding a fluorescent protein such as GFP or RFP, and a luciferase gene.

3-3. Effects

According to the gene expression vector of the present invention, the mutant KLF protein or the peptide fragment thereof of the present invention can be expressed in a somatic cell to be reprogrammed. Furthermore, reprogramming of a somatic cell can be induced at a high efficiency by using the gene expression vector of the present invention in combination with other reprogramming factors (for example, OCT3/4, SOX2, and C-MYC).

4. iPS Cell Inducer 4-1. Outline

A fourth aspect of the present invention relates to an induced pluripotent stem cell (iPS cell) inducer. The iPS cell inducer of the present invention comprises: any of the mutant KLF protein or the peptide fragment thereof, the nucleic acid encoding the mutant KLF protein or the peptide fragment thereof, or the gene expression vector comprising the nucleic acid, of the present invention, as an essential component; and comprises other reprogramming factor(s), as an optional component.

4-2. Constitution 4-2-1. Outline of Constitution

The iPS cell inducer of the present invention comprises, as an essential component, any of the mutant KLF protein or the peptide fragment thereof of the first aspect, the nucleic acid of the second aspect, or the gene expression vector of the third aspect (hereinafter, collectively referred to as "the mutant KLF of the present invention").

The iPS cell inducer of the present invention may comprise one or more other reprogramming factor(s) as optional component(s).

The essential component is according to the description of the first to third aspects, and thus only such optional component(s) will be described below.

4-2-2. Optional Component(s)

The iPS cell inducer of the present invention may comprise (1) one or more other reprogramming factor(s), and/or (2) a reprogramming cofactor, as optional component(s). Hereinafter, (1) and (2) will be specifically described.

(1) Other Reprogramming Factor(s)

The iPS cell inducer of the present invention may comprise one or more other reprogramming factor(s) as optional component(s). Reprogramming factor(s) other than the mutant KLF of the present invention correspond(s) to the "other reprogramming factor(s)" here mentioned. The other reprogramming factor(s) is/are not limited as long as such factor(s) is/are reprogramming factor(s) other than the mutant KLF of the present invention and can induce reprogramming of a somatic cell. Examples include OCT3/4, SOX2, C-MYC, and KLF (for example, wild-type KLF) other than the mutant KLF of the present invention, and an associated factor of any thereof. Examples of the associated factor include SOX1, SOX3, SOX15, SOX18, a T58A mutant of C-MYC, N-MYC and L-MYC, as well as wild-type KLF1, wild-type KLF2, wild-type KLF4, and wild-type KLF5. These other reprogramming factors may be any of a protein corresponding to the other reprogramming factor or a peptide fragment thereof, a nucleic acid encoding the protein or the peptide fragment thereof, or a gene expression vector comprising the nucleic acid in an expressible state. Constitutions of the nucleic acid encoding the protein corresponding to the other reprogramming factor or the peptide fragment thereof, and the gene expression vector comprising the nucleic acid in an expressible state are according to the descriptions of the second aspect and third aspect described with respect to the mutant KLF.

The number of the other reprogramming factors comprised in the iPS cell inducer of the present invention is not limited. For example, the iPS cell inducer of the present invention may comprise, as the other reprogramming factor(s), one, two, three, four, five, six, or more reprogramming factors.

When the iPS cell inducer of the present invention comprises two or more gene expression vectors, the two or more gene expression vectors may be comprised in the same vector or may be separate vectors.

In a preferable embodiment, in addition to the essential component, the iPS cell inducer of the present invention may further comprise: any of an OCT3/4 protein, a nucleic acid encoding the protein, or a gene expression vector comprising the nucleic acid in an expressible state; and/or any of a SOX1 protein, a SOX2 protein, a SOX3 protein, a SOX15 protein or a SOX17 protein, a nucleic acid encoding any of the proteins, or a gene expression vector comprising the nucleic acid in an expressible state. In addition, it may further comprise any of a C-MYC protein, a T58A mutant of the C-MYC protein, an N-MYC protein or a L-MYC protein, a nucleic acid encoding any of the proteins, or a gene expression vector comprising the nucleic acid in an expressible state.

(2) Reprogramming Cofactor

The "reprogramming cofactor" that can be comprised as an optional component in the iPS cell inducer of the present invention is a factor other than those falling into the above item (1) which can increase a reprogramming induction efficiency when introduced into a somatic cell but is not essential for reprogramming induction of a somatic cell. Examples include NANOG, NR5A2, LIN28A, LIN28B, LIN41, GLIS1, TBX3, HMGA2, FOXH1, mir-302, mir-367, mir-106a, mir-363, an shRNA or an siRNA against TP53, dominant negative TP53, or an shRNA or an siRNA against P21.

4-3. Effects

The iPS cell inducer of the present invention can induce an iPS cell from a somatic cell.

The iPS cell inducer of the present invention can be used for producing an iPS cell from a somatic cell.

5. Direct Reprogramming Agent 5-1. Outline

A fifth aspect of the present invention relates to a direct reprogramming agent. The direct reprogramming agent of the present invention comprises, as an essential component, any of the mutant KLF protein or the peptide fragment thereof, the nucleic acid encoding the mutant KLF protein or the peptide fragment thereof, or the gene expression vector comprising the nucleic acid, of the present invention (hereinafter, collectively referred to as "the mutant KLF of the present invention"), and comprises other direct reprogramming factor(s) as an optional component. The direct reprogramming agent of the present invention can directly induce other various types of cells from a differentiated cell.

5-2. Definitions

The term "direct reprogramming (direct conversion)" herein refers to inducing, from a certain cell type, another cell type (for example, a cell type other than an iPS cell) directly. More specifically, the term refers to inducing, from a certain cell type, another cell type without undergoing an iPS cell stage, for example, inducing, from a differentiated cell, other various types of cells, such as a nerve cell, a hepatic cell, a pancreatic β cell, a cardiomyocyte, or an endothelial cell (Ieda M., Keio J Med. 2013; 62 (3): 74-82.). The direct reprogramming herein encompasses transdifferentiation.

The term "direct reprogramming factor" herein refers to a factor that can trigger direct reprogramming by being introduced alone or together with other factor(s) into a certain cell type. The direct reprogramming factor differs depending on a type of a cell subjected to direct reprogramming, and/or a type of a cell induced by direct reprogramming. For example, the following is known: MyoD, which induces direct reprogramming from a fibroblast to a muscle cell; a combination of Ascl1, Brn2, and Mytl1, which induces direct reprogramming from a fibroblast to a nerve cell; and a combination of Gata4, Mef2c, and Tbx5, a combination of Gata4, Mef2c, Tbx5, and Hand2, a combination of Gata4, Mef2c, Tbx5, and VEGF, or a combination of Mef2c, Myocardin, and Tbx5, which induce direct reprogramming from a fibroblast to a cardiomyocyte. In particular, specific examples of direct reprogramming where KLF4 is included as the direct reprogramming factor include: a combination of PAX6, OVOL2, and KLF4, which induces direct reprogramming from a fibroblast to a corneal epithelial cell; a combination of SOX2, KLF4, C-MYC, and POU3F4 (BRN4), which induces direct reprogramming from a fibroblast to a neural stem cell; a combination of KLF4, C-MYC, and SOX9, which induces direct reprogramming from a dermal fibroblast to a chondrocyte; and a combination of OCT3/4, SOX2, KLF4, and C-MYC, which induces direct reprogramming from a fibroblast to an endothelial cell by partial reprogramming for 4 days (Kitazawa K., et al., Cornea, 2019 November; 38 Suppl 1: S34-S41.; Kim S. M., et al., Nat Protoc., 2014 April; 9 (4): 871-81.; Outani H., et al., PLoS One, 2013 Oct. 16; 8 (10): e77365.; Margariti A, et al., Proc Natl Acad Sci USA., 2012; 109 (34): 13793-13798.).

5-3. Constitution

The direct reprogramming agent of the present invention comprises, as an essential component, the mutant KLF of the present invention. More specifically, it comprises, as an essential component, any of the mutant KLF protein or the peptide fragment thereof of the first aspect, the nucleic acid of the second aspect, or the gene expression vector of the third aspect.

The direct reprogramming agent of the present invention may further comprise one or more other direct reprogramming factor(s), as optional component(s). The other direct reprogramming factor(s) comprised in the direct reprogramming agent of the present invention is/are varied depending on a cell type subjected to direct reprogramming and/or a cell type induced by direct reprogramming, and can be appropriately selected by those skilled in the art. Examples include, but are not limited thereto, OCT3/4, SOX2, C-MYC, PAX6, VOL2, POU3F4 (BRN4), and SOX9. The other direct reprogramming factor(s) comprised in the direct reprogramming agent of the present invention may be any of a protein corresponding to the other direct reprogramming factor(s), or a peptide fragment thereof, a nucleic acid encoding the protein or the peptide fragment thereof, or a gene expression vector comprising the nucleic acid in an expressible state. Constitutions of the nucleic acid encoding the protein corresponding to the other direct reprogramming factor(s) or the peptide fragment thereof, and the gene expression vector comprising the nucleic acid in an expressible state are according to the descriptions of the second aspect and third aspect described with respect to the mutant KLF protein.

The number of the other direct reprogramming factor(s) comprised in the direct reprogramming agent of the present invention is not limited. For example, the direct reprogramming agent of the present invention may comprise one, two, three, four, five, six, or more other direct reprogramming factor(s).

When the direct reprogramming agent of the present invention comprises two or more gene expression vectors, the two or more gene expression vectors may be comprised in the same vector or may be separate vectors.

In one embodiment, the direct reprogramming agent of the present invention comprises OCT3/4, SOX2, and C-MYC, in addition to the mutant KLF of the present invention.

In another embodiment, the direct reprogramming agent of the present invention comprises PAX6, and OVOL2, in addition to the mutant KLF of the present invention.

In another embodiment, the direct reprogramming agent of the present invention comprises SOX2, C-MYC, and POU3F4 (BRN4), in addition to the mutant KLF of the present invention.

In another embodiment, the direct reprogramming agent of the present invention comprises C-MYC and SOX9, in addition to the mutant KLF of the present invention.

5-4. Effects

When the direct reprogramming agent of the present invention comprises the mutant KLF, OCT3/4, SOX2, and C-MYC, for example, partial reprogramming for 4 days by the direct reprogramming agent of the present invention induces direct reprogramming from a fibroblast to an endothelial cell at a high efficiency.

When the direct reprogramming agent of the present invention comprises the mutant KLF, PAX6, and OVOL2, direct reprogramming from a fibroblast to a corneal epithelial cell is induced at a high efficiency by the direct reprogramming agent of the present invention.

When the direct reprogramming agent of the present invention comprises the mutant KLF, SOX2, C-MYC, and POU3F4 (BRN4), direct reprogramming from a fibroblast to a neural stem cell is induced at a high efficiency by the direct reprogramming agent of the present invention.

When the direct reprogramming agent of the present invention comprises the mutant KLF, C-MYC, and SOX9, direct reprogramming from a dermal fibroblast to a chondrocyte is induced at a high efficiency by the direct reprogramming agent of the present invention.

According to the direct reprogramming agent of the present invention, direct reprogramming from a somatic cell can be performed in vitro or in vivo.

According to the direct reprogramming agent of the present invention, another cell type can be induced without undergoing a pluripotent stem cell stage. Thus, a cell reprogramming technique having a decreased cancerization risk and higher safety is provided.

6. iPS Cell Production Method 6-1. Outline

A sixth aspect of the present invention relates to an iPS cell production method. The iPS cell production method of the present invention comprises, as essential steps, (1) an introduction step of introducing an iPS cell inducer into a somatic cell(s), and (2) a cultivation step of cultivating the somatic cell(s) after the introduction step. According to the iPS cell production method of the present invention, an iPS cell can be produced at a high efficiency.

6-2. Method

The iPS cell production method of the present invention comprises, as essential steps, (1) an introduction step of introducing an iPS cell inducer into a somatic cell, and (2) a cultivation step of cultivating the somatic cell after the introduction step, and as an optional step, (3) an iPS cell selection step.

Each of the introduction step and the cultivation step is varied between "6-2-1. Embodiment using C-MYC or C-MYC-associated factor" and "6-2-2. Embodiment without C-MYC or C-MYC-associated factor" described below. The term "C-MYC-associated factor" herein refers to a factor which has a structure similar to C-MYC and can reprogram a somatic cell by being introduced instead of C-MYC, together with other reprogramming factors, into the somatic cell (hereinafter, the same also applies to "OCT3/4-associated factor" and "SOX2-associated factor"). Specific examples of each associated factor are as mentioned in "1-2. Definitions".

Hereinafter, each step in the above two cases will be specifically described.

6-2-1. Embodiment Using C-MYC or C-MYC-Associated Factor

In the introduction step of the iPS cell production method of the present embodiment, C-MYC or a C-MYC-associated factor is introduced into a somatic cell.

(1) Introduction Step

Combinations that can induce reprogramming of a somatic cell, among combinations of reprogramming factors constituting the iPS cell inducer of the fourth aspect, correspond to the iPS cell inducer to be introduced into a somatic cell in the introduction step in the present embodiment. The iPS cell inducer to be introduced into a somatic cell in the present embodiment may be, for example, a combination of the following factors (a) to (d): (a) any of the mutant KLF protein or the peptide fragment thereof of the first aspect, the nucleic acid of the second aspect, or the gene expression vector of the third aspect (hereinafter, collectively referred to as "the mutant KLF of the present invention"), (b) OCT3/4 or a OCT3/4-associated factor, (c) SOX2 or a SOX2-associated factor, and (d) C-MYC or a C-MYC-associated factor.

The iPS cell inducer to be introduced into a somatic cell in the present introduction step may comprise a reprogramming cofactor that can increase a production efficiency of an iPS cell, in addition to the above combination of reprogramming factors. The reprogramming cofactor is according to the description of "(2) Reprogramming cofactor" in "4-2-2. Optionalcomponent(s)".

The method for introducing the iPS cell inducer into a somatic cell in the present introduction step is not limited. The introduction method may be appropriately selected depending on a type of the iPS cell inducer to be introduced (plasmid DNA, mRNA, protein, viral vector, and the like). The iPS cell inducer can be introduced into a somatic cell by, for example, viral infection, a lipofection method, a liposome method, an electroporation method, a calcium phosphate method, a DEAE-Dextran method, a microinjection method, or an electroporation method. In addition, gene introduction method (transformation method) known in the art, described in Green & Sambrook, 2012, Molecular Cloning: A Laboratory Manual Fourth Ed., Cold Spring Harbor Laboratory Press, Cold Spring Harbor, New York, can be used.

(2) Cultivation Step

The cultivation step in the present embodiment is a step of cultivating the somatic cell after the introduction step. In the present cultivation step, reprogramming of a somatic cell is induced by the reprogramming factors introduced in the introduction step, and an iPS cell is induced. Furthermore, in the present step, whether or not an iPS cell is produced can be determined by observing colony formation from the iPS cell induced.

The cultivation method in the present cultivation step is not limited. For example, the somatic cell after the introduction step may be cultivated using a feeder cell. Specific examples include: a method comprising cultivating the somatic cell after the introduction step together with a feeder cells in a cell cultivation medium; and a method comprising maintaining the somatic cell after the introduction step in a cell cultivation medium for 30 days to 40 days and then cultivating it together with a feeder cell.

The feeder cell is not limited and, for example, a cell (for example, a mouse fetus fibroblast (MEF), a human fetus-derived cell, or a fibroblast), proliferation of which is stopped by radiation or antibiotic treatment, may be used.

When no feeder cell is used, a method using a culture dish covered with, for example, a basement membrane matrix, laminin, or vitronectin, or a method using a medium containing, for example, a basement membrane matrix, laminin, or vitronectin can be used.

A known medium can be appropriately selected and then used as the cell cultivation medium. For example, a commercially available basal medium for mammalian cells, to which serum or a serum replacement is added, such as DMEM, may be used. For example, KnockOut (trademark) Serum Replacement: KSR (ThermoFisher, SCIENTIFIC) may be used as the serum replacement. For example, a commercially available medium for primate ES cells or primate ES/iPS cells may be used. To such a medium may be added any known additive suitable for cultivation of pluripotent stem cells such as ES cells or iPS cells, for example, additive(s) such as an N2 supplement, a B27 (R) supplement, insulin, bFGF, activin A, heparin, a ROCK (Rho-associated coiled-coil forming kinase/Rho-binding kinase) inhibitor, and/or a GSK-3 inhibitor.

For the purpose of increasing a production efficiency of an iPS cell, for example, TGF-β, a histone deacetylase (HDAC) inhibitor, a G9a histone methyltransferase inhibitor, and/or a p53 inhibitor may be added to the medium in the introduction step of (1) above and/or the present cultivation step. As the HDAC inhibitor, for example, a low molecular inhibitor such as valproic acid (VPA), trichostatin A, sodium butyrate, MC 1293, or M344, or an siRNA against HDAC can be used, and as the G9a histone methyltransferase inhibitor, for example, a low molecular inhibitor such as BIX-01294, or an siRNA against G9a can be used, and as the p53 inhibitor, for example, a low molecular inhibitor such as Pifithrin-α, or an siRNA against p53 can be used.

Cultivation conditions such as temperature, concentration of $CO_2$, a cultivation period, and frequency of medium exchange are not limited in the present cultivation step. For example, stationary cultivation may be performed under 5% $CO_2$ at 37° C., half of the medium may be exchanged every two days, and cultivation may be performed for 10 to 40 days depending on the state of colony formation.

(3) iPS Cell Selection Step

In the iPS cell production method of the present embodiment, the iPS cell induced after the introduction step and the cultivation step may be selected.

The method for selecting the iPS cell is not limited in the present step. Examples include: a selection method using iPS cell marker gene expression as an indicator; a selection method with a selection marker gene; or a selection method with a reporter gene. The term "iPS cell marker gene" is a gene that is expressed in an iPS cell but not in a somatic cell to be reprogrammed. It is preferably a gene that is expressed specifically in an iPS cell. Examples include an Oct3/4, Sox2, Nanog, ERas, Esg1, TRA1-60, or TRA-1-85 gene, and an endogenous alkaline phosphatase gene. Examples of the method for detecting expression of the iPS cell marker gene include mRNA detection methods and immunological detection methods (for example, immunostaining method, western blot method, and ELISA method). The selection marker gene and the reporter gene are according to the description of "3-2-4. Other optional component(s) in "3. Gene expression vector". In other words, it is possible to select an iPS cell by selection using a drug corresponding to the selection marker gene (for example, a drug-resistant gene such as an ampicillin-resistant gene, a kanamycin-resistant gene, a tetracycline-resistant gene, a chloramphenicol-resistant gene, a neomycin-resistant gene, a puromycin-resistant gene, or a hygromycin-resistant gene) comprised in the gene expression vector introduced in the introduction step, or detection of a reporter depending on the reporter gene (for example, a gene encoding a fluorescent protein such as GFP or RFP, or a luciferase gene) comprised in the gene expression vector introduced in the introduction step.

6-2-2. Embodiment without C-MYC or C-MYC-Associated Factor

In the iPS cell production method of the present embodiment, C-MYC or C-MYC-associated factor is not introduced into a somatic cell in the introduction step and a reprogramming alternative factor is used in the cultivation step. The term "reprogramming alternative factor" herein means a factor that can trigger reprogramming when used instead of the reprogramming factor as described in "1-2. Definitions". In the present embodiment, the reprogramming alternative factor is a reprogramming alternative factor such that reprogramming of a somatic cell can be induced by adding the reprogramming alternative factor into a medium and performing cultivation, instead of introducing C-MYC or a C-MYC-associated factor into the somatic cell. Examples include, but not limited thereto, a basic fibroblast growth factor (bFGF), a TGF-β1 protein, a BMP protein, a Wnt3 protein, a GSK3β inhibitor, a Wnt inhibitor, retinoic acid, ascorbic acid, and a ROCK inhibitor.

(1) Introduction Step

Above combinations of reprogramming factors in "(1) Introduction step" in "6-2-1. Embodiment using C-MYC or C-MYC-associated factor" from which C-MYC or a C-MYC-associated factor is excluded, correspond to the iPS cell inducer to be introduced into a somatic cell in the introduction step in the present embodiment. Examples of the iPS cell inducer to be introduced into a somatic cell in the present embodiment include, but are not limited thereto, a combination of the following factors (a) to (c): (a) mutant KLF, (b) OCT3/4 or an OCT3/4-associated factor, and (c) SOX2 or a SOX2-associated factor.

Other conditions of the present introduction step are according to the description of "(1) Introduction step" in "6-2-1. Embodiment using C-MYC or C-MYC-associated factor" described above.

(2) Cultivation Step

The cultivation step in the present embodiment is a step of cultivating the somatic cell after the introduction step.

In the cultivation step in the present embodiment, the reprogramming alternative factor is added to a medium.

Other cultivation conditions in the present cultivation step are according to the description of "(2) Cultivation step" in "6-2-1. Embodiment using C-MYC or C-MYC-associated factor".

(3) iPS Cell Selection Step

The iPS cell selection step in the present embodiment is according to the description of "(3) iPS cell selection step" in "6-2-1. Embodiment using C-MYC or C-MYC-associated factor".

6-3. Effects

According to the iPS cell production method of the present invention, an iPS cell can be produced at a high efficiency.

According to "6-2-2. Embodiment without C-MYC or C-MYC-associated factor" in the present aspect, C-MYC or a C-MYC-associated factor being an oncogene is not introduced into a somatic cell, and thus an iPS cell production method having decreased cancerization risk and higher safety is provided. In a conventional method using wild-type KLF, such method is known to lead to an extremely low production efficiency of an iPS cell. On the contrary, in the present embodiment, a production efficiency of an iPS cell can be improved by using the mutant KLF of the present invention, and an iPS cell production method is provided in which both safety and a production efficiency are high.

The present invention also provides a method for producing iPS cells having high homogeneity and a method for producing an iPS cell having low differentiation resistance.

7. Cancer Therapeutic Agent 7-1. Outline

A seventh aspect of the present invention relates to a cancer therapeutic agent. The cancer therapeutic agent of the present invention comprises, as an active ingredient, any of the mutant KLF protein or the peptide fragment thereof of the first aspect, the nucleic acid of the second aspect, or the gene expression vector of the third aspect (hereinafter, collectively referred to as "the mutant KLF of the present invention"). The cancer therapeutic agent of the present invention has a cancer therapeutic effect.

Regarding the cancer therapeutic effect of KLF4, it has been shown that survival, invasion, and migration of papillary thyroid cancer is suppressed by KLF4 overexpression, KLF4 suppresses progression of prostate tumors, and chemotherapy resistance of colorectal cancer can be suppressed by KLF4 overexpression (Wang Q., et al., Exp Ther Med., 2019 Nov.; 18 (5): 3493-3501.; Oncogene. 2019 July; 38 (29): 5766-5777.; Yadav S. S., et al., Life Sci., 2019 Mar. 1; 220: 169-176.).

7-2. Constitution

The cancer therapeutic agent of the present invention comprises an active ingredient as an essential constituent ingredient, and a pharmaceutically acceptable carrier or other drug(s) as an optional ingredient. The cancer therapeutic agent of the present invention can also be constituted by only an active ingredient. However, preferably, it is constituted as a pharmaceutical composition comprising a pharmaceutically acceptable carrier mentioned below in order to facilitate dosage form formation and maintain a pharmacological effect and/or a dosage form of an active ingredient.

7-2-1. Constituent Ingredient

Each ingredient constituting the cancer therapeutic agent of the present invention is specifically described.

(1) Active Ingredient

The active ingredient in the cancer therapeutic agent of the present invention is the mutant KLF of the present invention. Constitutions thereof are described in detail in the first to third aspects, and thus specific descriptions thereof are omitted here. In the present aspect, the active ingredient is preferably mutant KLF4 among the mutant KLF of the present invention.

(2) Pharmaceutically Acceptable Carrier

The "pharmaceutically acceptable carrier" refers to a solvent and/or an additive that can be used usually in the formulation technique field and has almost no or no harmful effect on living organisms.

Examples of the pharmaceutically acceptable solvent include water, ethanol, propylene glycol, ethoxylated isostearyl alcohol, polyoxylated isostearyl alcohol, and polyoxyethylene sorbitan fatty acid esters. Such a solvent is desirably sterilized, and is preferably adjusted so as to be isotonic to blood, if necessary.

Examples of the pharmaceutically acceptable additive include an excipient, a binder, a disintegrant, a filler, an emulsifier, a fluidity additive modifier, and a lubricant.

Examples of the excipient include sugar, for example, monosaccharides, disaccharides, cyclodextrin and polysaccharides (more specifically including, but not limited thereto, glucose, sucrose, lactose, raffinose, mannitol, sorbitol, inositol, dextrin, maltodextrin, starch and cellulose), metal salts (for example, sodium chloride, sodium phosphate or calcium phosphate, calcium sulfate, magnesium sulfate, and calcium carbonate), citric acid, tartaric acid, glycine, low, medium or high molecular weight polyethylene glycol (PEG), Pluronic (registered trademark), kaolin, silicic acid, or combinations thereof.

Examples of the binder include starch glue using corn, wheat, rice, or potato starch, simple syrup, a glucose liquid, gelatin, tragacanth, methylcellulose, hydroxypropyl methylcellulose, carboxymethylcellulose sodium, shellac and/or polyvinylpyrrolidone.

Examples of the disintegrant include the starch, and lactose, carboxymethyl starch, crosslinked polyvinylpyrrolidone, agar, a laminaran powder, sodium hydrogen carbonate, calcium carbonate, alginic acid or sodium alginate, polyoxyethylene sorbitan fatty acid ester, sodium lauryl sulfate, stearic acid monoglyceride or any salt thereof.

Examples of the filler include the sugar and/or calcium phosphate (for example, tricalcium phosphate or calcium hydrogen phosphate).

Examples of the emulsifier include sorbitan fatty acid ester, glycerin fatty acid ester, sucrose fatty acid ester, and propylene glycol fatty acid ester.

Examples of the fluidity additive modifier and the lubricant include a silicic acid salt, talc, a stearic acid salt, or polyethylene glycol.

In addition to the above additives, if necessary, for example, a corrigent, a solubilizing auxiliary (solubilizer), a suspending agent, a diluent, a surfactant, a stabilizer, an absorption promoter (for example, quaternary ammonium salts and/or sodium lauryl sulfate), a bulking agent, a moisturizing agent (for example, glycerin and/or starch), an adsorbent (for example, starch, lactose, kaolin, bentonite, and/or colloidal silicic acid), a disintegration inhibitor (for example, saccharose, stearin, cacao butter, and/or hydrogenated oil), a coating agent, a colorant, a preservative, an antioxidant, a fragrance, a flavoring agent, a sweetener, and/or a buffer can be comprised.

(3) Other Drug(s)

The cancer therapeutic agent of the present invention can contain other drug(s) as long as the pharmacological effect of the above active ingredient is not impaired. Examples of such "other drug(s)" here include a drug having a cancer therapeutic effect by the same mechanism as the mutant KLF of the present invention, and a drug having a cancer therapeutic effect by a mechanism different from the mutant KLF of the present invention. The drug may have a pharmacological function irrelevant to a cancer therapeutic effect. Examples include a gastric mucosal protective agent and an antibiotic.

The cancer therapeutic agent of the present invention is convenient, when it is a combination formulation comprising the other drug(s), because a synergistic effect (for example, an effect of multilaterally suppressing cancers) can be expected.

7-2-2. Dosage Form

A dosage form of the cancer therapeutic agent of the present invention is not particularly limited as long as it does not deactivate or hardly deactivate the mutant KLF of the present invention being an active ingredient and a pharmacological effect can be exerted sufficiently in vivo after administration.

A dosage form can be classified by its form, into a liquid dosage form or a solid dosage form (including a semi-solid dosage form like a gel), and the dosage form of the cancer therapeutic agent of the present invention may be any of these forms. A dosage form can also be roughly classified by an administration method thereof, into an oral dosage form and a parenteral dosage form, and the dosage form of the present invention may also be any of these forms.

Specific examples of the dosage form include, as an oral dosage form, liquid dosage forms such as suspending agents, emulsions, and syrups, and solid dosage forms such as powdered drugs (including dust formulations, powdered medicines, and powdered syrup solid), granules, tablets, capsules, sublingual formulations, and troches. Specific examples of the dosage form include, as a parenteral dosage form, liquid dosage forms such as injection preparations, suspending agents, emulsions, eye drops, and nasal drops, and solid dosage forms such as creams, ointments, plasters, patches, and suppositories. The dosage form is preferably any of the oral dosage forms, or, in the case of a parenteral dosage form, an injection preparation of a liquid dosage form.

7-2-3. Administration Method

The cancer therapeutic agent of the present invention can be applied to any method known in the art as long as an effective amount of the mutant KLF of the present invention being an active ingredient can be administered to a living body for the purpose of treating a cancer in the method.

The term "effective amount" herein refers to an amount necessary for an active ingredient to exert its function (namely, an amount necessary for the cancer therapeutic agent to treat a cancer in the present invention) that has almost no or no adverse effect on a living body to which the agent is applied. The effective amount can be varied depending on conditions, for example, an information on a subject, a route of administration, and the number of administration. The "subject" refers to an animal individual to which the cancer therapeutic agent of the present invention is to be applied. The subject is preferably a human. The term "information on a subject" means various individual information on the subject, including, for example, age, body weight, sex, general health conditions, drug sensitivity, and the presence or absence of current medication of the subject. The effective amount, and a dose calculated based thereon are determined by a physician's or veterinarian's discretion according to the information on the individual subject, and the like. When a large amount of the cancer therapeutic agent of the present invention is required to be administered in order to obtain a sufficient effect of treating a cancer, the cancer therapeutic agent can also be administered in several divided doses in order to reduce a burden on the subject.

The method for administering the cancer therapeutic agent of the present invention may be systemic administration or local administration. Examples of the systemic administration include intravascular injection such as intravenous injection, and oral administration. Examples of the local administration include local injection. The active ingredient of the cancer therapeutic agent of the present invention is constituted from the mutant KLF of the present invention. Accordingly, in the case of the oral administration, it is preferable to apply an appropriate treatment, for example, use of an appropriate DDS (drug delivery system) for protecting the active ingredient from degradation due to a digestive enzyme.

As one example of a specific dose, for example, the effective amount per day of the cancer therapeutic agent is usually in the range from 1 to 2000 mg, preferably 1 to 1000 mg, more preferably 1 to 500 mg, when administering it to a human adult male (body weight 60 kg) suffering from a cancer. When the cancer therapeutic agent of the present invention is administered to the subject, the effective dose of the mutant KLF of the present invention is selected in the range of 0.001 mg to 1000 mg/kg body weight per dose. Alternatively, a dose of 0.01 to 100000 mg/body per subject can be selected. However, the dose is not limited thereto.

7-3. Effects

The cancer therapeutic agent of the present invention has a cancer therapeutic effect. The cancer therapeutic agent of the present invention has a therapeutic effect on, for example, papillary thyroid cancer, prostate tumor, and colorectal cancer. More specifically, it is possible to suppress survival, invasion, and migration of papillary thyroid cancer at high efficiencies, suppress progression of prostate tumors at a high efficiency, and efficiently suppress chemotherapy resistance of colorectal cancer at a high efficiency.

EXAMPLES

Example 1: Search and Identification of KLF4
Mutant Efficiently Inducing Reprogramming of
Somatic Cells at a High Efficiency (Object)

A mutation will be introduced into an amino acid residue capable of directly interacting with DNA to a wild-type KLF4 protein, and a KLF4 mutant inducing reprogramming of somatic cells at a high efficiency will be identified.

(Method)

Nine complex structures of KLF4 protein C2H2 zinc finger domains (KLF4ZFD) and DNA are registered in the Protein Data Bank (PDB), a database of steric structures of proteins (registry numbers: 2WBS, 2WBU, 4M9E, 5KE6, 5KE7, 5KE8, 5KE9, 5KEA, and 5KEB). In such crystal structures, nineteen amino acid residues directly interacting with DNA were identified (FIG. 1).

Next, 19 retroviral vectors for expressing a KLF4 mutant were produced, wherein the KLF4 mutant was derived from a human wild-type KLF4 protein having the amino acid sequence represented by SEQ ID NO: 5 by substituting one of the 19 amino acid residues with alanine. Furthermore, retroviral vectors for expressing human wild-type OCT3/4 having the amino acid sequence represented by SEQ ID NO: 13, human wild-type SOX2 having the amino acid sequence represented by SEQ ID NO: 15, and human wild-type L-MYC having the amino acid sequence represented by SEQ ID NO: 21, respectively, were prepared.

Specifically, a 3×FLAG tag for detecting protein expression was fused to the N-terminal side of KLF4 in pMXs-hKLF4 (Addgene plasmid #17219), and the resulting was used as a template for a site-specific mutagenesis method. SEQ ID NOs: 26 to 27 each exhibits the sequence of a primer used when adding the 3×FLAG tag at the N-terminal. For the site-specific mutagenesis, PrimeSTAR Max DNA Polymerase (TAKARA BIO INC) and PrimeSTAR Mutagenesis Basal Kit (TAKARA BIO INC) were used according to the supplier's protocol of PCR Thermal Cycler (Applied Biosystems SimpliAmp). A specific primer pair for use in the site-specific mutagenesis was designed so that 15 bp regions comprising a substitution site were overlapped with each other. PCR conditions were as follows: 98° C. for 10 seconds (denature), 55° C. for 15 seconds (annealing), and 72° C. for 30 seconds (elongation). The sequences after the mutagenesis were confirmed by sequencing using a pMX-s1811 (FW) primer and a pMX-as3205 (RV) primer.

The retroviral vectors were prepared by the following method. Plat-E cells (Cell Biolab INC, RV-101) were seeded at $3.6×10^6$ cells per 100-mm dish or at $5.4×10^5$ cells per well on a 6-well plate. On the next day, in the case of the 100-mm dish, each pMX-based retroviral vector (9 µg) for expressing human OCT4 (Addgene plasmid #17217), human SOX2 (Addgene plasmid #17218), human L-MYC (Addgene plasmid #26022), human wild-type KLF4 (pMXs-hKLF4, Addgene plasmid #17219), or KLF4 mutant was separately introduced into Plat-E cells using 27 µl of a FuGENE 6 transfection reagent (Promega INC, E2691). In the case of the 6-well plate, 4.5 µl of a FuGENE 6 transfection reagent and 1.5 µg of each of the retroviral vectors were used. After 24 hours, the medium was exchanged with 10 ml of DMEM comprising 10% FBS (Biosera, FB-1365/500) and P/S (Nacalai Tesque, Inc., 26253-84), and the cells were incubated for additional 24 hours. A retrovirus-containing supernatant was collected two times after 48 hours and after 72 hours of lipofection, and filtered by a cellulose acetate filter (AS ONE Corporation, RJN1345NH) having a pore size of 0.45 µm. 0.5 ml each of the supernatants were mixed at equal volumes (ratio 1:1:1:1), and Polybrene (Nacalai Tesque, Inc., 12996-81) was added at a final concentration of 4 µg/ml for cell infection.

Next, mouse fetal fibroblasts were infected with the retroviral vectors, and reprogramming induction was performed. The mouse fetal fibroblasts here used were those isolated from Nanog-GFP mouse (Experimental Animal Division/RIKEN BioResource Research Center, STOCK Tg (Nanog-GFP, Puro) 1Yam, deposit No. RBRCO2290) by a known method. The Nanog-GFP mouse fetal fibroblasts were infected with the retroviral vectors by subjecting 100,000 to 200,000 Nanog-GFP mouse fetal fibroblasts small in passage number to infection in a 6-well dish. The Nanog-GFP mouse fetal fibroblasts were incubated together with the retroviral vectors prepared above, for 24 hours, and then returned to a high glucose DMEM (Nacalai Tesque, Inc., 08458-16)) to which a usual fibroblast culture medium (10% FBS (Biosera, FB-1365/500), P/S (Nacalai Tesque, Inc., 26253-84)) was added. The medium was exchanged at a frequency of every two days. Furthermore, 10,000 cells were re-seeded on SL10 feeder cells (REPROCELL USA Inc) on day 6, and, on the next day, the medium was exchanged with an mES complete medium (high glucose DMEM (Nacalai Tesque, Inc., 08458-16) to which 15% FBS (Biosera, FB-1365/500), a MEM non-essential amino acid solution (Nacalai Tesque, Inc., 06344-56), LIF (FUJIFILM Wako Pure Chemical Corporation, 129-05601), and P/S (Nacalai Tesque, Inc., 26253-84) were added). The medium was exchanged at a frequency of every two days and the cells were cultivated for 25 days.

(Results)

The number of colonies exhibiting green fluorescence derived from Nanog-GFP (iPS cell marker) was measured on day 25 of retroviral vector infection.

Figure 2:
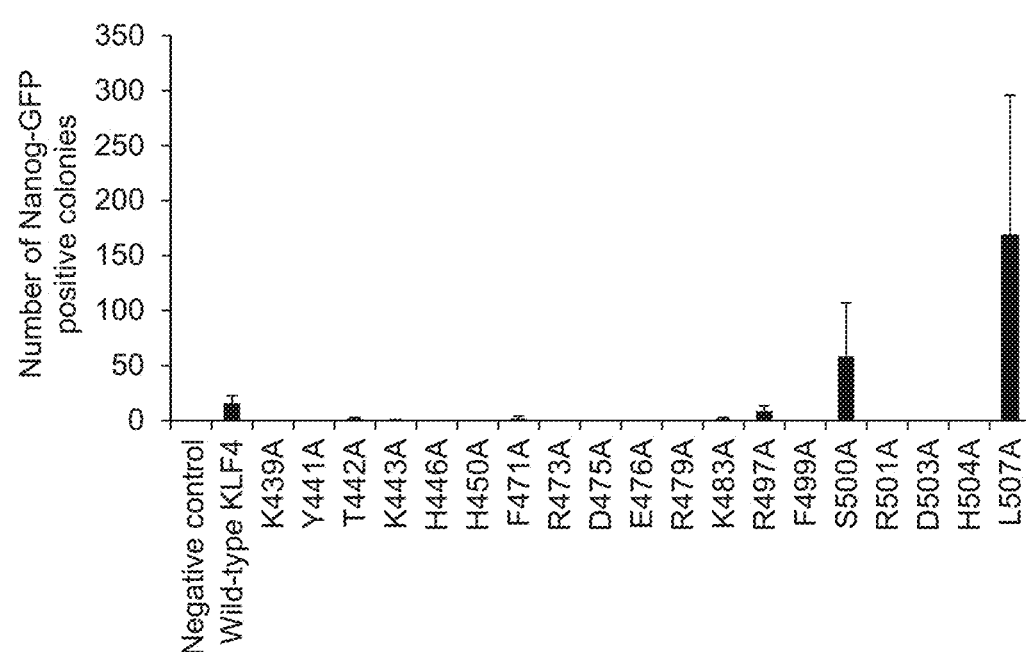
FIG. 2 illustrates the results of reprogramming induction using mutant KLF4 proteins in which each of the 19 amino acid residues capable of directly interacting with DNA is substituted with alanine. The reprogramming induction was performed by introducing the mutant KLF4 protein, together with other reprogramming factors (OCT3/4, SOX2, and L-MYC), into Nanog-GFP mouse fetal fibroblasts using retroviral vectors. (A) illustrates the number of Nanog-GFP positive colonies on day 25 after viral infection, formed from 10,000 Nanog-GFP mouse fetal fibroblasts into which the reprogramming factors were introduced. (B) illustrates the proportion of the number of Nanog-GFP positive colonies to the number of all colonies on day 25 after viral infection.
Figure 2:
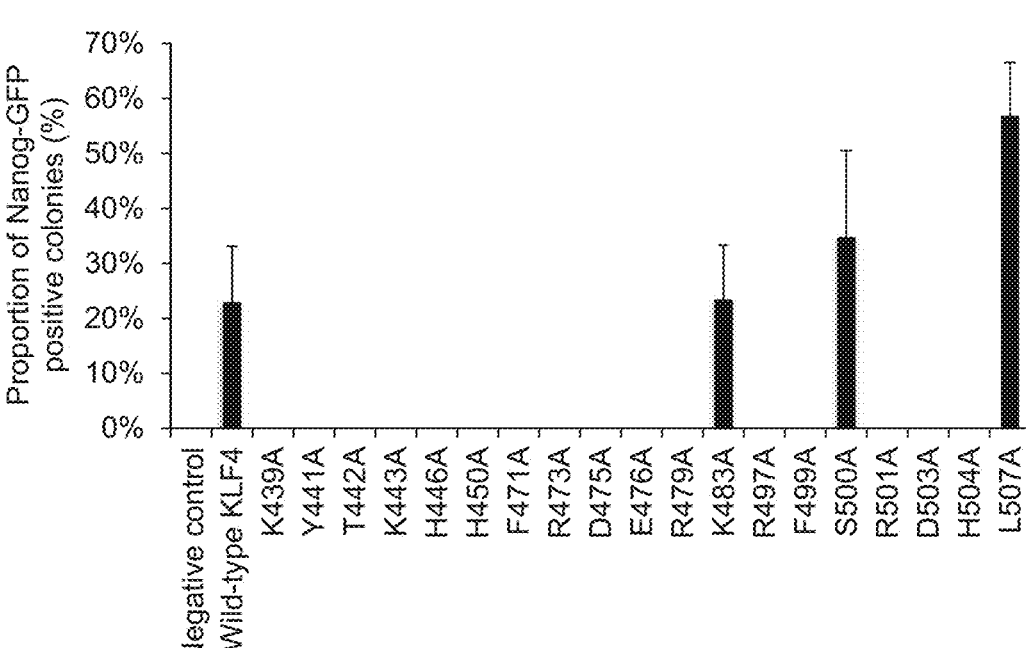

As a result, the number of Nanog-GFP positive colonies formed was reduced in most of the alanine substitution mutants, as compared with wild-type KLF4 (FIG. 2A). On the contrary, the number of Nanog-GFP positive colonies was remarkably increased in a KLF4 (S500A) mutant and a KLF4 (L507A) mutant, as compared with wild-type KLF4 (FIG. 2A). Furthermore, the proportion of Nanog-GFP positive colonies relative to the number of all colonies was increased in KLF4 (S500A) mutant and the KLF4 (L507A) mutant, as compared with wild-type KLF4 (FIG. 2B).

The increase in proportion of Nanog-GFP positive colonies indicates that proportion of fully reprogrammed iPS cells relative to partially reprogrammed iPS cells was increased. Partially reprogrammed iPS cells have low differentiation potential and pluripotency. On the contrary, fully reprogrammed iPS cells have high differentiation potential and pluripotency. Accordingly, it was demonstrated that high-quality iPS cells can be produced at a higher efficiency and an iPS cell population having high differentiation potential and higher homogeneity can be provided by using the KLF4 (S500A) mutant or KLF4 (L507A) mutant in reprogramming induction.

The amino acid identities of zinc finger domains of KLF1, KLF2, and KLF5 relative to KLF4, are extremely as high as 85%, 93%, and 81%, respectively. Furthermore, any of KLF1, KLF2, KLF4, and KLF5, when introduced together with other reprogramming factors (for example, OCT3/4, SOX2, and C-MYC) into somatic cells, has an activity of inducing reprogramming of somatic cells. Accordingly, mutant KLF1, mutant KLF2, and mutant KLF5 comprising an amino acid substitution at a position corresponding to position 500 or position 507 of KLF4 (for example, mutant KLF1 comprising L356A mutation, mutant KLF2 comprising L349A mutation, and mutant KLF5 comprising L450A mutation) are also highly likely to induce reprogramming of somatic cells at higher efficiencies than wild-type KLF1, KLF2, and KLF5, respectively.

Example 2: iPS Cell Production from Normal
Human Fibroblast Using KLF4 Mutant (Object)

Reprogramming induction will be performed using the KLF4 (L507A) mutant, on normal human fibroblasts. Expression of a pluripotent stem cell marker Tumor-related antigen-1-60 (TRA-1-60) will be analyzed by a flow cytometry method early after reprogramming induction.

The pluripotent stem cell marker TRA-1-60 is a glycoprotein specifically expressed in human iPS cells and ES cells but not expressed in somatic cells. TRA-1-60 positive human cells obtained by inducing reprogramming by four reprogramming factors (OCT3/4, SOX2, KLF4, and C-MYC) are cells being reprogrammed to high-quality iPS cells. It is known that TRA-1-60 positive cells have a gene expression profile similar to that of primitive streak-like mesendodermal (PSMN) and the PSMN-like state is important for maturation at the late stage of reprogramming (Chan E. M., et al., Nat Biotechnol. 2009 November; 27 (11): 1033-7.). Therefore, if TRA-1-60 is used as an expression marker, high-quality reprogramming cells can be detected at the ealiest time.

(Method)

Normal human fibroblasts (NB1RGB cells) were cultivated in a Dulbecco's modified eagle medium (4.5 g/L glucose, Nacalai Tesque, Inc., 08458-16) containing 10% FBS (Biosera, FB-1365/500), P/S, penicillin (100 units/ml) and streptomycin (100 μg/ml) (Nacalai Tesque, Inc., 26253-84).

Reprogramming induction of normal human fibroblasts was performed by the following method. pMX vectors containing human OCT4 (Addgene plasmid #17217), human SOX2 (Addgene plasmid #17218), human L-MYC (Addgene plasmid #26022), human wild-type KLF4 (pMXs-hKLF4, Addgene plasmid #17219) or KLF4 mutant, and a pCMV-VSV-G virus envelope vector (RDB04392, RIKEN BRC lentiviral vector plasmid) were combined at a ratio of 3:1, and transfected into Plat-GP (Cell Biolab INC, RV-103) cells using a FuGENE 6 transfection reagent. The resultant virus supernatant was used for viral infection of 10,000 NB1RGB cells small in passage number, in a 6-well dish overnight.

On day 7 after viral infection, analysis by flow cytometry was performed. The cells after the infection were washed with 1 ml of PBS, and incubated with Accutase (Nacalai Tesque, Inc., 12679-54) for about 10 minutes until the cells were detached. The cells were re-suspended in a buffer for flow cytometry (0.5% EDTA-containing PBS to which 1% fetal bovine serum was added), and incubated with an Alexa Fluor 488 mouse anti-human TRA-1-60 antibody (BD Pharmingen) and a human TRA-1-85/CD147 APC conjugate antibody (R&D systems) for 1 hour. The cells were washed and then used in flow cytometry (Guava easyCyte Flow Cytometer).

The presence or absence of TRA-1-60 expression was determined based on fluorescent brightness measured by flow cytometry. Specifically, in a case where the fluorescent brightness was higher than a measurement value in the original fibroblast population, TRA-1-60 was determined to be positive.

(Results)

Figure 3:
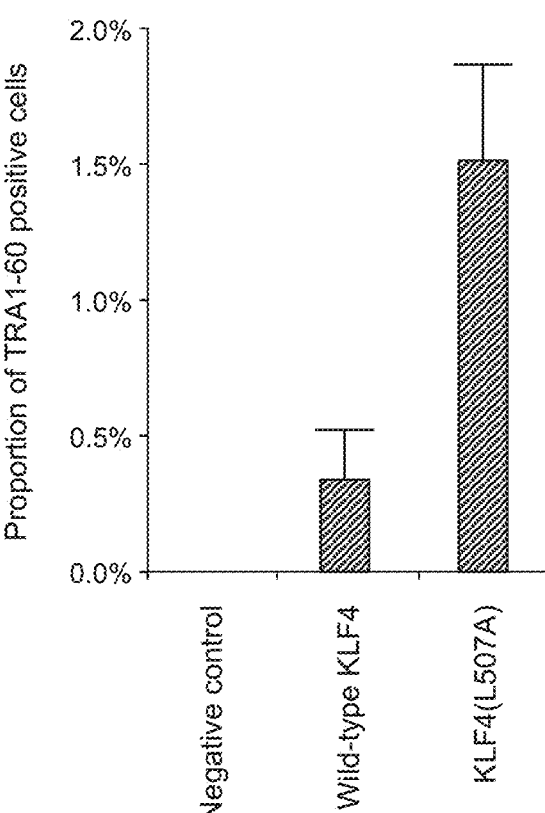
FIG. 3 illustrates the results of flow cytometry analysis of the proportion of cells expressing a pluripotent stem cell marker TRA1-60, in human fibroblasts subjected to reprogramming induction. The proportion of cells expressing a pluripotent stem cell marker TRA1-60 on day 7 after retroviral infection was measured, in a cell population obtained by reprogramming induction with a wild-type KLF4 protein or KLF4 (L507A) mutant. The "negative control" represents human fibroblasts into which no reprogramming factors were introduced. The drawing shows the average of measurement data (n=6), and each error bar represents a standard error.

From the results of flow cytometry, it was demonstrated that use of the KLF4 (L507A) mutant generated more TRA-1-60 positive cells on day 7 after infection compared to wild-type KLF4 (FIG. 3). In other words, while the positive rate of TRA1-60 expression on day 7 after infection was about 0.3% when using wild-type KLF4, the rate was about 1.5% when using the KLF4 (L507A) mutant, which was equivalent to about 5 times (FIG. 3).

From the above results, it was demonstrated that the KLF4 mutant of the present invention increases a reprogramming induction efficiency of normal human fibroblasts. It was also demonstrated that the KLF4 mutant of the present invention accelerates a reprogramming process at the initial stage of reprogramming induction.

Example 3: iPS Cell Production from Nanog-GFP Mouse Fetal Fibroblasts Using Sendai Viral Vector and KLF4 Mutant (Object)

It will be examined whether or not the KLF4 mutant of the present invention can increase a reprogramming induction efficiency even when using a replication-defective and persistent Sendai viral vector (SeVdp vector) having high safety.

(Method)

In Example 3, an expression amount of the KLF4 protein was controlled using a destabilizing domain (DD tag). In other words, stability of the KLF4 protein with the DD tag at the N-terminal side was controlled by adding low molecular ligand Shield 1 into a medium (Nishimura K., et al., Stem Cell Reports. 2014 Nov. 11; 3 (5): 915-929.). When Shield 1 is not added to the medium, the KLF4 protein with the DD tag was degraded. On the contrary, when Shield 1 is added to the medium, degradation of the KLF4 protein with the DD tag is blocked.

A SeVdp vector for introducing a KLF4 (L507A) mutant with a FLAG tag at the C-terminal side and the DD tag at the N-terminal side and other reprogramming factors (SeVdp (fK[L507A]OSM) vector) was produced, and the vector was used to perform reprogramming induction. The same experiment was performed on wild-type KLF4 and a KLF4 (K483A) mutant with a FLAG tag at the C-terminal and the DD tag at the N-terminal, and the iPS cell production efficiencies were compared. The KLF4 (K483A) mutant did not increase a reprogramming efficiency of somatic cells in Example 1, and was used as a control group in Example 3.

The SeVdp vector was used to perform viral infection of 125,000 cells/well of Nanog-GFP mouse fetal fibroblasts (MEF) at 32° C. for 24 hours, and four reprogramming factors (OCT3/4, SOX2, KLF4, and C-MYC) were introduced. On the next day of infection, a SeV-containing medium was exchanged with a fibroblast culture medium (Dulbecco's modified eagle medium (Sigma, D5796) containing 10% FBS (Gibco, 10437028) and 100 U/ml penicillin-streptomycin (Nacalai, 26253-94)) to which 100 nM Shield 1 (TAKARA BIO INC., 632189) was added (Shield 1 was added at every exchange of the medium for sustained expression of KLF4). On day 3, Blasticidin S (FUJIFILM Wako Pure Chemical Corporation, 029-18701) (final concentration 5 μg/ml) was added to the medium. Next, $1.0 \times 10^4$, $5.0 \times 10^3$, and $2.5 \times 10^3$ of infection cells were re-seeded on SL10 feeder cells in a 6-well plate on day 7. The cells were cultivated in the presence or absence of Shield 1 for 25 days in a mES medium (Sigma, D5796) to which 15% fetal bovine serum (Gibco, 10437028), 0.1 mM non-essential amino acid (Nacalai, 06344-56), 55 μM 2-mercaptoethanol (Gibco, 21985023100), 100 U/ml penicillin-streptomycin (Nacalai, 26252-94) and 1,000 U/ml LIF (Wako, 125-05603) were added, with the medium being exchanged every two days. iPS cell colonies expressing GFP were observed by a fluorescence microscope.

(Results)

Figure 4:
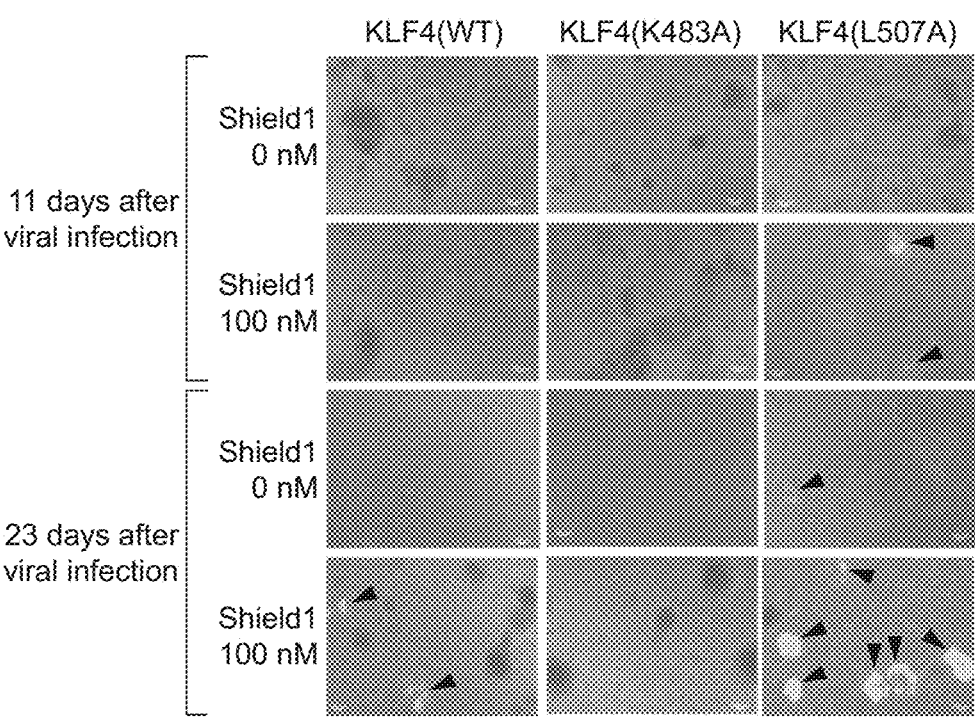
FIG. 4 illustrates the results of reprogramming induction of Nanog-GFP mouse fetal fibroblasts using a Sendai viral vector. In this experiment, a KLF4 protein is fused with a destabilizing domain (DD), and is degraded in the absence of Shield 1 (0 nM), but is not degraded in the presence of Shield 1 (100 nM). A light area indicated by an arrow head represents Nanog-GFP positive colonies.

When wild-type KLF4 was used, no Nanog-GFP positive colonies were observed at all in the presence of Shield 1 on day 11 after infection, and Nanog-GFP positive colonies emitting weak fluorescence were first observed on day 23 after infection (FIG. 4, left row, on day 23 after infection, Shield 1 100 nM, arrow head). In this case, the proportion of the number of Nanog-GFP positive colonies to the number of all colonies on day 23 after viral infection was about 10%.

When the KLF4 (K483A) mutant was used as a control group, no Nanog-GFP positive colonies were observed both on day 11 after infection and on day 23 after infection (FIG. 4, middle row).

On the other hand, when the KLF4 (L507A) mutant was used, Nanog-GFP positive colonies emitting weak fluorescence were observed from day 11 after infection in the presence of Shield 1 (FIG. 4, right row, on day 11 after infection, Shield 1 100 nM, arrow head), and many Nanog-GFP positive colonies emitting strong fluorescence were observed on day 23 after infection (FIG. 4, right row, on day 23 after infection, Shield 1 100 nM, arrow head). In this case, the proportion of the number of Nanog-GFP positive colonies to the number of all colonies on day 23 after viral infection was 50% or more, and remarkably high as compared with the case where wild-type KLF4 was used (about 10%).

When the KLF4 (L507A) mutant was used, induction of Nanog-GFP positive colonies was observed even in the absence of Shield 1 (FIG. 4, right row, on day 23 after infection, Shield 1, 0 nM, arrow head). A KLF4 protein with the DD tag is not fully degraded even in the absence of Shield 1, and about 30% thereof remains (Nishimura K., et al., Stem Cell Reports. 2014 Nov. 11; 3 (5): 915-929.). Accordingly, Nanog-GFP positive colonies induced in the absence of Shield 1 were considered to be due to the activity of the KLF4 protein remained without being degraded. On the contrary, when wild-type KLF4 was used and when the KLF4 (K483A) mutant was used, no Nanog-GFP positive colonies were observed in the absence of Shield 1 at all. Accordingly, it was demonstrated, also from the results, that the KLF4 (L507A) mutant has a remarkably high reprogramming induction activity as compared with wild-type KLF4.

From the foregoing results, it was demonstrated that the KLF4 (L507A) mutant can increase a reprogramming efficiency regardless of a gene delivery system. Particularly, it was demonstrated that the mutant can be used in combination with a SeVdp vector having high safety.

Example 4: Expectation of Substitution Mutation Stabilizing Structure of KLF4 Protein (Object)

Concerning amino acid residues after substitution when substituting leucine at position 507 in the KLF4 protein, it will be examined substitution to which amino acid residue stabilizes the protein structure.

(Method and Results)

Figure 5:
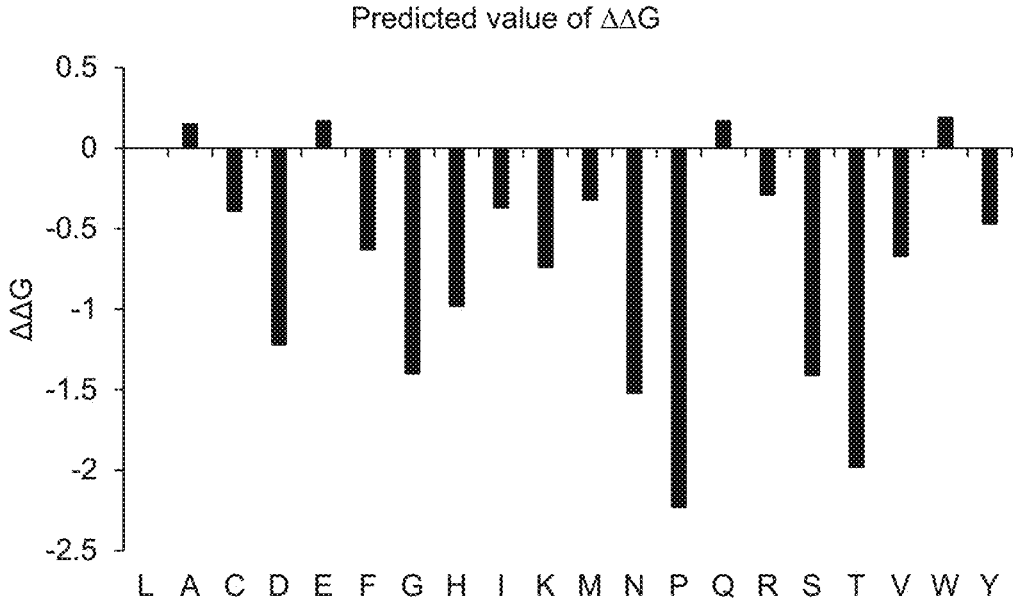
FIG. 5 illustrates the expectation results of stability of KLF4 proteins in which the leucine at position 507 is substituted with various amino acid residues. The vertical axis represents the variation in free energy ($\Delta\Delta G$) expected in the case of substituting leucine at position 507 with each amino acid residue. It is indicated that, as MG is higher, the structure of the KLF4 protein is more stable.

FIG. 5 illustrates the results of calculating a variation in free energy ($\Delta\Delta G$) when substituting leucine at position 507 (L507) in the KLF4 protein with various amino acid residues, using Site Directed Mutator (http colon forward slash forward slash marid dot bioc dot cam dot ac dot uk/sdm2/prediction) (Worth C. L., Preissner R, and Blundell T. L., Nucleic Acids Res., 2011 May 18, 39: W215-22). The obtained results expected that structure of KLF4 protein is stabilized as compared to wild-type when substituting L507 with alanine (A), glutamic acid (E), glutamine (Q), or tryptophan (W) (FIG. 5).

A KLF4 mutant having L507A mutation among the above substitutions actually increases a reprogramming induction efficiency of somatic cells, as shown in Example 1. Therefore, other amino acid substitutions expected to stabilize the KLF4 structure in the present Example (L507E, L507Q, and L507W), are also highly likely to result in an increase in a reprogramming induction efficiency of somatic cells. Similarly, L356E, L356Q, or L356W in the KLF1 protein, L349E, L349Q, or L349W in the KLF2 protein, and L450E, L450Q, or L450W in the KLF5 protein, corresponding to L507E, L507Q, or L507 in the KLF4 protein, are also highly likely to result in an increase in a reprogramming induction efficiency of somatic cells.

Example 5: iPS Cell Production from Human Fibroblast Using Sendai Viral Vector and KLF4 Mutant (Object)

iPS cells will be produced from human fibroblasts using a Sendai viral vector and a KLF4 mutant, and quality of the resulting iPS cells will be evaluated.

(Method)

Using the KLF4 (L507A) mutant and wild-type KLF4 with a FLAG tag at the C-terminal side and the DD tag at the N-terminal side produced in Example 3, four reprogramming factors (OCT3/4, SOX2, KLF4, and C-MYC) were introduced into human fibroblasts by the SeVdp vector, and iPS cells were produced under cultivation conditions using no feeder.

The SeVdp vector was used to perform viral infection of normal human fibroblasts (100,000 NB1RGB cells) in a 12-well plate at 32° C. for 24 hours. The cells after infection were cultivated in the presence or absence of 100 nM Shield 1 in a human ES cellular medium prepared from a Primate ES cell medium (Reprocell), 1× penicillin/streptomycin (Nacalai Tesque) and 10 ng/mL basic FGF (Wako). The cells were cultivated and selected in the presence of 1 μg/mL Blasticidin S (Wako) during a period from day 3 to day 5 of cultivation, and re-seeded in a 60-mm dish on day 11. Individual iPS cell colonies were cultivated in a StemFit AK02N medium (Ajinomoto) to which 10 μM Y-27632 (Wako) and 0.25 μg/cm$^2$ iMatrix-511 (Nippi) were added, and were transferred to a 24-well plate on day 22 and further transferred to a 60-mm dish on day 32. Cells for storage, prepared in STEM-CELLBANKER (Takara Bio, #CB045), were stored until mRNA analysis, and used for total RNA extraction described below.

Expressions of NANOG, Sendai virus NP (nucleocapsid protein) remaining, HERV-H, and lincRNA-RoR, in the above cells derived from individual colonies, were quantitatively determined by RT-qPCR (reverse transcription-quantitative polymerase chain reaction). HERV-H and lincRNA-RoR are known to be markers for iPS cells differentiation of which is hardly induced (differentiation resistance markers) (Ohnuki M., et al., Proc Natl Acad Sci USA. 2014; 111 (34): 12426-12431.), and iPS cells having low expression levels of differentiation resistance markers are high-quality. RT-qPCR was performed by the following method. Total RNA was extracted using Monarch Total RNA Miniprep Kit (New England BioLabs) or FastGene RNA premium kit (Nippon Genetics). Genomic DNA removal and reverse transcription were performed using ReverTra Ace qPCR RT kit (Toyobo). qPCR was performed using QuantStudio 3 Real-Time PCR System (Applied Biosystems) and using THUNDERBIRD SYBR qPCR Mix (Toyobo) or THUNDERBIRD Probe qPCR Mix (Toyobo). All qPCRs were performed at n=3.

(Results)

Figure 6:
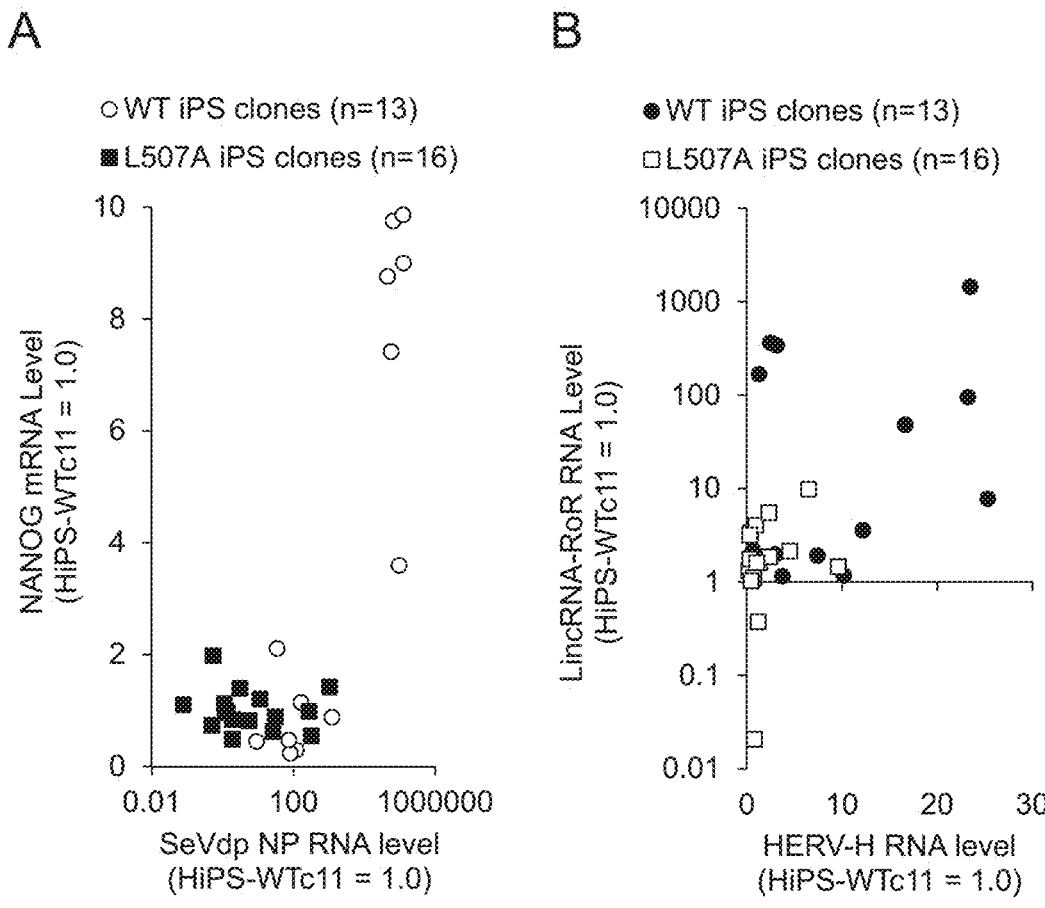
FIG. 6 illustrates the results of reprogramming induction of normal human fibroblasts using a Sendai viral vector. iPS cell clones obtained using a wild-type KLF4 protein (WT iPS clones, n=13) and iPS cell clones obtained using a KLF4 (L507A) mutant (L507A iPS clones, n=16) are compared. (A) illustrates the results of quantification by RT-qPCR, of the NANOG mRNA expression level and the Sendai virus NP mRNA expression level in each of the iPS cell clones. The expression levels are represented as a value normalized under the assumption that the expression level in a standard human iPS cell line (HiPS-WTc11) is 1.0. (B) illustrates the results of quantification by RT-qPCR, of the RNA expression levels of differentiation resistance markers, HERV-H and lincRNA-RoR in each of the iPS cell clones. The expression levels are represented as a value normalized under the assumption that the expression level in a standard human iPS cell line (HiPS-WTc11) is 1.0.

An RNA sample was recovered from individual iPS cell clones where the passage number was one. Thirteen iPS cell clones produced using wild-type KLF4 were largely varied in a NANOG expression amount from clone to clone, and some clones exhibited a NANOG expression amount less than half of that of HiPS-WTc11 (Coriell Institute, #GM25256; Kreitzer F. R., et al., Am J Stem Cells, 2013, 2 (2): 119-31.) used as a standard human iPS cell line in the art (FIG. 6A). Six clones among the thirteen clones produced using wild-type KLF4 exhibited an NP RNA amount more than 10,000 times that of a standard human iPS cell line (HiPS-WTc11), and exhibited an abnormally large NANOG expression amount.

On the contrary, sixteen iPS cell clones produced using the KLF4 (L507A) mutant exhibited an NP RNA amount less than 1000 times that of a standard human iPS cell line (HiPS-WTc11), and exhibited a relatively uniform NANOG expression amount within twice (FIG. 6A).

While some of the iPS cell clones produced using wild-type KLF4 exhibited high expression of HERV-H and/or lincRNA-RoR being a differentiation resistance marker, such clones were not observed in iPS cell clones produced using the KLF4 (L507A) mutant (FIG. 6B).

From the foregoing results, it was demonstrated that, when iPS cells are produced by introducing the KLF4 (L507A) mutant with the SeVdp vector, high-quality human iPS cell clones having high homogeneity can be stably produced, in which an amount of the remaining SeVdp vector was small and expression of a differentiation resistance marker is not abnormally high.

Example 6: Substitution of KLF4 L507 with Ala, Gln, Asp, Cys, Glu, Gly, Lys, Met, Ser, and Thr (Object)

KLF4 mutants, in which leucine at position 507 of KLF4 (KLF4 L507) is substituted with any of 10 amino acid residues including alanine, will be produced, and their effects on a reprogramming efficiency of somatic cells will be examined.

(Method and Results)

KLF4 mutants were produced, in which KLF4 L507 was substituted with any of 10 amino acids of Ala, Gln, Asp, Cys, Glu, Gly, Lys, Met, Ser, and Thr (hereinafter, designated as L507A, L507N, L507D, L507C, L507E, L507G, L507K, L507M, L507S, and L507T). For each of the substituted mutants, a retroviral vector was produced by the same method as in Example 1, and the mutant was introduced, together with OCT4, SOX2, and MCYCL1, into Nanog-GFP mouse fetal fibroblasts by the same method as in Example 1 to produce iPS cells.

Figure 7:
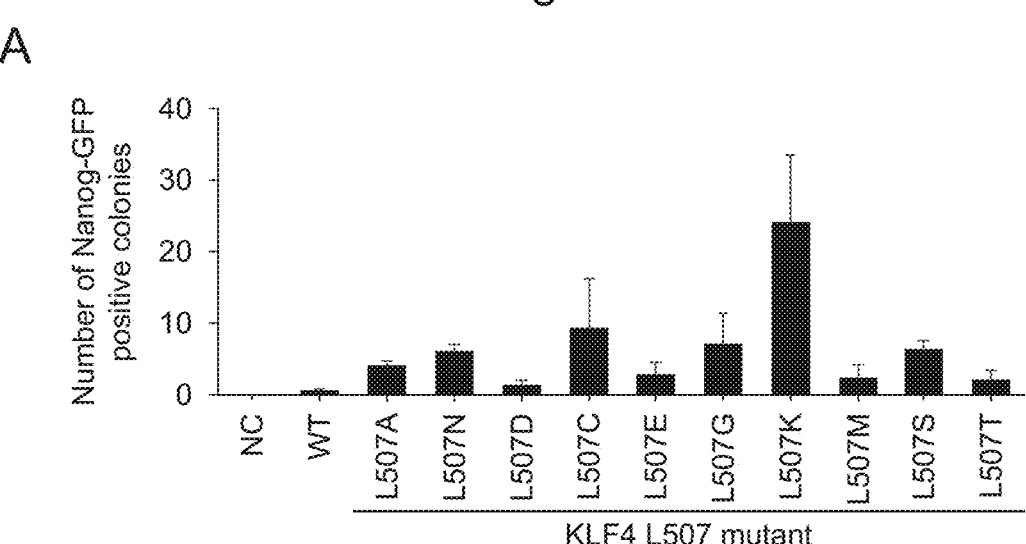
FIG. 7 illustrates the results of reprogramming induction using KLF4 mutants in which leucine at position 507 of a KLF4 protein is substituted with various amino acid residues. (A) illustrates the number of Nanog-GFP positive iPS cell colonies on day 15 after retroviral infection. (B) illustrates the number of Nanog-GFP positive iPS cell colonies on day 25 after retroviral infection. (C) illustrates the proportion of Nanog-GFP positive iPS cell colonies relative to all colonies on day 25 after retroviral infection.
Figure 7:
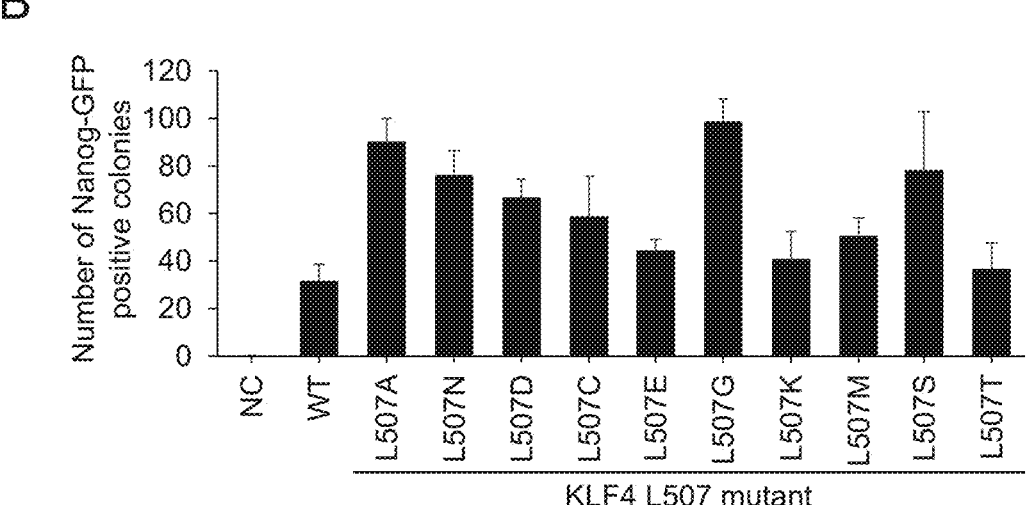
Figure 7:
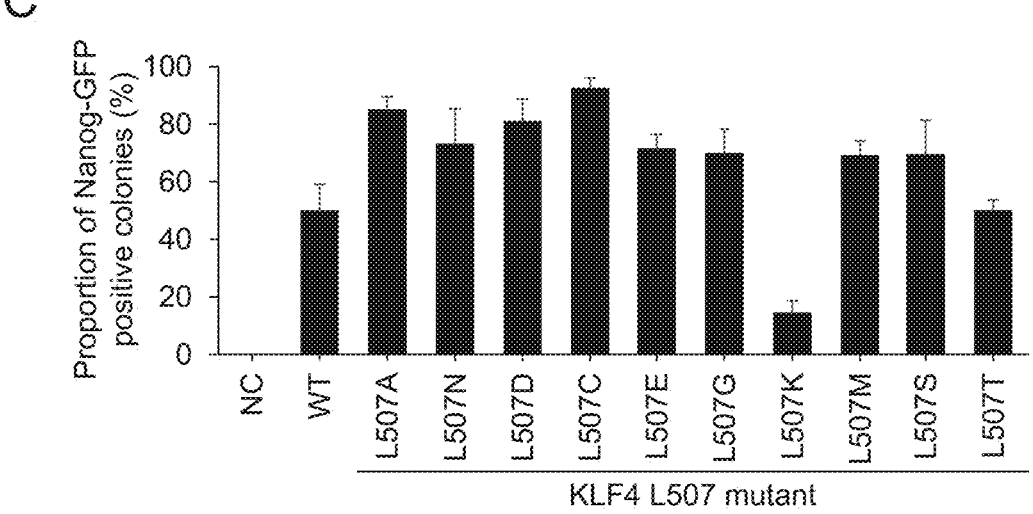

More Nanog-GFP positive iPS cell colonies were observed in L507A, L507N, L507D, L507C, L507G, L507K, L507M, and L507S at the early stage after viral infection (on day 15 after viral infection), as compared with wild-type KLF4 (FIG. 7A). From the results, it was demonstrated that a rate of reprogramming to iPS cells was improved and iPS cells were obtained earlier in L507A, L507N, L507C, L507G, L507K, and L507S. The effect was significant, particularly in L507K.

More GFP positive iPS cell colonies were observed in L507A, L507N, L507D, L507C, L507G, and L507S on day 25 after viral infection, as compared with wild-type KLF4 (FIG. 7B). The most iPS cell colonies were observed in L507G. From the results, it was demonstrated that an efficiency of reprogramming to iPS cells was improved in L507A, L507N, L507D, L507C, L507G, and L507S.

FIG. 7C illustrates the results of calculating a proportion of Nanog-GFP positive iPS cell colonies relative to all colonies on day 25 after viral infection.

From the foregoing results, it was demonstrated that both the rate of reprogramming and the efficiency of reprogramming, to iPS cells, were improved in L507A, L507N, L507D, L507C, L507G, and L507S.

All publications, patents, and patent applications cited herein are incorporated herein by reference in their entirety.

The invention claimed is:

1. A mutant Krüppel-like factor (KLF) protein comprising an amino acid substitution, wherein
   the amino acid substitution is a substitution of any of the following:
     (a) serine at position 349 and/or leucine at position 356 in the amino acid sequence set forth in SEQ ID NO: 1;
     (b) serine at position 342 and/or leucine at position 349 in the amino acid sequence set forth in SEQ ID NO: 3;
     (c) serine at position 500 and/or leucine at position 507 in the amino acid sequence set forth in SEQ ID NO: 5; or
     (d) serine at position 443 and/or leucine at position 450 in the amino acid sequence represented by SEQ ID NO: 7.

2. The mutant KLF protein according to claim 1, wherein
   the substitution of (a) is S349A, and/or L356A, L356N, L356D, L356C, L356E, L356G, L356K, L356M, L356S, or L356T,
   the substitution of (b) is S342A, and/or L349A, L349N, L349D, L349C, L349E, L349G, L349K, L349M, L349S, or L349T,
   the substitution of (c) is S500A, and/or L507A, L507N, L507D, L507C, L507E, L507G, L507K, L507M, L507S, or L507T, or
   the substitution of (d) is S443A, and/or L450A, L450N, L450D, L450C, L450E, L450G, L450K, L450M, L450S, or L450T.

3. A nucleic acid encoding the mutant KLF protein according to claim 1.

4. A gene expression vector comprising the nucleic acid according to claim 3, in an expressible state.

5. An induced pluripotent stem cell (iPS cell) inducer comprising the nucleic acid according to claim 3.

6. A direct reprogramming agent comprising the nucleic acid according to claim 3.

7. A cancer therapeutic agent comprising the nucleic acid according to claim 3.

8. An induced pluripotent stem cell (iPS cell) inducer comprising the gene expression vector according to claim 4.

9. A direct reprogramming agent comprising the gene expression vector according to claim 4.

10. A cancer therapeutic agent comprising the gene expression vector according to claim 4.

11. An induced pluripotent stem cell (iPS cell) inducer comprising the mutant KLF protein according to claim 1.

12. The iPS cell inducer according to claim 11, further comprising (i) and/or (ii):
     (i) any of an OCT3/4 protein, a nucleic acid encoding the protein, or a gene expression vector comprising the nucleic acid in an expressible state;
     (ii) any of a SOX1 protein, a SOX2 protein, a SOX3 protein, a SOX15 protein or a SOX17 protein, a nucleic acid encoding any of the proteins, or a gene expression vector comprising the nucleic acid in an expressible state.

13. The iPS cell inducer according to claim 12, further comprising
     (iii) any of a C-MYC protein, a T58A mutant of the C-MYC protein, an N-MYC protein or a L-MYC protein, a nucleic acid encoding any of the proteins, or a gene expression vector comprising the nucleic acid in an expressible state.

14. A direct reprogramming agent comprising a mutant KLF protein according to claim 1.

15. A method for producing an iPS cell, comprising introducing an iPS cell inducer comprising the following (1) to (3), into a somatic cell:

(1) a mutant KLF protein according to claim 1, (2) any of an OCT3/4 protein, a nucleic acid encoding the protein, or a gene expression vector comprising the nucleic acid in an expressible state, and (3) any of a SOX1 protein, a SOX2 protein, a SOX3 protein, a SOX15 protein or a SOX17 protein, a nucleic acid encoding any of the proteins, or a gene expression vector comprising the nucleic acid in an expressible state; and cultivating the somatic cell after the introduction step in the presence of one or more of a basic fibroblast growth factor, a TGF-β1 protein, a BMP protein, a Wnt3 protein, a GSK3β inhibitor, a Wnt inhibitor, retinoic acid, ascorbic acid, and a ROCK inhibitor.

16. The production method according to claim 15, further comprising a selection step of selecting an iPS cell induced in the cultivation step.

17. The production method according to claim 15, wherein the somatic cell is human-derived.

18. A method for producing an iPS cell, comprising introducing an iPS cell inducer comprising the following (1) to (4), into a somatic cell:

(1) a mutant KLF protein according to claim 1, (2) any of an OCT3/4 protein, a nucleic acid encoding the protein, or a gene expression vector comprising the nucleic acid in an expressible state, (3) any of a SOX1 protein, a SOX2 protein, a SOX3 protein, a SOX15 protein or a SOX17 protein, a nucleic acid encoding any of the proteins, or a gene expression vector comprising the nucleic acid in an expressible state, and (4) any of a C-MYC protein, an N-MYC protein, an L-MYC protein, or a T58A mutant protein of the C-MYC protein, a nucleic acid encoding any of the proteins, or a gene expression vector comprising the nucleic acid in an expressible state; and cultivating the somatic cell after the introduction step.

19. A cancer therapeutic agent comprising, the mutant KLF protein according to claim 1.

* * * * *

SEQUENCE LISTING

```
<160> NUMBER OF SEQ ID NOS: 31

<210> SEQ ID NO 1
<211> LENGTH: 362
<212> TYPE: PRT
<213> ORGANISM: Homo sapiens

<400> SEQUENCE: 1

Met Ala Thr Ala Glu Thr Ala Leu Pro Ser Ile Ser Thr Leu Thr Ala
1               5                   10                  15

Leu Gly Pro Phe Pro Asp Thr Gln Asp Asp Phe Leu Lys Trp Trp Arg
                20                  25                  30

Ser Glu Glu Ala Gln Asp Met Gly Pro Gly Pro Pro Asp Pro Thr Glu
            35                  40                  45

Pro Pro Leu His Val Lys Ser Glu Asp Gln Pro Gly Glu Glu Glu Asp
        50                  55                  60

Asp Glu Arg Gly Ala Asp Ala Thr Trp Asp Leu Asp Leu Leu Leu Thr
65                  70                  75                  80

Asn Phe Ser Gly Pro Glu Pro Gly Gly Ala Pro Gln Thr Cys Ala Leu
                85                  90                  95

Ala Pro Ser Glu Ala Ser Gly Ala Gln Tyr Pro Pro Pro Pro Glu Thr
                100                 105                 110

Leu Gly Ala Tyr Ala Gly Gly Pro Gly Leu Val Ala Gly Leu Leu Gly
                115                 120                 125
```

-continued

```
Ser Glu Asp His Ser Gly Trp Val Arg Pro Ala Leu Arg Ala Arg Ala
    130                 135                 140

Pro Asp Ala Phe Val Gly Pro Ala Leu Ala Pro Ala Pro Ala Pro Glu
145                 150                 155                 160

Pro Lys Ala Leu Ala Leu Gln Pro Val Tyr Pro Gly Pro Gly Ala Gly
                165                 170                 175

Ser Ser Gly Gly Tyr Phe Pro Arg Thr Gly Leu Ser Val Pro Ala Ala
                180                 185                 190

Ser Gly Ala Pro Tyr Gly Leu Leu Ser Gly Tyr Pro Ala Met Tyr Pro
            195                 200                 205

Ala Pro Gln Tyr Gln Gly His Phe Gln Leu Phe Arg Gly Leu Gln Gly
    210                 215                 220

Pro Ala Pro Gly Pro Ala Thr Ser Pro Ser Phe Leu Ser Cys Leu Gly
225                 230                 235                 240

Pro Gly Thr Val Gly Thr Gly Leu Gly Gly Thr Ala Glu Asp Pro Gly
                245                 250                 255

Val Ile Ala Glu Thr Ala Pro Ser Lys Arg Gly Arg Arg Ser Trp Ala
            260                 265                 270

Arg Lys Arg Gln Ala Ala His Thr Cys Ala His Pro Gly Cys Gly Lys
        275                 280                 285

Ser Tyr Thr Lys Ser Ser His Leu Lys Ala His Leu Arg Thr His Thr
    290                 295                 300

Gly Glu Lys Pro Tyr Ala Cys Thr Trp Glu Gly Cys Gly Trp Arg Phe
305                 310                 315                 320

Ala Arg Ser Asp Glu Leu Thr Arg His Tyr Arg Lys His Thr Gly Gln
                325                 330                 335

Arg Pro Phe Arg Cys Gln Leu Cys Pro Arg Ala Phe Ser Arg Ser Asp
                340                 345                 350

His Leu Ala Leu His Met Lys Arg His Leu
    355                 360
```

```
<210> SEQ ID NO 2
<211> LENGTH: 1613
<212> TYPE: DNA
<213> ORGANISM: Homo sapiens

<400> SEQUENCE: 2
agagttcacg aggcagccga ggaagaggag gcttgaggcc cagggtgggc accagccagc      60
catggccaca gccgagaccg ccttgccctc catcagcaca ctgaccgccc tgggcccctt     120
cccggacaca caggatgact tcctcaagtg gtggcgctcc gaagaggcgc aggacatggg     180
cccgggtcct cctgacccca cggagccgcc cctccacgtg aagtctgagg accagcccgg     240
ggaggaagag gacgatgaga ggggcgcgga cgccacctgg gacctggatc tcctcctcac     300
caacttctcg ggcccggagc ccggtggcgc gccccagacc tgcgctctgg cgcccagcga     360
ggcctccggg gcgcaatatc cgccgccgcc cgagactctg ggcgcatatg ctggcggccc     420 gggggctggtg gctgggcttt ggggttcgga ggatcactcg ggttgggtgc gccctgccct     480
gcgagcccgg gctcccgacg ccttcgtggg cccagccctg ctccagcccc ggccccga     540 gcccaaggcg ctggcgctgc aaccggtgta cccggggccc ggcgccggct cctcgggtgg     600
ctacttcccg cggaccgggc tttcagtgcc tgcggcgtcg ggcgccccct acgggctact     660
gtccgggtac cccgcgatgt acccggcgcc tcagtaccaa gggcacttcc agctcttccg     720
cgggctccag ggaccgcgc ccggtcccgc cacgtcccc tccttcctga gttgtttggg     780
```

-continued

```
acccgggacg gtgggcactg gactcggggg gactgcagag gatccaggtg tgatagccga    840
gaccgcgcca tccaagcgag gccgacgttc gtgggcgcgc aagaggcagg cagcgcacac    900
gtgcgcgcac ccgggttgcg gcaagagcta caccaagagc tcccacctga aggcgcatct    960
gcgcacgcac acaggggaga agccatacgc ctgcacgtgg gaaggctgcg gctggagatt   1020
cgcgcgctcg gacgagctga cccgccacta ccggaaacac acggggcagc gccccttccg   1080
ctgccagctc tgcccacgtg ctttttcgcg ctctgaccac ctggccttgc acatgaagcg   1140
ccacctttga gccctgccct ggcacttgga ctctcctagt gactggggat gggacaagaa   1200
gcctgtttgg tggtctcttc acacggacgc gcgtgacaca atgctgggtg gttttcccac   1260
gaatggaccc tctcctggac tcgcgttccc aaagatccac ccaaatatca aacacggacc   1320
catagacagc cctgggggag cctcttacgg aaaatccgac aagccttcag ccacagggag   1380
ccacacagag atgtccaaac tgtcgtgcaa acccagtgag acagaccgcc aaataaacgg   1440
actcagtgga cactcagacc agctcccaga tggccctgga cagcaggaga gggtgtggga   1500
tgaggcttcc cagagaccct gggtctagaa agcggctcct gaaggtccct tattgtggct   1560
gatattaact gtcaatggtt atgggtccta taaaaatgcc cctcccagat aaa           1613
```

```
<210> SEQ ID NO 3
<211> LENGTH: 355
<212> TYPE: PRT
<213> ORGANISM: Homo sapiens

<400> SEQUENCE: 3

Met Ala Leu Ser Glu Pro Ile Leu Pro Ser Phe Ser Thr Phe Ala Ser
1               5                   10                  15

Pro Cys Arg Glu Arg Gly Leu Gln Glu Arg Trp Pro Arg Ala Glu Pro
                20                  25                  30

Glu Ser Gly Gly Thr Asp Asp Asp Leu Asn Ser Val Leu Asp Phe Ile
            35                  40                  45

Leu Ser Met Gly Leu Asp Gly Leu Gly Ala Glu Ala Ala Pro Glu Pro
        50                  55                  60

Pro Pro Pro Pro Pro Pro Pro Ala Phe Tyr Tyr Pro Glu Pro Gly Ala
65                  70                  75                  80

Pro Pro Pro Tyr Ser Ala Pro Ala Gly Gly Leu Val Ser Glu Leu Leu
                85                  90                  95

Arg Pro Glu Leu Asp Ala Pro Leu Gly Pro Ala Leu His Gly Arg Phe
                100                 105                 110

Leu Leu Ala Pro Pro Gly Arg Leu Val Lys Ala Glu Pro Pro Glu Ala
            115                 120                 125

Asp Gly Gly Gly Gly Tyr Gly Cys Ala Pro Gly Leu Thr Arg Gly Pro
        130                 135                 140

Arg Gly Leu Lys Arg Glu Gly Ala Pro Gly Pro Ala Ala Ser Cys Met
145                 150                 155                 160

Arg Gly Pro Gly Gly Arg Pro Pro Pro Pro Asp Thr Pro Pro Leu
                165                 170                 175

Ser Pro Asp Gly Pro Ala Arg Leu Pro Ala Pro Gly Pro Arg Ala Ser
            180                 185                 190

Phe Pro Pro Pro Phe Gly Gly Pro Gly Phe Gly Ala Pro Gly Pro Gly
            195                 200                 205

Leu His Tyr Ala Pro Pro Ala Pro Pro Ala Phe Gly Leu Phe Asp Asp
        210                 215                 220

Ala Ala Ala Ala Ala Ala Ala Leu Gly Leu Ala Pro Pro Ala Ala Arg
```

```
225                 230                 235                 240

Gly Leu Leu Thr Pro Pro Ala Ser Pro Leu Glu Leu Leu Glu Ala Lys
                245                 250                 255

Pro Lys Arg Gly Arg Arg Ser Trp Pro Arg Lys Arg Thr Ala Thr His
                260                 265                 270

Thr Cys Ser Tyr Ala Gly Cys Gly Lys Thr Tyr Thr Lys Ser Ser His
                275                 280                 285

Leu Lys Ala His Leu Arg Thr His Thr Gly Glu Lys Pro Tyr His Cys
        290                 295                 300

Asn Trp Asp Gly Cys Gly Trp Lys Phe Ala Arg Ser Asp Glu Leu Thr
305                 310                 315                 320

Arg His Tyr Arg Lys His Thr Gly His Arg Pro Phe Gln Cys His Leu
                325                 330                 335

Cys Asp Arg Ala Phe Ser Arg Ser Asp His Leu Ala Leu His Met Lys
                340                 345                 350

Arg His Met
        355

<210> SEQ ID NO 4
<211> LENGTH: 2819
<212> TYPE: DNA
<213> ORGANISM: Homo sapiens

<400> SEQUENCE: 4
acagagccgt ccccgcccgc ccgcgccccg accagcccgg cctcgggcag ccactcaccg      60
tgtccccgtc cgcgtccttt ctccccgggt cccggccatg gcgctgagtg aacccatcct     120
gccgtccttc tccactttcg ccagcccgtg ccgcgagcgc ggcctgcagg agcgctggcc     180
gcgcgccgaa cccgagtccg gcggcaccga cgacgacctc aacagcgtgc tggacttcat     240
cctgtccatg gggctggatg gcctgggcgc cgaggccgcc ccggagccgc cgccgccgcc     300
cccgccgcct gcgttctatt accccgaacc cggcgcgccc ccgccctaca gcgccccccgc    360 gggtggcctg gtgtctgagc tgctgcgacc cgagctggat gcgccgctgg gcccgcact      420 gcacggccgc tttctgctgg cgccgcccgg ccgcctggtc aaggccgagc ccctgaagc      480 ggacggcggc ggcggctacg gctgcgcccc cgggctgacc cgtggaccgc gcggcctcaa     540
gcgcgagggc gccccgggcc cggcggcttc gtgcatgcga ggtcccgggg ccgcccccc      600 gccgccgccc gacacaccgc cgctcagccc cgacggcccc gcgcgcctgc ccgcgcccgg     660
tccgcgcgcc tccttcccgc cgcctttcgg tggccctggt ttcggcgcgc ccgggcccgg     720
cctgcattac gcgccgcctg cgcccccagc cttcggtctc ttcgacgacg cggccgccgc     780
cgcggcagcc ctgggcctgg cgcccccccgc cgcccgcggt ctcctcacgc cgcctgcgtc    840
cccgctggag ctgctggagg ccaagccaaa gcgcggccgc cgctcttggc cccgcaaacg     900
caccgccact cacacctgca gctacgcggg ctgcggcaag acctacacca gagttcgca     960 tctgaaggcg catctgcgca cgcacacagg tgagaagccc taccactgca actgggacgg    1020
ctgcggctgg aagtttgcgc gctcagacga gctcacgcgc cactaccgaa agcacacggg    1080
ccaccggcca ttccagtgcc atctgtgcga tcgtgccttc tcgcgctccg atcacctggc    1140
gctgcacatg aaacggcaca tgtagccggg acgcccccgc ccacctgcgc gcggccgtgg    1200
cgggtcccac gcgccgggcg cggccccctc ccaaactgtg actggtattt attggaccca    1260
gagaaccggg ccgggcacag cgtggctaca gagggtctcc ctcgatgacg acgacgacga    1320
cgccaccacc ccagcccccg tctgtgactg aaggcccggt gggaaaagac cacgatcctc    1380
```

```
cttgacgagt tttgtttttc aaaatggtgc aataatttaa gtggcatctt ctctcccacc      1440
gggtctacac tagaggatcg aggcttgtga tgccttgtga gaaataaggg ccttaatttg      1500
tactgtctgc ggcatttttt ataatattgt atatagtgac tgacaaatat tgtattactg      1560
tacatagaga gacaggtggg catttttggg ctacctggtt cgttttata agattttgct       1620 gggttggttt ttttttttaat taaaaagttt tgcatctttt aaaaaaaatc acagcactgg     1680
tctggttgct tggaactggg gccttggggc acttgggagg aggggggagc ggagagtttg     1740
atggagggca gccccactaa agcatcgtgt gcagtgggtc ctgcgtctgc cagcaccggg      1800
actgccagct gctgtgcctg cctgccagga acctgtgggt ttttctgtaa atttagacac      1860
tgcattttag gactgaggga gggttatttt aaggttgttc tttgagccat aaattgcctc      1920
tttgccccac agctggggaa agtgctggtc ccactgacgt ggcctcctct acgttgaaaa      1980
aaataaaact acttacctct tcctggaagc ctctgaggtt ttagccaaat ttctggagtg     2040
ccagctctat attttattt ttatttttaa aggggggttaa cctgctgagt ttctggcatg      2100
ttctgccctt tactcgtctc gacatttagc aagtctttc ttaaggggtg agttccccat       2160
tctgctagcg gaaaacagtg aaacctgcat tcgagggcca tgcatgaagc tcttttccag     2220
atgaggaaac ggaggcccgg agaggtagcg gcagggtggt ggagttgggt tgttagcctg     2280
ctctgtctgc ctccaagggg ccctgaaccc cactggaagg gagtggtagc tttctacaat      2340
gacccacctg ttgtgtgcat tggaaggcta ggagagcctc ctccctgta ggtctcctgg       2400 tgcaaaaaat tcactgcctc aatggtagga ggtgaccagt ctggaaaccc acctggagag      2460
cagaggagac ccctaaatcc caccacccca agtgtctcag gcaaggaggt atctctcccc      2520
ccagatttca cctgccaccc ctcaccttcc ccattctcag gggccccggg taaccatgac      2580
caccaaccat tgcacaagtt tccagaaagt gaaaatagct cgtaagcagc gcctgcttta      2640
aaacactctc accccgttgc gacagaggct gggatttcct ccctccctgc atccttcctc      2700
ctccccaact acggcagccc tggaaacagc tgagaggtgt ttggtaatcc acgaaaagca      2760
gaaatacgat ttgacaatct gattcatttt ccgagagtaa atagcctggc ctcacttcc       2819
```

<210> SEQ ID NO 5
<211> LENGTH: 513
<212> TYPE: PRT
<213> ORGANISM: Homo sapiens

<400> SEQUENCE: 5

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
```

-continued

```
             115                 120                 125

Ser Ala Ser Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
                180                 185                 190

Val Ser Pro Ser Gly Gly Phe Val Ala Glu Leu Leu Arg Pro Glu Leu
                195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
                260                 265                 270

Thr Cys Pro Lys Ile Lys Gln Glu Ala Val Ser Ser Cys Thr His Leu
                275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
                340                 345                 350

Pro Asp Gln Met Gln Pro Gln Val Pro Pro Leu His Tyr Gln Gly Gln
                355                 360                 365

Ser Arg Gly Phe Val Ala Arg Ala Gly Glu Pro Cys Val Cys Trp Pro
    370                 375                 380

His Phe Gly Thr His Gly Met Met Leu Thr Pro Pro Ser Ser Pro Leu
385                 390                 395                 400

Glu Leu Met Pro Pro Gly Ser Cys Met Pro Glu Glu Pro Lys Pro Lys
                405                 410                 415

Arg Gly Arg Arg Ser Trp Pro Arg Lys Arg Thr Ala Thr His Thr Cys
                420                 425                 430

Asp Tyr Ala Gly Cys Gly Lys Thr Tyr Thr Lys Ser Ser His Leu Lys
                435                 440                 445

Ala His Leu Arg Thr His Thr Gly Glu Lys Pro Tyr His Cys Asp Trp
    450                 455                 460

Asp Gly Cys Gly Trp Lys Phe Ala Arg Ser Asp Glu Leu Thr Arg His
465                 470                 475                 480

Tyr Arg Lys His Thr Gly His Arg Pro Phe Gln Cys Gln Lys Cys Asp
                485                 490                 495

Arg Ala Phe Ser Arg Ser Asp His Leu Ala Leu His Met Lys Arg His
                500                 505                 510

Phe
```

<210> SEQ ID NO 6
<211> LENGTH: 3038

```
<212> TYPE: DNA
<213> ORGANISM: Homo sapiens

<400> SEQUENCE: 6
ggcagtttcc cgaccagaga gaacgaacgt gtctgcgggc gcgcggggag cagaggcggt        60
ggcgggcggc ggcggcaccg ggagccgccg agtgaccctc ccccgcccct ctggcccccc       120
accctcccac ccgcccgtgg cccgcgccca tggccgcgcg cgctccacac aactcaccgg       180
agtccgcgcc ttgcgccgcc gaccagttcg cagctccgcg ccacggcagc cagtctcacc       240
tggcggcacc gcccgcccac cgccccggcc acagcccctg cgcccacggc agcactcgag       300
gcgaccgcga cagtggtggg ggacgctgct gagtggaaga gagcgcagcc cggccaccgg       360
acctacttac tcgccttgct gattgtctat ttttgcgttt acaacttttc taagaacttt       420
tgtatacaaa ggaacttttt aaaaaagacg cttccaagtt atatttaatc caaagaagaa       480
ggatctcggc caatttgggg ttttgggttt tggcttcgtt tcttctcttc gttgactttg       540
gggttcaggt gccccagctg cttcgggctg ccgaggacct tctgggcccc cacattaatg       600
aggcagccac ctggcgagtc tgacatggct gtcagcgacg cgctgctccc atctttctcc       660
acgttcgcgt ctggcccggc gggaagggag aagacactgc gtcaagcagg tgccccgaat       720
aaccgctggc gggaggagct ctcccacatg aagcgacttc ccccagtgct tcccggccgc       780
ccctatgacc tggcggcggc gaccgtggcc acagacctgg agagcggcgg agccggtgcg       840
gcttgcggcg gtagcaacct ggcgccccta cctcggagag agaccgagga gttcaacgat       900
ctcctggacc tggactttat tctctccaat tcgctgaccc atcctccgga gtcagtggcc       960
gccaccgtgt cctcgtcagc gtcagcctcc tcttcgtcgt cgccgtcgag cagcggccct      1020
gccagcgcgc cctccacctg cagcttcacc tatccgatcc gggccgggaa cgacccgggc      1080
gtggcgccgg gcggcacggg cggaggcctc ctctatggca gggagtccgc tccccctccg      1140
acggctccct tcaacctggc ggacatcaac gacgtgagcc cctcgggcgg cttcgtggcc      1200
gagctcctgc ggccagaatt ggacccggtg tacattccgc cgcagcagcc gcagccgcca      1260
ggtggcgggc tgatgggcaa gttcgtgctg aaggcgtcgc tgagcgcccc tggcagcgag      1320 tacgcagcc cgtcggtcat cagcgtcagc aaaggcagcc ctgacggcag ccacccggtg      1380
gtggtggcgc cctacaacgg cgggccgccg cgcacgtgcc ccaagatcaa gcaggaggcg      1440
gtctcttcgt gcacccactt gggcgctgga ccccctctca gcaatggcca ccggccggct      1500
gcacacgact ccccctgggg gcggcagctc cccagcagga ctaccccgac cctgggtctt      1560
gaggaagtgc tgagcagcag ggactgtcac cctgccctgc cgcttcctcc cggcttccat      1620
ccccacccgg ggcccaatta cccatccttc ctgcccgatc agatgcagcc gcaagtcccg      1680
ccgctccatt accaaggtca gtcccgggga tttgtagctc gggctgggga ccctgtgtg      1740 tgctggcccc acttcgggac acacgggatg atgctcaccc caccttcttc acccctagag      1800
ctcatgccac ccggttcctg catgccagag gagcccaagc aaagagggg aagacgatcg      1860 tggcccagga aaaggaccgc acccacact tgtgattacg cgggctgcgg caaaacctac       1920
acaaagagtt cccatctcaa ggcacacctg cgaacccaca caggtgagaa accttaccac      1980
tgtgactggg acggctgtgg atggaaattc gcccgctcag atgaactgac caggcactac      2040
cgtaaacaca cggggcaccg cccgttccag tgccaaaaat gcgaccgagc attttccagg      2100
tcggaccacc tcgccttaca catgaagagg cattttaaa tcccagacag tggatatgac      2160
ccacactgcc agaagagaat tcagtatttt ttactttca cactgtcttc ccgatgaggg      2220
```

-continued

```
aaggagccca gccagaaagc actacaatca tggtcaagtt cccaactgag tcatcttgtg      2280
agtggataat caggaaaaat gaggaatcca aaagacaaaa atcaaagaac agatggggtc      2340
tgtgactgga tcttctatca ttccaattct aaatccgact tgaatattcc tggacttaca      2400
aaatgccaag ggggtgactg gaagttgtgg atatcagggt ataaattata tccgtgagtt      2460
gggggaggga agaccagaat tcccttgaat tgtgtattga tgcaatataa gcataaaaga      2520
tcaccttgta ttctctttac cttctaaaag ccattattat gatgttagaa gaagaggaag      2580
aaattcaggt acagaaaaca tgtttaaata gcctaaatga tggtgcttgg tgagtcttgg      2640
ttctaaaggt accaaacaag gaagccaaag ttttcaaact gctgcatact ttgacaagga      2700
aaatctatat ttgtcttccg atcaacattt atgacctaag tcaggtaata tacctggttt      2760
acttctttag catttttatg cagacagtct gttatgcact gtggtttcag atgtgcaata      2820
atttgtacaa tggtttattc ccaagtatgc cttaagcaga acaaatgtgt ttttctatat      2880
agttccttgc cttaataaat atgtaatata aatttaagca aacgtctatt ttgtatattt      2940
gtaaactaca aagtaaaatg aacattttgt ggagtttgta ttttgcatac tcaaggtgag      3000
aattaagttt taaataaacc tataatattt tatctgaa                              3038
```

<210> SEQ ID NO 7
<211> LENGTH: 457
<212> TYPE: PRT
<213> ORGANISM: Homo sapiens

<400> SEQUENCE: 7

```
Met Ala Thr Arg Val Leu Ser Met Ser Ala Arg Leu Gly Pro Val Pro
1               5                   10                  15

Gln Pro Pro Ala Pro Gln Asp Glu Pro Val Phe Ala Gln Leu Lys Pro
                20                  25                  30

Val Leu Gly Ala Ala Asn Pro Ala Arg Asp Ala Ala Leu Phe Pro Gly
            35                  40                  45

Glu Glu Leu Lys His Ala His His Arg Pro Gln Ala Gln Pro Ala Pro
        50                  55                  60

Ala Gln Ala Pro Gln Pro Ala Gln Pro Pro Ala Thr Gly Pro Arg Leu
65                  70                  75                  80

Pro Pro Glu Asp Leu Val Gln Thr Arg Cys Glu Met Glu Lys Tyr Leu
                85                  90                  95

Thr Pro Gln Leu Pro Pro Val Pro Ile Ile Pro Glu His Lys Lys Tyr
                100                 105                 110

Arg Arg Asp Ser Ala Ser Val Val Asp Gln Phe Phe Thr Asp Thr Glu
            115                 120                 125

Gly Leu Pro Tyr Ser Ile Asn Met Asn Val Phe Leu Pro Asp Ile Thr
        130                 135                 140

His Leu Arg Thr Gly Leu Tyr Lys Ser Gln Arg Pro Cys Val Thr His
145                 150                 155                 160

Ile Lys Thr Glu Pro Val Ala Ile Phe Ser His Gln Ser Glu Thr Thr
                165                 170                 175

Ala Pro Pro Pro Ala Pro Thr Gln Ala Leu Pro Glu Phe Thr Ser Ile
            180                 185                 190

Phe Ser Ser His Gln Thr Ala Ala Pro Glu Val Asn Asn Ile Phe Ile
            195                 200                 205

Lys Gln Glu Leu Pro Thr Pro Asp Leu His Leu Ser Val Pro Thr Gln
        210                 215                 220

Gln Gly His Leu Tyr Gln Leu Leu Asn Thr Pro Asp Leu Asp Met Pro
```

-continued

```
    225                 230                 235                 240

Ser Ser Thr Asn Gln Thr Ala Ala Met Asp Thr Leu Asn Val Ser Met
                245                 250                 255

Ser Ala Ala Met Ala Gly Leu Asn Thr His Thr Ser Ala Val Pro Gln
                260                 265                 270

Thr Ala Val Lys Gln Phe Gln Gly Met Pro Pro Cys Thr Tyr Thr Met
                275                 280                 285

Pro Ser Gln Phe Leu Pro Gln Gln Ala Thr Tyr Phe Pro Pro Ser Pro
                290                 295                 300

Pro Ser Ser Glu Pro Gly Ser Pro Asp Arg Gln Ala Glu Met Leu Gln
305                 310                 315                 320

Asn Leu Thr Pro Pro Pro Ser Tyr Ala Ala Thr Ile Ala Ser Lys Leu
                325                 330                 335

Ala Ile His Asn Pro Asn Leu Pro Thr Thr Leu Pro Val Asn Ser Gln
                340                 345                 350

Asn Ile Gln Pro Val Arg Tyr Asn Arg Arg Ser Asn Pro Asp Leu Glu
                355                 360                 365

Lys Arg Arg Ile His Tyr Cys Asp Tyr Pro Gly Cys Thr Lys Val Tyr
        370                 375                 380

Thr Lys Ser Ser His Leu Lys Ala His Leu Arg Thr His Thr Gly Glu
385                 390                 395                 400

Lys Pro Tyr Lys Cys Thr Trp Glu Gly Cys Asp Trp Arg Phe Ala Arg
                405                 410                 415

Ser Asp Glu Leu Thr Arg His Tyr Arg Lys His Thr Gly Ala Lys Pro
                420                 425                 430

Phe Gln Cys Gly Val Cys Asn Arg Ser Phe Ser Arg Ser Asp His Leu
                435                 440                 445

Ala Leu His Met Lys Arg His Gln Asn
        450                 455

<210> SEQ ID NO 8
<211> LENGTH: 3349
<212> TYPE: DNA
<213> ORGANISM: Homo sapiens

<400> SEQUENCE: 8
agtcgcgggg caggtacgtg cgctcgcggt tctctcgcgg aggtcggcgg tggcgggagc      60
gggctccgga gagcctgaga gcacggtggg gcggggcggg agaaagtggc cgcccggagg     120
acgttggcgt ttacgtgtgg aagagcggaa gagtttttgct tttcgtgcgc gccttcgaaa    180
actgcctgcc gctgtctgag gagtccaccc gaaacctccc ctcctccgcc ggcagccccg     240
cgctgagctc gccgacccaa gccagcgtgg gcgaggtggg aagtgcgccc gacccgcgcc     300
tggagctgcg cccccgagtg cccatggcta caagggtgct gagcatgagc gcccgcctgg     360
gacccgtgcc ccagccgccg gcgccgcagg acgagccggt gttcgcgcag ctcaagccgg     420
tgctgggcgc cgcgaatccg gcccgcgacg cggcgctctt ccccggcgag gagctgaagc     480
acgcgcacca ccgcccgcag gcgcagcccg cgcccgcgca ggccccgcag ccggcccagc     540 cgccgccac cggcccgcgg ctgcctccag aggacctggt ccagacaaga tgtgaaatgg      600
agaagtatct gacacctcag cttcctccag ttcctataat tccagagcat aaaaagtata     660
gacgagacag tgcctcagtc gtagaccagt tcttcactga cactgaaggg ttaccttaca     720
gtatcaacat gaacgtcttc ctccctgaca tcactcacct gagaactggc ctctacaaat     780
cccagagacc gtgcgtaaca cacatcaaga cagaacctgt tgccatttttc agccaccaga     840
```

```
gtgaaacgac tgcccctcct ccggccccga cccaggccct ccctgagttc accagtatat     900
tcagctcaca ccagaccgca gctccagagg tgaacaatat tttcatcaaa caagaacttc     960
ctacaccaga tcttcatctt tctgtcccta cccagcaggg ccacctgtac cagctactga    1020
atacaccgga tctagatatg cccagttcta caaatcagac agcagcaatg gacactctta    1080
atgtttctat gtcagctgcc atggcaggcc ttaacacaca cacctctgct gttccgcaga    1140
ctgcagtgaa acaattccag ggcatgcccc cttgcacata cacaatgcca agtcagtttc    1200
ttccacaaca ggccacttac tttcccccgt caccaccaag ctcagagcct ggaagtccag    1260
atagacaagc agagatgctc cagaatttaa ccccacctcc atcctatgct gctacaattg    1320
cttctaaact ggcaattcac aatccaaatt tacccaccac cctgccagtt aactcacaaa    1380
acatccaacc tgtcagatac aatagaagga gtaaccccga tttggagaaa cgacgcatcc    1440
actactgcga ttaccctggt tgcacaaaag tttataccaa gtcttctcat ttaaaagctc    1500
acctgaggac tcacactggt gaaaagccat acaagtgtac ctgggaaggc tgcgactgga    1560
ggttcgcgcg atcggatgag ctgacccgcc actaccggaa gcacacaggc gccaagccct    1620
tccagtgcgg ggtgtgcaac cgcagcttct cgcgctctga ccacctggcc ctgcatatga    1680
agaggcacca gaactgagca ctgcccgtgt gacccgttcc aggtcccctg ggctccctca    1740
aatgacagac ctaactattc ctgtgtaaaa acaacaaaaa caaacaaaag caagaaaacc    1800
acaactaaaa ctggaaatgt atattttgta tatttgagaa aacagggaat acattgtatt    1860
aataccaaag tgtttggtca tttttaagaat ctggaatgct tgctgtaatg tatatggctt    1920
tactcaagca gatctcatct catgacaggc agccacgtct caacatgggt aaggggtggg    1980
ggtggagggg agtgtgtgca gcgtttttac ctaggcacca tcatttaatg tgacagtgtt    2040
cagtaaacaa atcagttggc aggcaccaga agaagaatgg attgtatgtc aagattttac    2100
ttggcattga gtagtttttt tcaatagtag gtaattcctt agagatacag tatacctggc    2160
aattcacaaa tagccattga acaaatgtgt gggtttttaa aaattatata catatatgag    2220
ttgcctatat ttgctattca aaattttgta aatatgcaaa tcagctttat aggtttatta    2280
caagtttttt aggattcttt tggggaagag tcataattct tttgaaaata accatgaata    2340
cacttacagt taggatttgt ggtaaggtac ctctcaacat taccaaaatc atttctttag    2400
agggaaggaa taatcattca aatgaacttt aaaaaagcaa atttcatgca ctgattaaaa    2460
taggattatt ttaaatacaa aaggcatttt atatgaatta taaactgaag agcttaaaga    2520
tagttacaaa atacaaaagt tcaacctctt acaataagct aaacgcaatg tcatttttaa    2580
aaagaaggac ttagggtgtc gttttcacat atgacaatgt tgcatttatg atgcagtttc    2640
aagtaccaaa acgttgaatt gatgatgcag ttttcatata tcgagatgtt cgctcgtgca    2700
gtactgttgg ttaaatgaca atttatgtgg attttgcatg taatacacag tgagacacag    2760
taattttatc taaattacag tgcagtttag ttaatctatt aatactgact cagtgtctgc    2820
ctttaaatat aaatgatatg ttgaaaactt aaggaagcaa atgctacata tatgcaatat    2880
aaaatagtaa tgtgatgctg atgctgttaa ccaaagggca gaataaataa gcaaaatgcc    2940
aaaaggggtc ttaattgaaa tgaaaattta attttgtttt taaaatattg tttatcttta    3000
tttattttgt ggtaatatag taagtttttt tagaagacaa ttttcataac ttgataaatt    3060
atagttttgt ttgttagaaa agttgctctt aaaagatgta aatagatgac aaacgatgta    3120
aataattttg taagaggctt caaaatgttt atacgtggaa acacacctac atgaaaagca    3180
```

-continued

```
gaaatcggtt gctgttttgc ttcttttccc ctcttatttt tgtattgtgg tcatttccta   3240
tgcaaataat ggagcaaaca gctgtatagt tgtagaattt tttgagagaa tgagatgttt   3300
atatattaac gacaattttt tttttggaaa ataaaaagtg cctaaaaga              3349
```

<210> SEQ ID NO 9
<211> LENGTH: 59
<212> TYPE: PRT
<213> ORGANISM: Homo sapiens

<400> SEQUENCE: 9

```
Thr Gly Glu Lys Pro Tyr Ala Cys Thr Trp Glu Gly Cys Gly Trp Arg
1               5                   10                  15

Phe Ala Arg Ser Asp Glu Leu Thr Arg His Tyr Arg Lys His Thr Gly
            20                  25                  30

Gln Arg Pro Phe Arg Cys Gln Leu Cys Pro Arg Ala Phe Ser Arg Ser
        35                  40                  45

Asp His Leu Ala Leu His Met Lys Arg His Leu
    50                  55
```

<210> SEQ ID NO 10
<211> LENGTH: 59
<212> TYPE: PRT
<213> ORGANISM: Homo sapiens

<400> SEQUENCE: 10

```
Thr Gly Glu Lys Pro Tyr His Cys Asn Trp Asp Gly Cys Gly Trp Lys
1               5                   10                  15

Phe Ala Arg Ser Asp Glu Leu Thr Arg His Tyr Arg Lys His Thr Gly
            20                  25                  30

His Arg Pro Phe Gln Cys His Leu Cys Asp Arg Ala Phe Ser Arg Ser
        35                  40                  45

Asp His Leu Ala Leu His Met Lys Arg His Met
    50                  55
```

<210> SEQ ID NO 11
<211> LENGTH: 59
<212> TYPE: PRT
<213> ORGANISM: Homo sapiens

<400> SEQUENCE: 11

```
Thr Gly Glu Lys Pro Tyr His Cys Asp Trp Asp Gly Cys Gly Trp Lys
1               5                   10                  15

Phe Ala Arg Ser Asp Glu Leu Thr Arg His Tyr Arg Lys His Thr Gly
            20                  25                  30

His Arg Pro Phe Gln Cys Gln Lys Cys Asp Arg Ala Phe Ser Arg Ser
        35                  40                  45

Asp His Leu Ala Leu His Met Lys Arg His Phe
    50                  55
```

<210> SEQ ID NO 12
<211> LENGTH: 60
<212> TYPE: PRT
<213> ORGANISM: Homo sapiens

<400> SEQUENCE: 12

```
Thr Gly Glu Lys Pro Tyr Lys Cys Thr Trp Glu Gly Cys Asp Trp Arg
1               5                   10                  15

Phe Ala Arg Ser Asp Glu Leu Thr Arg His Tyr Arg Lys His Thr Gly
            20                  25                  30
```

-continued

```
Ala Lys Pro Phe Gln Cys Gly Val Cys Asn Arg Ser Phe Ser Arg Ser
        35                  40                  45

Asp His Leu Ala Leu His Met Lys Arg His Gln Asn
    50                  55                  60

<210> SEQ ID NO 13
<211> LENGTH: 360
<212> TYPE: PRT
<213> ORGANISM: Homo sapiens

<400> SEQUENCE: 13

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
                20                  25                  30

Arg Thr Trp Leu Ser Phe Gln Gly Pro Pro Gly Gly Pro Gly Ile Gly
        35                  40                  45

Pro Gly Val Gly Pro Gly Ser Glu Val Trp Gly Ile Pro Pro Cys Pro
    50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
                100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
                180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
                260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
```

-continued

```
                340                    345                    350

Leu Gly Ser Pro Met His Ser Asn
        355                    360

<210> SEQ ID NO 14
<211> LENGTH: 391
<212> TYPE: PRT
<213> ORGANISM: Homo sapiens

<400> SEQUENCE: 14

Met Tyr Ser Met Met Met Glu Thr Asp Leu His Ser Pro Gly Gly Ala
1               5                   10                  15

Gln Ala Pro Thr Asn Leu Ser Gly Pro Ala Gly Ala Gly Gly Gly Gly
            20                  25                  30

Gly Gly Gly Gly Gly Gly Gly Gly Gly Gly Gly Ala Lys Ala Asn Gln
        35                  40                  45

Asp Arg Val Lys Arg Pro Met Asn Ala Phe Met Val Trp Ser Arg Gly
    50                  55                  60

Gln Arg Arg Lys Met Ala Gln Glu Asn Pro Lys Met His Asn Ser Glu
65                  70                  75                  80

Ile Ser Lys Arg Leu Gly Ala Glu Trp Lys Val Met Ser Glu Ala Glu
                85                  90                  95

Lys Arg Pro Phe Ile Asp Glu Ala Lys Arg Leu Arg Ala Leu His Met
            100                 105                 110

Lys Glu His Pro Asp Tyr Lys Tyr Arg Pro Arg Arg Lys Thr Lys Thr
        115                 120                 125

Leu Leu Lys Lys Asp Lys Tyr Ser Leu Ala Gly Gly Leu Leu Ala Ala
    130                 135                 140

Gly Ala Gly Gly Gly Gly Ala Ala Val Ala Met Gly Val Gly Val Gly
145                 150                 155                 160

Val Gly Ala Ala Ala Val Gly Gln Arg Leu Glu Ser Pro Gly Gly Ala
                165                 170                 175

Ala Gly Gly Gly Tyr Ala His Val Asn Gly Trp Ala Asn Gly Ala Tyr
            180                 185                 190

Pro Gly Ser Val Ala Ala Ala Ala Ala Ala Ala Met Met Gln Glu
        195                 200                 205

Ala Gln Leu Ala Tyr Gly Gln His Pro Gly Ala Gly Gly Ala His Pro
    210                 215                 220

His Ala His Pro Ala His Pro His Pro His His Pro His Ala His Pro
225                 230                 235                 240

His Asn Pro Gln Pro Met His Arg Tyr Asp Met Gly Ala Leu Gln Tyr
                245                 250                 255

Ser Pro Ile Ser Asn Ser Gln Gly Tyr Met Ser Ala Ser Pro Ser Gly
            260                 265                 270

Tyr Gly Gly Leu Pro Tyr Gly Ala Ala Ala Ala Ala Ala Ala Ala
        275                 280                 285

Gly Gly Ala His Gln Asn Ser Ala Val Ala Ala Ala Ala Ala Ala Ala
    290                 295                 300

Ala Ala Ser Ser Gly Ala Leu Gly Ala Leu Gly Ser Leu Val Lys Ser
305                 310                 315                 320

Glu Pro Ser Gly Ser Pro Ala Pro Ala His Ser Arg Ala Pro Cys
                325                 330                 335

Pro Gly Asp Leu Arg Glu Met Ile Ser Met Tyr Leu Pro Ala Gly Glu
            340                 345                 350
```

-continued

```
Gly Gly Asp Pro Ala Ala Ala Ala Ala Ala Ala Gln Ser Arg Leu
        355             360             365

His Ser Leu Pro Gln His Tyr Gln Gly Ala Gly Ala Gly Val Asn Gly
    370             375             380

Thr Val Pro Leu Thr His Ile
385             390

<210> SEQ ID NO 15
<211> LENGTH: 317
<212> TYPE: PRT
<213> ORGANISM: Homo sapiens

<400> SEQUENCE: 15

Met Tyr Asn Met Met Glu Thr Glu Leu Lys Pro Pro Gly Pro Gln Gln
1               5               10              15

Thr Ser Gly Gly Gly Gly Gly Asn Ser Thr Ala Ala Ala Ala Gly Gly
            20              25              30

Asn Gln Lys Asn Ser Pro Asp Arg Val Lys Arg Pro Met Asn Ala Phe
        35              40              45

Met Val Trp Ser Arg Gly Gln Arg Arg Lys Met Ala Gln Glu Asn Pro
    50              55              60

Lys Met His Asn Ser Glu Ile Ser Lys Arg Leu Gly Ala Glu Trp Lys
65              70              75              80

Leu Leu Ser Glu Thr Glu Lys Arg Pro Phe Ile Asp Glu Ala Lys Arg
                85              90              95

Leu Arg Ala Leu His Met Lys Glu His Pro Asp Tyr Lys Tyr Arg Pro
            100             105             110

Arg Arg Lys Thr Lys Thr Leu Met Lys Lys Asp Lys Tyr Thr Leu Pro
        115             120             125

Gly Gly Leu Leu Ala Pro Gly Gly Asn Ser Met Ala Ser Gly Val Gly
    130             135             140

Val Gly Ala Gly Leu Gly Ala Gly Val Asn Gln Arg Met Asp Ser Tyr
145             150             155             160

Ala His Met Asn Gly Trp Ser Asn Gly Ser Tyr Ser Met Met Gln Asp
                165             170             175

Gln Leu Gly Tyr Pro Gln His Pro Gly Leu Asn Ala His Gly Ala Ala
            180             185             190

Gln Met Gln Pro Met His Arg Tyr Asp Val Ser Ala Leu Gln Tyr Asn
        195             200             205

Ser Met Thr Ser Ser Gln Thr Tyr Met Asn Gly Ser Pro Thr Tyr Ser
    210             215             220

Met Ser Tyr Ser Gln Gln Gly Thr Pro Gly Met Ala Leu Gly Ser Met
225             230             235             240

Gly Ser Val Val Lys Ser Glu Ala Ser Ser Ser Pro Pro Val Val Thr
                245             250             255

Ser Ser Ser His Ser Arg Ala Pro Cys Gln Ala Gly Asp Leu Arg Asp
            260             265             270

Met Ile Ser Met Tyr Leu Pro Gly Ala Glu Val Pro Glu Pro Ala Ala
        275             280             285

Pro Ser Arg Leu His Met Ser Gln His Tyr Gln Ser Gly Pro Val Pro
    290             295             300

Gly Thr Ala Ile Asn Gly Thr Leu Pro Leu Ser His Met
305             310             315

<210> SEQ ID NO 16
```

```
<211> LENGTH: 446
<212> TYPE: PRT
<213> ORGANISM: Homo sapiens

<400> SEQUENCE: 16

Met Arg Pro Val Arg Glu Asn Ser Ser Gly Ala Arg Ser Pro Arg Val
1               5                   10                  15

Pro Ala Asp Leu Ala Arg Ser Ile Leu Ile Ser Leu Pro Phe Pro Pro
                20                  25                  30

Asp Ser Leu Ala His Arg Pro Pro Ser Ser Ala Pro Thr Glu Ser Gln
            35                  40                  45

Gly Leu Phe Thr Val Ala Ala Pro Ala Pro Gly Ala Pro Ser Pro Pro
        50                  55                  60

Ala Thr Leu Ala His Leu Leu Pro Ala Pro Ala Met Tyr Ser Leu Leu
65                  70                  75                  80

Glu Thr Glu Leu Lys Asn Pro Val Gly Thr Pro Thr Gln Ala Ala Gly
                85                  90                  95

Thr Gly Gly Pro Ala Ala Pro Gly Gly Ala Gly Lys Ser Ser Ala Asn
            100                 105                 110

Ala Ala Gly Gly Ala Asn Ser Gly Gly Gly Ser Ser Gly Gly Ala Ser
        115                 120                 125

Gly Gly Gly Gly Gly Thr Asp Gln Asp Arg Val Lys Arg Pro Met Asn
        130                 135                 140

Ala Phe Met Val Trp Ser Arg Gly Gln Arg Arg Lys Met Ala Leu Glu
145                 150                 155                 160

Asn Pro Lys Met His Asn Ser Glu Ile Ser Lys Arg Leu Gly Ala Asp
                165                 170                 175

Trp Lys Leu Leu Thr Asp Ala Glu Lys Arg Pro Phe Ile Asp Glu Ala
                180                 185                 190

Lys Arg Leu Arg Ala Val His Met Lys Glu Tyr Pro Asp Tyr Lys Tyr
            195                 200                 205

Arg Pro Arg Arg Lys Thr Lys Thr Leu Leu Lys Lys Asp Lys Tyr Ser
        210                 215                 220

Leu Pro Ser Gly Leu Leu Pro Pro Gly Ala Ala Ala Ala Ala Ala Ala
225                 230                 235                 240

Ala Ala Ala Ala Ala Ala Ala Ala Ser Ser Pro Val Gly Val Gly Gln
            245                 250                 255

Arg Leu Asp Thr Tyr Thr His Val Asn Gly Trp Ala Asn Gly Ala Tyr
            260                 265                 270

Ser Leu Val Gln Glu Gln Leu Gly Tyr Ala Gln Pro Pro Ser Met Ser
        275                 280                 285

Ser Pro Pro Pro Pro Ala Leu Pro Pro Met His Arg Tyr Asp Met
        290                 295                 300

Ala Gly Leu Gln Tyr Ser Pro Met Met Pro Pro Gly Ala Gln Ser Tyr
305                 310                 315                 320

Met Asn Val Ala Ala Ala Ala Ala Ala Ser Gly Tyr Gly Gly Met
            325                 330                 335

Ala Pro Ser Ala Thr Ala Ala Ala Ala Ala Tyr Gly Gln Gln Pro
            340                 345                 350

Ala Thr Ala Ala Ala Ala Ala Ala Ala Ala Met Ser Leu Gly
        355                 360                 365

Pro Met Gly Ser Val Val Lys Ser Glu Pro Ser Ser Pro Pro Pro Ala
        370                 375                 380

Ile Ala Ser His Ser Gln Arg Ala Cys Leu Gly Asp Leu Arg Asp Met
```

-continued

```
385                 390                 395                 400

Ile Ser Met Tyr Leu Pro Pro Gly Gly Asp Ala Ala Asp Ala Ala Ser
            405                 410                 415

Pro Leu Pro Gly Gly Arg Leu His Gly Val His Gln His Tyr Gln Gly
            420                 425                 430

Ala Gly Thr Ala Val Asn Gly Thr Val Pro Leu Thr His Ile
        435                 440                 445

<210> SEQ ID NO 17
<211> LENGTH: 233
<212> TYPE: PRT
<213> ORGANISM: Homo sapiens

<400> SEQUENCE: 17

Met Ala Leu Pro Gly Ser Ser Gln Asp Gln Ala Trp Ser Leu Glu Pro
1               5                   10                  15

Pro Ala Ala Thr Ala Ala Ala Ser Ser Ser Ser Gly Pro Gln Glu Arg
            20                  25                  30

Glu Gly Ala Gly Ser Pro Ala Ala Pro Gly Thr Leu Pro Leu Glu Lys
        35                  40                  45

Val Lys Arg Pro Met Asn Ala Phe Met Val Trp Ser Ser Ala Gln Arg
    50                  55                  60

Arg Gln Met Ala Gln Gln Asn Pro Lys Met His Asn Ser Glu Ile Ser
65                  70                  75                  80

Lys Arg Leu Gly Ala Gln Trp Lys Leu Leu Asp Glu Asp Glu Lys Arg
                85                  90                  95

Pro Phe Val Glu Glu Ala Lys Arg Leu Arg Ala Arg His Leu Arg Asp
            100                 105                 110

Tyr Pro Asp Tyr Lys Tyr Arg Pro Arg Arg Lys Ala Lys Ser Ser Gly
        115                 120                 125

Ala Gly Pro Ser Arg Cys Gly Gln Gly Arg Gly Asn Leu Ala Ser Gly
        130                 135                 140

Gly Pro Leu Trp Gly Pro Gly Tyr Ala Thr Thr Gln Pro Ser Arg Gly
145                 150                 155                 160

Phe Gly Tyr Arg Pro Pro Ser Tyr Ser Thr Ala Tyr Leu Pro Gly Ser
                165                 170                 175

Tyr Gly Ser Ser His Cys Lys Leu Glu Ala Pro Ser Pro Cys Ser Leu
            180                 185                 190

Pro Gln Ser Asp Pro Arg Leu Gln Gly Glu Leu Leu Pro Thr Tyr Thr
        195                 200                 205

His Tyr Leu Pro Pro Gly Ser Pro Thr Pro Tyr Asn Pro Pro Leu Ala
    210                 215                 220

Gly Ala Pro Met Pro Leu Thr His Leu
225                 230

<210> SEQ ID NO 18
<211> LENGTH: 384
<212> TYPE: PRT
<213> ORGANISM: Homo sapiens

<400> SEQUENCE: 18

Met Gln Arg Ser Pro Pro Gly Tyr Gly Ala Gln Asp Asp Pro Pro Ala
1               5                   10                  15

Arg Arg Asp Cys Ala Trp Ala Pro Gly His Gly Ala Ala Ala Asp Thr
            20                  25                  30

Arg Gly Leu Ala Ala Gly Pro Ala Ala Leu Ala Ala Pro Ala Ala Pro
```

-continued

```
              35                  40                  45
Ala Ser Pro Pro Ser Pro Gln Arg Ser Pro Pro Arg Ser Pro Glu Pro
    50                  55                  60

Gly Arg Tyr Gly Leu Ser Pro Ala Gly Arg Gly Glu Arg Gln Ala Ala
65                  70                  75                  80

Asp Glu Ser Arg Ile Arg Arg Pro Met Asn Ala Phe Met Val Trp Ala
                85                  90                  95

Lys Asp Glu Arg Lys Arg Leu Ala Gln Gln Asn Pro Asp Leu His Asn
            100                 105                 110

Ala Val Leu Ser Lys Met Leu Gly Lys Ala Trp Lys Glu Leu Asn Ala
            115                 120                 125

Ala Glu Lys Arg Pro Phe Val Glu Glu Ala Glu Arg Leu Arg Val Gln
    130                 135                 140

His Leu Arg Asp His Pro Asn Tyr Lys Tyr Arg Pro Arg Arg Lys Lys
145                 150                 155                 160

Gln Ala Arg Lys Ala Arg Arg Leu Glu Pro Gly Leu Leu Leu Pro Gly
            165                 170                 175

Leu Ala Pro Pro Gln Pro Pro Pro Glu Pro Phe Pro Ala Ala Ser Gly
            180                 185                 190

Ser Ala Arg Ala Phe Arg Glu Leu Pro Pro Leu Gly Ala Glu Phe Asp
            195                 200                 205

Gly Leu Gly Leu Pro Thr Pro Glu Arg Ser Pro Leu Asp Gly Leu Glu
    210                 215                 220

Pro Gly Glu Ala Ala Phe Phe Pro Pro Pro Ala Ala Pro Glu Asp Cys
225                 230                 235                 240

Ala Leu Arg Pro Phe Arg Ala Pro Tyr Ala Pro Thr Glu Leu Ser Arg
                245                 250                 255

Asp Pro Gly Gly Cys Tyr Gly Ala Pro Leu Ala Glu Ala Leu Arg Thr
            260                 265                 270

Ala Pro Pro Ala Ala Pro Leu Ala Gly Leu Tyr Tyr Gly Thr Leu Gly
            275                 280                 285

Thr Pro Gly Pro Tyr Pro Gly Pro Leu Ser Pro Pro Pro Glu Ala Pro
    290                 295                 300

Pro Leu Glu Ser Ala Glu Pro Leu Gly Pro Ala Ala Asp Leu Trp Ala
305                 310                 315                 320

Asp Val Asp Leu Thr Glu Phe Asp Gln Tyr Leu Asn Cys Ser Arg Thr
                325                 330                 335

Arg Pro Asp Ala Pro Gly Leu Pro Tyr His Val Ala Leu Ala Lys Leu
            340                 345                 350

Gly Pro Arg Ala Met Ser Cys Pro Glu Glu Ser Ser Leu Ile Ser Ala
            355                 360                 365

Leu Ser Asp Ala Ser Ser Ala Val Tyr Tyr Ser Ala Cys Ile Ser Gly
    370                 375                 380
```

```
<210> SEQ ID NO 19
<211> LENGTH: 454
<212> TYPE: PRT
<213> ORGANISM: Homo sapiens

<400> SEQUENCE: 19

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
            20                  25                  30
```

```
Ser Val Gln Pro Tyr Phe Tyr Cys Asp Glu Glu Glu Asn Phe Tyr Gln
        35              40              45

Gln Gln Gln Gln Ser Glu Leu Gln Pro Pro Ala Pro Ser Glu Asp Ile
    50              55              60

Trp Lys Lys Phe Glu Leu Leu Pro Thr Pro Pro Leu Ser Pro Ser Arg
65              70              75              80

Arg Ser Gly Leu Cys Ser Pro Ser Tyr Val Ala Val Thr Pro Phe Ser
                85              90              95

Leu Arg Gly Asp Asn Asp Gly Gly Gly Ser Phe Ser Thr Ala Asp
            100             105             110

Gln Leu Glu Met Val Thr Glu Leu Leu Gly Gly Asp Met Val Asn Gln
        115             120             125

Ser Phe Ile Cys Asp Pro Asp Asp Glu Thr Phe Ile Lys Asn Ile Ile
    130             135             140

Ile Gln Asp Cys Met Trp Ser Gly Phe Ser Ala Ala Ala Lys Leu Val
145             150             155             160

Ser Glu Lys Leu Ala Ser Tyr Gln Ala Ala Arg Lys Asp Ser Gly Ser
                165             170             175

Pro Asn Pro Ala Arg Gly His Ser Val Cys Ser Thr Ser Ser Leu Tyr
            180             185             190

Leu Gln Asp Leu Ser Ala Ala Ala Ser Glu Cys Ile Asp Pro Ser Val
        195             200             205

Val Phe Pro Tyr Pro Leu Asn Asp Ser Ser Ser Pro Lys Ser Cys Ala
    210             215             220

Ser Gln Asp Ser Ser Ala Phe Ser Pro Ser Ser Asp Ser Leu Leu Ser
225             230             235             240

Ser Thr Glu Ser Ser Pro Gln Gly Ser Pro Glu Pro Leu Val Leu His
                245             250             255

Glu Glu Thr Pro Pro Thr Thr Ser Ser Asp Ser Glu Glu Glu Gln Glu
            260             265             270

Asp Glu Glu Glu Ile Asp Val Val Ser Val Glu Lys Arg Gln Ala Pro
        275             280             285

Gly Lys Arg Ser Glu Ser Gly Ser Pro Ser Ala Gly Gly His Ser Lys
    290             295             300

Pro Pro His Ser Pro Leu Val Leu Lys Arg Cys His Val Ser Thr His
305             310             315             320

Gln His Asn Tyr Ala Ala Pro Pro Ser Thr Arg Lys Asp Tyr Pro Ala
                325             330             335

Ala Lys Arg Val Lys Leu Asp Ser Val Arg Val Leu Arg Gln Ile Ser
            340             345             350

Asn Asn Arg Lys Cys Thr Ser Pro Arg Ser Ser Asp Thr Glu Glu Asn
        355             360             365

Val Lys Arg Arg Thr His Asn Val Leu Glu Arg Gln Arg Arg Asn Glu
    370             375             380

Leu Lys Arg Ser Phe Phe Ala Leu Arg Asp Gln Ile Pro Glu Leu Glu
385             390             395             400

Asn Asn Glu Lys Ala Pro Lys Val Val Ile Leu Lys Lys Ala Thr Ala
                405             410             415

Tyr Ile Leu Ser Val Gln Ala Glu Glu Gln Lys Leu Ile Ser Glu Glu
            420             425             430

Asp Leu Leu Arg Lys Arg Arg Glu Gln Leu Lys His Lys Leu Glu Gln
        435             440             445

Leu Arg Asn Ser Cys Ala
```

-continued

450

<210> SEQ ID NO 20
<211> LENGTH: 464
<212> TYPE: PRT
<213> ORGANISM: Homo sapiens

<400> SEQUENCE: 20

```
Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
                20                  25                  30

Asp Asp Phe Tyr Phe Gly Gly Pro Asp Ser Thr Pro Pro Gly Glu Asp
            35                  40                  45

Ile Trp Lys Lys Phe Glu Leu Leu Pro Thr Pro Pro Leu Ser Pro Ser
    50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140

Ser Thr Ala Gln Ser Pro Gly Ala Gly Ala Ala Ser Pro Ala Gly Arg
145                 150                 155                 160

Gly His Gly Gly Ala Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Asp Glu Asp Asp Glu Glu Glu Asp
            260                 265                 270

Glu Glu Glu Glu Ile Asp Val Val Thr Val Glu Lys Arg Arg Ser Ser
        275                 280                 285

Ser Asn Thr Lys Ala Val Thr Thr Phe Thr Ile Thr Val Arg Pro Lys
    290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
        355                 360                 365
```

-continued

```
Ser Leu Ser Pro Arg Asn Ser Asp Ser Glu Asp Ser Glu Arg Arg Arg
    370             375             380

Asn His Asn Ile Leu Glu Arg Gln Arg Arg Asn Asp Leu Arg Ser Ser
385             390             395             400

Phe Leu Thr Leu Arg Asp His Val Pro Glu Leu Val Lys Asn Glu Lys
            405             410             415

Ala Ala Lys Val Val Ile Leu Lys Lys Ala Thr Glu Tyr Val His Ser
            420             425             430

Leu Gln Ala Glu Glu His Gln Leu Leu Leu Glu Lys Glu Lys Leu Gln
            435             440             445

Ala Arg Gln Gln Gln Leu Leu Lys Lys Ile Glu His Ala Arg Thr Cys
    450             455             460

<210> SEQ ID NO 21
<211> LENGTH: 364
<212> TYPE: PRT
<213> ORGANISM: Homo sapiens

<400> SEQUENCE: 21

Met Asp Tyr Asp Ser Tyr Gln His Tyr Phe Tyr Asp Tyr Asp Cys Gly
1               5               10              15

Glu Asp Phe Tyr Arg Ser Thr Ala Pro Ser Glu Asp Ile Trp Lys Lys
            20              25              30

Phe Glu Leu Val Pro Ser Pro Pro Thr Ser Pro Pro Trp Gly Leu Gly
            35              40              45

Pro Gly Ala Gly Asp Pro Ala Pro Gly Ile Gly Pro Pro Glu Pro Trp
    50              55              60

Pro Gly Gly Cys Thr Gly Asp Glu Ala Glu Ser Arg Gly His Ser Lys
65              70              75              80

Gly Trp Gly Arg Asn Tyr Ala Ser Ile Ile Arg Arg Asp Cys Met Trp
                85              90              95

Ser Gly Phe Ser Ala Arg Glu Arg Leu Glu Arg Ala Val Ser Asp Arg
            100             105             110

Leu Ala Pro Gly Ala Pro Arg Gly Asn Pro Pro Lys Ala Ser Ala Ala
            115             120             125

Pro Asp Cys Thr Pro Ser Leu Glu Ala Gly Asn Pro Ala Pro Ala Ala
    130             135             140

Pro Cys Pro Leu Gly Glu Pro Lys Thr Gln Ala Cys Ser Gly Ser Glu
145             150             155             160

Ser Pro Ser Asp Ser Glu Asn Glu Glu Ile Asp Val Val Thr Val Glu
            165             170             175

Lys Arg Gln Ser Leu Gly Ile Arg Lys Pro Val Thr Ile Thr Val Arg
            180             185             190

Ala Asp Pro Leu Asp Pro Cys Met Lys His Phe His Ile Ser Ile His
            195             200             205

Gln Gln Gln His Asn Tyr Ala Ala Arg Phe Pro Pro Glu Ser Cys Ser
    210             215             220

Gln Glu Glu Ala Ser Glu Arg Gly Pro Gln Glu Glu Val Leu Glu Arg
225             230             235             240

Asp Ala Ala Gly Glu Lys Glu Asp Glu Glu Asp Glu Glu Ile Val Ser
            245             250             255

Pro Pro Pro Val Glu Ser Glu Ala Ala Gln Ser Cys His Pro Lys Pro
            260             265             270

Val Ser Ser Asp Thr Glu Asp Val Thr Lys Arg Lys Asn His Asn Phe
    275             280             285
```

-continued

```
Leu Glu Arg Lys Arg Arg Asn Asp Leu Arg Ser Arg Phe Leu Ala Leu
    290                 295                 300

Arg Asp Gln Val Pro Thr Leu Ala Ser Cys Ser Lys Ala Pro Lys Val
305                 310                 315                 320

Val Ile Leu Ser Lys Ala Leu Glu Tyr Leu Gln Ala Leu Val Gly Ala
                325                 330                 335

Glu Lys Arg Met Ala Thr Glu Lys Arg Gln Leu Arg Cys Arg Gln Gln
                340                 345                 350

Gln Leu Gln Lys Arg Ile Ala Tyr Leu Thr Gly Tyr
            355                 360
```

```
<210> SEQ ID NO 22
<211> LENGTH: 155
<212> TYPE: PRT
<213> ORGANISM: Homo sapiens

<400> SEQUENCE: 22

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
    50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
                100                 105                 110

Asn Thr Tyr Arg Ser Arg Lys Tyr Thr Ser Trp Tyr Val Ala Leu Lys
            115                 120                 125

Arg Thr Gly Gln Tyr Lys Leu Gly Ser Lys Thr Gly Pro Gly Gln Lys
    130                 135                 140

Ala Ile Leu Phe Leu Pro Met Ser Ala Lys Ser
145                 150                 155
```

```
<210> SEQ ID NO 23
<211> LENGTH: 390
<212> TYPE: PRT
<213> ORGANISM: Homo sapiens

<400> SEQUENCE: 23

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
                20                  25                  30

Cys Lys Thr Ile Asp Met Glu Leu Val Lys Arg Lys Arg Ile Glu Ala
            35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95
```

-continued

```
Pro Glu Pro Glu Ala Asp Tyr Tyr Ala Lys Glu Val Thr Arg Val Leu
             100                 105                 110

Met Val Glu Thr His Asn Glu Ile Tyr Asp Lys Phe Lys Gln Ser Thr
             115                 120                 125

His Ser Ile Tyr Met Phe Phe Asn Thr Ser Glu Leu Arg Glu Ala Val
             130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                 165                 170                 175

Asn Ser Trp Arg Tyr Leu Ser Asn Arg Leu Leu Ala Pro Ser Asp Ser
                 180                 185                 190

Pro Glu Trp Leu Ser Phe Asp Val Thr Gly Val Val Arg Gln Trp Leu
                 195                 200                 205

Ser Arg Gly Gly Glu Ile Glu Gly Phe Arg Leu Ser Ala His Cys Ser
             210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                 245                 250                 255

Phe Leu Leu Leu Met Ala Thr Pro Leu Glu Arg Ala Gln His Leu Gln
                 260                 265                 270

Ser Ser Arg His Arg Arg Ala Leu Asp Thr Asn Tyr Cys Phe Ser Ser
             275                 280                 285

Thr Glu Lys Asn Cys Cys Val Arg Gln Leu Tyr Ile Asp Phe Arg Lys
             290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                 325                 330                 335

Ser Lys Val Leu Ala Leu Tyr Asn Gln His Asn Pro Gly Ala Ser Ala
             340                 345                 350

Ala Pro Cys Cys Val Pro Gln Ala Leu Glu Pro Leu Pro Ile Val Tyr
             355                 360                 365

Tyr Val Gly Arg Lys Pro Lys Val Glu Gln Leu Ser Asn Met Ile Val
             370                 375                 380

Arg Ser Cys Lys Cys Ser
385                 390
```

```
<210> SEQ ID NO 24
<211> LENGTH: 408
<212> TYPE: PRT
<213> ORGANISM: Homo sapiens

<400> SEQUENCE: 24
```

```
Met Ile Pro Gly Asn Arg Met Leu Met Val Val Leu Leu Cys Gln Val
1                 5                  10                  15

Leu Leu Gly Gly Ala Ser His Ala Ser Leu Ile Pro Glu Thr Gly Lys
                 20                 25                  30

Lys Lys Val Ala Glu Ile Gln Gly His Ala Gly Gly Arg Arg Ser Gly
             35                 40                  45

Gln Ser His Glu Leu Leu Arg Asp Phe Glu Ala Thr Leu Leu Gln Met
         50                 55                  60

Phe Gly Leu Arg Arg Arg Pro Gln Pro Ser Lys Ser Ala Val Ile Pro
```

-continued

```
65               70              75              80

Asp Tyr Met Arg Asp Leu Tyr Arg Leu Gln Ser Gly Glu Glu Glu Glu
                85              90              95

Glu Gln Ile His Ser Thr Gly Leu Glu Tyr Pro Glu Arg Pro Ala Ser
            100             105             110

Arg Ala Asn Thr Val Arg Ser Phe His His Glu Glu His Leu Glu Asn
            115             120             125

Ile Pro Gly Thr Ser Glu Asn Ser Ala Phe Arg Phe Leu Phe Asn Leu
            130             135             140

Ser Ser Ile Pro Glu Asn Glu Val Ile Ser Ser Ala Glu Leu Arg Leu
145             150             155             160

Phe Arg Glu Gln Val Asp Gln Gly Pro Asp Trp Glu Arg Gly Phe His
                165             170             175

Arg Ile Asn Ile Tyr Glu Val Met Lys Pro Pro Ala Glu Val Val Pro
            180             185             190

Gly His Leu Ile Thr Arg Leu Leu Asp Thr Arg Leu Val His His Asn
            195             200             205

Val Thr Arg Trp Glu Thr Phe Asp Val Ser Pro Ala Val Leu Arg Trp
            210             215             220

Thr Arg Glu Lys Gln Pro Asn Tyr Gly Leu Ala Ile Glu Val Thr His
225             230             235             240

Leu His Gln Thr Arg Thr His Gln Gly Gln His Val Arg Ile Ser Arg
                245             250             255

Ser Leu Pro Gln Gly Ser Gly Asn Trp Ala Gln Leu Arg Pro Leu Leu
            260             265             270

Val Thr Phe Gly His Asp Gly Arg Gly His Ala Leu Thr Arg Arg Arg
            275             280             285

Arg Ala Lys Arg Ser Pro Lys His His Ser Gln Arg Ala Arg Lys Lys
            290             295             300

Asn Lys Asn Cys Arg Arg His Ser Leu Tyr Val Asp Phe Ser Asp Val
305             310             315             320

Gly Trp Asn Asp Trp Ile Val Ala Pro Pro Gly Tyr Gln Ala Phe Tyr
            325             330             335

Cys His Gly Asp Cys Pro Phe Pro Leu Ala Asp His Leu Asn Ser Thr
            340             345             350

Asn His Ala Ile Val Gln Thr Leu Val Asn Ser Val Asn Ser Ser Ile
            355             360             365

Pro Lys Ala Cys Cys Val Pro Thr Glu Leu Ser Ala Ile Ser Met Leu
            370             375             380

Tyr Leu Asp Glu Tyr Asp Lys Val Val Leu Lys Asn Tyr Gln Glu Met
385             390             395             400

Val Val Glu Gly Cys Gly Cys Arg
                405
```

```
<210> SEQ ID NO 25
<211> LENGTH: 352
<212> TYPE: PRT
<213> ORGANISM: Homo sapiens

<400> SEQUENCE: 25

Met Ala Pro Leu Gly Tyr Phe Leu Leu Leu Cys Ser Leu Lys Gln Ala
1               5               10              15

Leu Gly Ser Tyr Pro Ile Trp Trp Ser Leu Ala Val Gly Pro Gln Tyr
            20              25              30
```

```
Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
    50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
    290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350
```

```
<210> SEQ ID NO 26
<211> LENGTH: 60
<212> TYPE: DNA
<213> ORGANISM: Artificial
<220> FEATURE:
<223> OTHER INFORMATION: primer

<400> SEQUENCE: 26
catgacatcg actacaagga tgacgatgac aaggctgtca gcgacgcgct gctcccatct     60

<210> SEQ ID NO 27
<211> LENGTH: 60
<212> TYPE: DNA
<213> ORGANISM: Artificial
<220> FEATURE:
<223> OTHER INFORMATION: primer
```

<400> SEQUENCE: 27
atctttataa tcaccgtcat ggtctttgta gtccatgaat tcccgtacca ccacactggg          60

<210> SEQ ID NO 28
<211> LENGTH: 513
<212> TYPE: PRT
<213> ORGANISM: Homo sapiens

<400> SEQUENCE: 28

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
                100                 105                 110

Leu Thr His Pro Pro Glu Ser Val Ala Ala Thr Val Ser Ser Ser Ala
            115                 120                 125

Ser Ala Ser Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
            195                 200                 205

Asp Pro Val Tyr Ile Pro Pro Gln Gln Pro Gln Pro Pro Gly Gly Gly
        210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

-continued

```
Pro Asp Gln Met Gln Pro Gln Val Pro Pro Leu His Tyr Gln Gly Gln
        355             360             365

Ser Arg Gly Phe Val Ala Arg Ala Gly Glu Pro Cys Val Cys Trp Pro
        370             375             380

His Phe Gly Thr His Gly Met Met Leu Thr Pro Pro Ser Ser Pro Leu
385             390             395             400

Glu Leu Met Pro Pro Gly Ser Cys Met Pro Glu Glu Pro Lys Pro Lys
                405             410             415

Arg Gly Arg Arg Ser Trp Pro Arg Lys Arg Thr Ala Thr His Thr Cys
                420             425             430

Asp Tyr Ala Gly Cys Gly Lys Thr Tyr Thr Lys Ser Ser His Leu Lys
        435             440             445

Ala His Leu Arg Thr His Thr Gly Glu Lys Pro Tyr His Cys Asp Trp
        450             455             460

Asp Gly Cys Gly Trp Lys Phe Ala Arg Ser Asp Glu Leu Thr Arg His
465             470             475             480

Tyr Arg Lys His Thr Gly His Arg Pro Phe Gln Cys Gln Lys Cys Asp
                485             490             495

Arg Ala Phe Ala Arg Ser Asp His Leu Ala Leu His Met Lys Arg His
                500             505             510

Phe
```

```
<210> SEQ ID NO 29
<211> LENGTH: 3038
<212> TYPE: DNA
<213> ORGANISM: Homo sapiens

<400> SEQUENCE: 29
ggcagtttcc cgaccagaga gaacgaacgt gtctgcgggc gcgcgggggag cagaggcggt      60 ggcgggcggc ggcggcaccg ggagccgccg agtgaccctc ccccgcccct ctggcccccc     120
accctcccac ccgcccgtgg cccgcgccca tggccgcgcg cgctccacac aactcaccgg     180
agtccgcgcc ttgcgccgcc gaccagttcg cagctccgcg ccacggcagc cagtctcacc     240
tggcggcacc gcccgcccac cgccccggcc acagcccctg cgcccacggc agcactcgag     300
gcgaccgcga cagtggtggg ggacgctgct gagtggaaga gagcgcagcc cggccaccgg     360
acctacttac tcgccttgct gattgtctat ttttgcgttt acaacttttc taagaacttt     420
tgtatacaaa ggaacttttt aaaaaagacg cttccaagtt atatttaatc caaagaagaa     480
ggatctcggc caatttgggg ttttgggttt tggcttcgtt tcttctcttc gttgactttg     540
gggttcaggt gccccagctg cttcgggctg ccgaggacct tctgggcccc cacattaatg     600
aggcagccac ctggcgagtc tgacatggct gtcagcgacg cgctgctccc atctttctcc     660
acgttcgcgt ctggcccggc gggaagggag aagacactgc gtcaagcagg tgccccgaat     720
aaccgctggc gggaggagct ctcccacatg aagcgacttc ccccagtgct tcccggccgc     780
ccctatgacc tggcggcggc gaccgtggcc acagacctgg agagcggcgg agccggtgcg     840
gcttgcggcg gtagcaacct ggcgcccta cctcggagag agaccgagga gttcaacgat     900
ctcctggacc tggactttat tctctccaat tcgctgaccc atcctccgga gtcagtggcc     960
gccaccgtgt cctcgtcagc gtcagcctcc tcttcgtcgt cgccgtcgag cagcggccct    1020
gccagcgcgc cctccacctg cagcttcacc tatccgatcc gggccgggaa cgacccgggc    1080
gtggcgccgg gcgcacgggg cggaggcctc ctctatggca gggagtccgc tcccccctccg    1140 acggctccct tcaacctggc ggacatcaac gacgtgagcc cctcgggcgg cttcgtggcc    1200
```

-continued

```
gagctcctgc ggccagaatt ggacccggtg tacattccgc cgcagcagcc gcagccgcca      1260
ggtggcgggc tgatgggcaa gttcgtgctg aaggcgtcgc tgagcgcccc tggcagcgag      1320
tacggcagcc cgtcggtcat cagcgtcagc aaaggcagcc ctgacggcag ccacccggtg      1380
gtggtggcgc cctacaacgg cgggccgccg cgcacgtgcc ccaagatcaa gcaggaggcg      1440
gtctcttcgt gcacccactt gggcgctgga cccctctca gcaatggcca ccggccggct      1500
gcacacgact tccccctggg gcggcagctc ccagcagga ctaccccgac cctgggtctt      1560
gaggaagtgc tgagcagcag ggactgtcac cctgccctgc gcttcctcc cggcttccat      1620 ccccacccgg ggcccaatta cccatccttc ctgcccgatc agatgcagcc gcaagtcccg      1680
ccgctccatt accaaggtca gtcccgggga tttgtagctc gggctgggga gccctgtgtg      1740
tgctggcccc acttcgggac acacgggatg atgctcaccc caccttcttc accccctagag      1800 ctcatgccac ccggttcctg catgccagag gagcccaagc caaagagggg aagacgatcg      1860 tggcccecgga aaaggaccgc cacccacact tgtgattacg cgggctgcgg caaaacctac      1920
acaaagagtt cccatctcaa ggcacacctg cgaacccaca caggtgagaa accttaccac      1980
tgtgactggg acggctgtgg atggaaattc gcccgctcag atgaactgac caggcactac      2040
cgtaaacaca cggggcaccg cccgttccag tgccaaaaat gcgaccgagc attttccagg      2100
tcggaccacc tcgccttaca catgaagagg catttttaaa tcccagacag tggatatgac      2160
ccacactgcc agaagagaat tcagtatttt ttacttttca cactgtcttc ccgatgaggg      2220
aaggagccca gccagaaagc actacaatca tggtcaagtt cccaactgag tcatcttgtg      2280
agtggataat caggaaaaat gaggaatcca aaagacaaaa atcaaagaac agatggggtc      2340
tgtgactgga tcttctatca ttccaattct aaatccgact tgaatattcc tggacttaca      2400
aaatgccaag ggggtgactg gaagttgtgg atatcagggt ataaattata tccgtgagtt      2460 gggggagggga agaccagaat tcccttgaat tgtgtattga tgcaatataa gcataaaaga      2520
tcaccttgta ttctctttac cttctaaaag ccattattat gatgttagaa gaagaggaag      2580
aaattcaggt acagaaaaca tgtttaaata gcctaaatga tggtgcttgg tgagtcttgg      2640
ttctaaaggt accaaacaag gaagccaaag ttttcaaact gctgcatact ttgacaagga      2700
aaatctatat ttgtcttccg atcaacattt atgacctaag tcaggtaata tacctggttt      2760
acttctttag catttttatg cagacagtct gttatgcact gtggtttcag atgtgcaata      2820
atttgtacaa tggtttattc ccaagtatgc cttaagcaga acaaatgtgt ttttctatat      2880
agttccttgc cttaataaat atgtaatata aatttaagca aacgtctatt ttgtatattt      2940
gtaaactaca aagtaaaatg aacattttgt ggagtttgta ttttgcatac tcaaggtgag      3000
aattaagttt taaataaacc tataatattt tatctgaa                              3038
```

<210> SEQ ID NO 30
<211> LENGTH: 513
<212> TYPE: PRT
<213> ORGANISM: Homo sapiens

<400> SEQUENCE: 30

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
                20                  25                  30

Thr Leu Arg Gln Ala Gly Ala Pro Asn Asn Arg Trp Arg Glu Glu Leu
        35                  40                  45
```

```
Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
                100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
                180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
                260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
                340                 345                 350

Pro Asp Gln Met Gln Pro Gln Val Pro Pro Leu His Tyr Gln Gly Gln
        355                 360                 365

Ser Arg Gly Phe Val Ala Arg Ala Gly Glu Pro Cys Val Cys Trp Pro
    370                 375                 380

His Phe Gly Thr His Gly Met Met Leu Thr Pro Pro Ser Ser Pro Leu
385                 390                 395                 400

Glu Leu Met Pro Pro Gly Ser Cys Met Pro Glu Glu Pro Lys Pro Lys
                405                 410                 415

Arg Gly Arg Arg Ser Trp Pro Arg Lys Arg Thr Ala Thr His Thr Cys
                420                 425                 430

Asp Tyr Ala Gly Cys Gly Lys Thr Tyr Thr Lys Ser Ser His Leu Lys
        435                 440                 445

Ala His Leu Arg Thr His Thr Gly Glu Lys Pro Tyr His Cys Asp Trp
    450                 455                 460
```

-continued

```
Asp Gly Cys Gly Trp Lys Phe Ala Arg Ser Asp Glu Leu Thr Arg His
465             470             475             480

Tyr Arg Lys His Thr Gly His Arg Pro Phe Gln Cys Gln Lys Cys Asp
            485             490             495

Arg Ala Phe Ser Arg Ser Asp His Leu Ala Ala His Met Lys Arg His
            500             505             510

Phe
```

<210> SEQ ID NO 31
<211> LENGTH: 3038
<212> TYPE: DNA
<213> ORGANISM: Homo sapiens

<400> SEQUENCE: 31

```
ggcagtttcc cgaccagaga gaacgaacgt gtctgcgggc gcgcggggag cagaggcggt      60
ggcgggcggc ggcggcaccg ggagccgccg agtgaccctc ccccgcccct ctggcccccc     120
accctcccac ccgcccgtgg cccgcgccca tggccgcgcg cgctccacac aactcaccgg     180
agtccgcgcc ttgcgccgcc gaccagttcg cagctccgcg ccacggcagc cagtctcacc     240
tggcggcacc gcccgcccac cgccccggcc acagcccctg cgcccacggc agcactcgag     300
gcgaccgcga cagtggtggg ggacgctgct gagtggaaga gagcgcagcc cggccaccgg     360
acctacttac tcgccttgct gattgtctat ttttgcgttt acaacttttc taagaacttt     420
tgtatacaaa ggaacttttt aaaaaagacg cttccaagtt atatttaatc caaagaagaa     480
ggatctcggc caatttgggg ttttgggttt tggcttcgtt tcttctcttc gttgactttg     540
gggttcaggt gccccagctg cttcgggctg ccgaggacct tctgggcccc cacattaatg     600
aggcagccac ctggcgagtc tgacatggct gtcagcgacg cgctgctccc atctttctcc     660
acgttcgcgt ctggcccggc gggaagggag aagacactgc gtcaagcagg tgccccgaat     720
aaccgctggc gggaggagct ctcccacatg aagcgacttc ccccagtgct tcccggccgc     780
ccctatgacc tggcggcggc gaccgtggcc acagacctgg agagcggcgg agccggtgcg     840
gcttgcggcg gtagcaacct ggcgccccta cctcggagag agaccgagga gttcaacgat     900
ctcctggacc tggactttat tctctccaat tcgctgaccc atcctccgga gtcagtggcc     960
gccaccgtgt cctcgtcagc gtcagcctcc tcttcgtcgt cgccgtcgag cagcggccct    1020
gccagcgcgc cctccacctg cagcttcacc tatccgatcc gggccgggaa cgacccgggc    1080
gtggcgccgg cggcacggg cggaggcctc ctctatggca gggagtccgc tcccctccg     1140 acggctccct tcaacctggc ggacatcaac gacgtgagcc cctcgggcgg cttcgtggcc    1200
gagctcctgc ggccagaatt ggacccggtg tacattccgc cgcagcagcc gcagccgcca    1260
ggtggcgggc tgatgggcaa gttcgtgctg aaggcgtcgc tgagcgcccc tggcagcgag    1320
tacggcagcc cgtcggtcat cagcgtcagc aaaggcagcc ctgacggcag ccacccggtg    1380
gtggtggcgc cctacaacgg cgggccgccg cgcacgtgcc ccaagatcaa gcaggaggcg    1440
gtctcttcgt gcacccactt gggcgctgga cccctctca gcaatggcca ccggccggct    1500
gcacacgact ccccctggg gcggcagctc cccagcagga ctaccccgac cctgggtctt    1560
gaggaagtgc tgagcagcag ggactgtcac cctgccctgc cgcttcctcc cggcttccat    1620
ccccacccgg ggcccaatta cccatccttc ctgcccgatc agatgcagcc gcaagtcccg    1680 ccgtccatt accaaggtca gtcccgggga tttgtagctc gggctgggga ccctgtgtg     1740 tgctggcccc acttcgggac acacgggatg atgctcaccc caccttcttc accccctagag    1800
```

-continued

```
ctcatgccac ccggttcctg catgccagag gagcccaagc caaagagggg aagacgatcg   1860
tggccccgga aaaggaccgc cacccacact tgtgattacg cgggctgcgg caaaacctac   1920
acaaagagtt cccatctcaa ggcacacctg cgaacccaca caggtgagaa accttaccac   1980
tgtgactggg acggctgtgg atggaaattc gcccgctcag atgaactgac caggcactac   2040
cgtaaacaca cggggcaccg cccgttccag tgccaaaaat gcgaccgagc atttgccagg   2100
tcggaccacc tcgccgcaca catgaagagg catttttaaa tcccagacag tggatatgac   2160
ccacactgcc agaagagaat tcagtatttt ttacttttca cactgtcttc ccgatgaggg   2220
aaggagccca gccagaaagc actacaatca tggtcaagtt cccaactgag tcatcttgtg   2280
agtggataat caggaaaaat gaggaatcca aaagacaaaa atcaaagaac agatggggtc   2340
tgtgactgga tcttctatca ttccaattct aaatccgact tgaatattcc tggacttaca   2400
aaatgccaag ggggtgactg gaagttgtgg atatcagggt ataaattata tccgtgagtt   2460
gggggaggga agaccagaat tcccttgaat tgtgtattga tgcaatataa gcataaaaga   2520
tcaccttgta ttctctttac cttctaaaag ccattattat gatgttagaa gaagaggaag   2580
aaattcaggt acagaaaaca tgtttaaata gcctaaatga tggtgcttgg tgagtcttgg   2640
ttctaaaggt accaaacaag gaagccaaag ttttcaaact gctgcatact ttgacaagga   2700
aaatctatat ttgtcttccg atcaacattt atgacctaag tcaggtaata tacctggttt   2760
acttctttag cattttatg cagacagtct gttatgcact gtggtttcag atgtgcaata   2820
atttgtacaa tggtttattc ccaagtatgc cttaagcaga acaaatgtgt ttttctatat   2880
agttccttgc cttaataaat atgtaatata aatttaagca aacgtctatt ttgtatattt   2940
gtaaactaca aagtaaaatg aacattttgt ggagtttgta ttttgcatac tcaaggtgag   3000
aattaagttt taaataaacc tataatattt tatctgaa                            3038
```